(12) United States Patent
Jackson et al.

(10) Patent No.: US 7,138,236 B1
(45) Date of Patent: Nov. 21, 2006

(54) INTERACTIONS OF ATM, ATR OR DAN-PK WITH P53

(75) Inventors: Stephen Philip Jackson, Cambridge (GB); Nicholas David Lakin, Cambridge (GB); Graeme Cameron Murray Smith, Cambridge (GB)

(73) Assignee: Kudos Pharmaceuticals Limited, Cambridge (GB)

( * ) Notice: Subject to any disclaimer, the term of this patent is extended or adjusted under 35 U.S.C. 154(b) by 0 days.

(21) Appl. No.: 09/462,962

(22) PCT Filed: Jul. 16, 1998

(86) PCT No.: PCT/GB98/02115

§ 371 (c)(1),
(2), (4) Date: Jun. 25, 2001

(87) PCT Pub. No.: WO99/04266

PCT Pub. Date: Jan. 28, 1999

(30) Foreign Application Priority Data

Jul. 16, 1997 (GB) .................................... 9714971

(51) Int. Cl.
*G01N 33/53* (2006.01)
(52) U.S. Cl. .................... 435/7.1; 435/15; 435/194; 435/325; 435/320.1; 435/252.3; 530/350; 530/300
(58) Field of Classification Search ............ 435/7.1, 435/15, 194, 325, 320.1, 252.3; 530/350, 530/300
See application file for complete search history.

(56) References Cited

U.S. PATENT DOCUMENTS

| 6,348,311 | B1 | 2/2002 | Kastan et al. .............. 435/5 |
| 6,387,640 | B1 | 5/2002 | Kastan et al. .............. 435/15 |

FOREIGN PATENT DOCUMENTS

| WO | 94 12202 | 6/1994 |
| WO | 97 18323 | 5/1997 |
| WO | 98 56391 | 12/1998 |
| WO | WO 98/55602 A1 | 12/1998 |

OTHER PUBLICATIONS

Oncogene, vol. 13, p. 1133-1138, 1996.*
Baskaran et al., Letters to Nature, vol. 387, pp. 516-519, 1997.*
Banin et al., (1998), *Science*, 281:1674-1677.
Canman et al., (1998), *Science*, 281:1677-1679.
Cimprich, et al., "cDNA Cloning and Gene Mapping of a Candidate Human Cell Cycle Checkpoint Protein," *Proc. Natl. Acad. Sci. USA* (Apr. 1996) vol. 93:2850-2855.
Enoch, Tamar, et al., "Cellular Responses to DNA damage: Cell-Cycle Checkpoints, Apoptosis and the Roles of p53 and ATM," *TIBS 20* (Oct. 1995) pp. :426-430.
Hartley, Katherine O., et al., "DNA-Dependent Protein Kinase Catalytic Subunit: A Relative of Phosphatodylinositol 3-Kinase and the Ataxia Telangiectasia Gene Product," *Cell* (Sep. 8, 1995) vol. 82:849-856.
Meyn, Stephen M., "Ataxia-Telangiectasia and Cellular Responses to DNA Damage," *Cancer Research* (Dec. 15, 1995) vol. 55:5991-6001.
Savitsky, Kinnert, et al., "A Single Ataxia Telangiectasia Gene with a Product Similiar to Pl-3 Kinase," *Science* (Jun. 23, 1995) vol. 268:1749-1753.
Savitsky, Kinnert, et al., "The Complete Sequence of the Coding Region of the ATM Gene Reveals Similarity to Cell Cycle Regulators in Different Species," *Human Molecular Genetics* (1995) vol. 4, No. 11:2025-2032.
Shieh, Sheau-Yann, et al., "DNA Damage-Induced Phosphorylation of p53 Alleviates Inhibition by MDM2," *Cell* (Oct. 31, 1997) vol. 91:325-334.
Suwa, Akira, et al., DNA-Dependent Protein Kinase (Ku protein-p350 complex) Assembles on Double-Stranded DNA, *Proc. Natl. Acad. Sci. USA* (Jul. 1994) vol. 91:6904-6908.

* cited by examiner

*Primary Examiner*—Kathleen M. Kerr
*Assistant Examiner*—Hope Robinson
(74) *Attorney, Agent, or Firm*—Pamela J. Sherwood; Bozicevic, Field & Francis LLP

(57) ABSTRACT

The interaction of ATM and related protein kinases such as ATR and DNA-PK with p53 is disclosed, in particular the phosphorylation of Ser15 and Thr18 by these proteins. The activity of the proteins is shown to increase in the presence of DNA. Assays for modulators of phosphorylation by the interaction between the proteins and p53 or other proteins having similar phosphorylation sites are provided. Methods of purifying ATM or ATR employing DNA or NTA are also disclosed.

2 Claims, 30 Drawing Sheets

Fig.2.
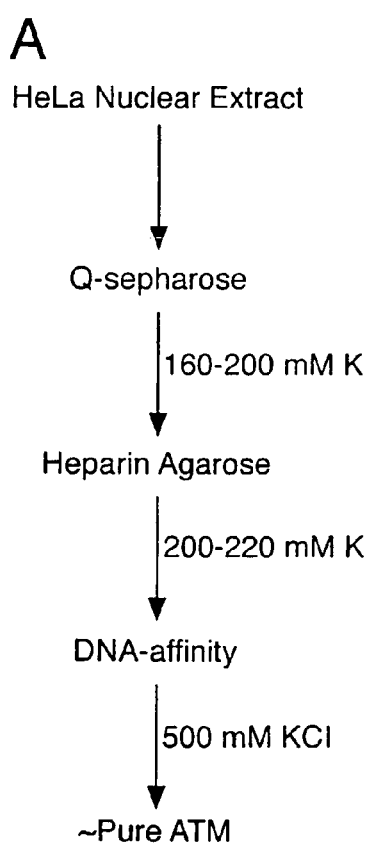
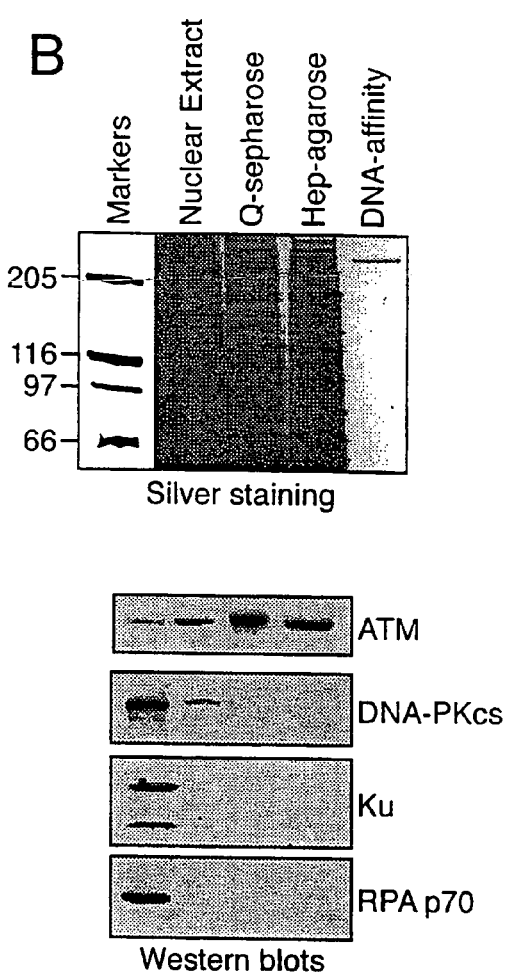

Figure 6a

```
/gene="ATM"
/translation="MSLVLNDLLICCRQLEHDRATERKKEVEKFKRLIRDPETIKHLDR
HSDSKQGKYLNWDAVFRFLQKYIQKETECLRIAKPNVSASTQASRQKKMQEISSLVKYF
IKCANRRAPRLKCQELLNYIMDTVKDSSNGAIYGADCSNILLKDILSVRKYWCEISQQQ
WLELFSVYFRLYLKPSQDVHRVLVARIIHAVTKGCCSQTDGLNSKFLDFFSKAIQCARQ
EKSSSGLNHILAALTIFLKTLAVNFRIRVCELGDEILPTLLYIWTQHRLNDSLKEVIIE
LFQLQIYIHHPKGAKTQEKGAYESTKWRSILYNLYDLLVNEISHIGSRGKYSSGFRNIA
VKENLIELMADICHQVFNEDTRSLEISQSYTTTQRESSDYSVPCKRKKIELGWEVIKDH
LQKSQNDFDLVPWLQIATQLISKYPASLPNCELSPLLMILSQLLPQQRHGERTPYVLRC
LTEVALCQDKRSNLESSQKSDLLKLWNKIWCITFRGISSEQIQAENFGLLGAIIQGSLV
EVDREFWKLFTGSACRPSCPAVCCLTLALTTSIVPGAVKMGIEQNMCEVNRSFSLKESI
MKWLLFYQLEGDLENSTEVPPILHSNFPHLVLEKILVSLTMKNCKAAMNFFQSVPECEH
HQKDKEELSFSEVEELFLQTTFDKMDFLTIVRECGIEKHQSSIGFSVHQNLKESLDRCL
LGLSEQLLNNYSSEITNSETLVRCSRLLVGVLGVCYCYMGVIAEEEAYKSELFQKANSLM
QCAGESITLFKNKTNEEFRIGSLRNMMQLCTRCLSNCTKKSPNKIASGFFLRLLTSKLM
NDIADICKSLASFIKKPFDRGEVESMEDDTNGNLMEVEDQSSMNLFNDYPDSSVSDANE
PGESQSTIGAINPLAEEYLSKQDLLFLDMLKFLCLCVTTAQTNTVSFRAADIRRKLLML
IDSSTLEPTKSLHLHMYLMLLKELPGEEYPLPMEDVLELLKPLSNVCSLYRRDQDVCKT
ILNHVLHVVKNLGQSNMDSENTRDAQGQFLTVIGAFWHLTKERKYIFSVRMALVNCLKT
LLEADPYSKWAILNVMGKDFPVNEVFTQFLADNHHQVRMLAAESINRLFQDTKGDSSRL
LKALPLKLQQTAFENAYLKAQBGMREMSHSAENPETLDEIYNRKSVLLTLIAVVLSCSP
ICEKQALFALCKSVKENGLEPHLVKKVLEKVSETFGYRRLEDFMASHLDYLVLEWLNLQ
DTEYNLSSFPFILLNYTNIEDFYRSCYKVLIPHLVIRSHFDEVKSIANQIQEDWKSLLT
DCFPKILVNILPYFAYEGTRDSGMAQQRETATKVYDMLKSENLLGKQIDHLFISNLPEI
VVELLMTLHEPANSSASQSTDLCDFSGDLDPAPNPPHFPSHVIKATFAYISNCHKTKLK
SILEILSKSPDSYQKILLAICEQAAETNNVYKKHRILKIYHLFVSLLLKDIKSGLGGAW
AFVLRDVIYTLIHYINQRPSCIMDVSLRSFSLCCDLLSQVCQTAVTYCKDALENHLHVI
VGTLIPLVYEQVEVQKQVLDLLKYLVIDNKDNENLYITIKLLDPFPDHVVFKDLRITQQ
KIKYSRGPFSLLEEINHFLSVSVYDALPLTRLEGLKDLRRQLELHKDQMVDIMRASQDN
PQDGIMVKLVVNLLQLSKMAINHTGEKEVLEAVGSCLGEVGPIDFSTIAIQHSKDASYT
KALKLFEDKELQWTFIMLTYLNNTLVEDCVKVRSAAVTCLKNILATKTGHSFWEIYKMT
TDPMLAYLQPFRTSRKKFLEVPRFDKENPFEGLDDINLWIPLSENHDIWIKTLTCAFLD
SGGTKCEILQLLKPMCEVKTDFCQTVLPYLIHDILLQDTNESWRNLLSTHVQGFFTSCL
RHFSQTSRSTTPANLDSESEHFFRCCLDKKSQRTMLAVVDYMRRQKRPSSGTIFNDAFW
LDLNYLEVAKVAQSCAAHFTALLYAEIYADKKSMDDQEKRSLAFEEGSQSTTISSLSEK
SKEETGISLQDLLLEIYRSIGEPDSLYGCGGGKMLQPITRLRTYEHEAMWGKALVTYDL
ETAIPSSTRQAGIIQALQNLGLCHILSVYLKGLDYENKDWCPELEELHYQAAWRNMQWD
HCTSVSKEVEGTSYHESLYNALQSLRDREFSTFYESLKYARVKEVEEMCKRSLESVYSL
YPTLSRLQAIGELESIGELFSRSVTHRQLSEVYIKWQKHSQLLKDSDFSFQEPIMALRT
VILEILMEKEMDNSQRECIKDILTKHLVELSILARTFKNTQLPERAIFQIKQYNSVSCG
VSEWQLEEAQVFWAKKEQSLALSILKQMIKKLDASCAANNPSLKLTYTECLRVCGNWLA
ETCLENPAVIMQTYLEKAVEVAGNYDGESSDELRNGKMKAFLSLARFSDTQYQRIENYM
KSSEFENKQALLKRAKEEVGLLREHKIQTNRYTVKVQRELELDELALRALKEDRKRFLC
KAVENYINCLLSGEEHDMWVFRLCSLWLENSGVSEVNGMMKRDGMKIPTYKFLPLMYQL
AARMGTKMMGGLGFHEVLNNLISRISMDHPHHTLFIILALANANRDEFLTKPEVARRSR
ITKNVPKQSSQLDEDRTEAANRIICTIRSRRPQMVRSVEALCDAYIILANLDATQWKTQ
RKGINIPADQPITKLKNLEDVVVPTMEIKVDHTGEYGNLVTIQSFKAEFRLAGGVNLPK ⎤
IIDCVGSDGKERRQLVKGRDDLRQDAVMQQVFQMCNTLLQRNTETRKRKLTICTYKVVP │ KINASE
LSQRSGVLEWCTGTVPIGEFLVNNEDGAHKRYRPNDFSAFQCQKKMMEVQKKSFEEKYE │ DOMAIN
VFMDVCQNFQPVFRYFCMEKFLDPAIWFEKRLAYTRSVATSSIVGYILGLGDRHVQNIL │
INEQSAELVHIDLGVAFEQGKILPTPETVPFRLTRDIVDGMGITGVEGVFRRCCEKTME │
VMRNSQETLLTIVEVLLYDPLFDWIMNPLKALYLQQRPEDETELHPTLNADDQECKRNL │
SDIDQSFDKVAERVLMRLQEKLKGVEEGTVLSVGGQVNLLIQQAIDPKNLSRLFPGWKA │
WV" ⎦
```

Figure 6b (1)

Sequence 9385 BP; 3030 A; 1685 C; 1973 G; 2697 T; 0 other;
U33841  Length: 9385  July 10, 1998 12:06  Type: N  Check: 7765

```
   1  GCGAGAGGAG  TCGGGATCTG  CGCTGCAGCC  ACCGCCGCGG  TTGATACTAC
  51  TTTGACCTTC  CGAGTGCAGT  GAGGCATACA  TCACAATTTG  GAATTATGCA
 101  TTGGTTTATC  AATTTACTTG  TTTATTGTCA  CCCTGCTGCC  CAGATATGAC
 151  TTCATGAGGA  CAGTGATGTG  TGTTCTGAAA  TTGTGAACCA  TGAGTCTAGT
```

Figure 6b (ii)

```
 201  ACTTAATGAT CTGCTTATCT GCTGCCGTCA ACTAGAACAT GATAGAGCTA
 251  CAGAACGAAA GAAAGAAGTT GAGAAATTTA AGCGCCTGAT TCGAGATCCT
 301  GAAACAATTA AACATCTAGA TCGGCATTCA GATTCCAAAC AAGGAAAATA
 351  TTTGAATTGG GATGCTGTTT TTAGATTTTT ACAGAAATAT ATTCAGAAAG
 401  AAACAGAATG TCTGAGAATA GCAAAACCAA ATGTATCAGC CTCAACACAA
 451  GCCTCCAGGC AGAAAAAGAT GCAGGAAATC AGTAGTTTGG TCAAATACTT
 501  CATCAAATGT GCAAACAGAA GAGCACCTAG GCTAAAATGT CAAGAACTCT
 551  TAAATTATAT CATGGATACA GTGAAAGATT CATCTAATGG TGCTATTTAC
 601  GGAGCTGATT GTAGCAACAT ACTACTCAAA GACATTCTTT CTGTGAGAAA
 651  ATACTGGTGT GAAATATCTC AGCAACAGTG GTTAGAATTG TTCTCTGTGT
 701  ACTTCAGGCT CTATCTGAAA CCTTCACAAG ATGTTCATAG AGTTTTAGTG
 751  GCTAGAATAA TTCATGCTGT TACCAAAGGA TGCTGTTCTC AGACTGACGG
 801  ATTAAATTCC AAATTTTTGG ACTTTTTTTC CAAGGCTATT CAGTGTGCGA
 851  GACAAGAAAA GAGCTCTTCA GGTCTAAATC ATATCTTAGC AGCTCTTACT
 901  ATCTTCCTCA AGACTTTGGC TGTCAACTTT CGAATTCGAG TGTGTGAATT
 951  AGGAGATGAA ATTCTTCCCA CTTTGCTTTA TATTTGGACT CAACATAGGC
1001  TTAATGATTC TTTAAAAGAA GTCATTATTG AATTATTTCA ACTGCAAATT
1051  TATATCCATC ATCCGAAAGG AGCCAAAACC CAAGAAAAAG GTGCTTATGA
1101  ATCAACAAAA TGGAGAAGTA TTTTATACAA CTTATATGAT CTGCTAGTGA
1151  ATGAGATAAG TCATATAGGA AGTAGAGGAA AGTATTCTTC AGGATTTCGT
1201  AATATTGCCG TCAAAGAAAA TTTGATTGAA TTGATGGCAG ATATCTGTCA
1251  CCAGGTTTTT AATGAAGATA CCAGATCCTT GGAGATTTCT CAATCTTACA
1301  CTACTACACA AAGAGAATCT AGTGATTACA GTGTCCCTTG CAAAAGGAAG
1351  AAAATAGAAC TAGGCTGGGA AGTAATAAAA GATCACCTTC AGAAGTCACA
1401  GAATGATTTT GATCTTGTGC CTTGGCTACA GATTGCAACC CAATTAATAT
1451  CAAAGTATCC TGCAAGTTTA CCTAACTGTG AGCTGTCTCC ATTACTGATG
1501  ATACTATCTC AGCTTCTACC CCAACAGCGA CATGGGGAAC GTACACCATA
1551  TGTGTTACGA TGCCTTACGG AAGTTGCATT GTGTCAAGAC AAGAGGTCAA
1601  ACCTAGAAAG CTCACAAAAG TCAGATTTAT TAAAACTCTG GAATAAAATT
1651  TGGTGTATTA CCTTTCGTGG TATAAGTTCT GAGCAAATAC AAGCTGAAAA
1701  CTTTGGCTTA CTTGGAGCCA TAATTCAGGG TAGTTTAGTT GAGGTTGACA
1751  GAGAATTCTG GAAGTTATTT ACTGGGTCAG CCTGCAGACC TTCATGTCCT
1801  GCAGTATGCT GTTTGACTTT GGCACTGACC ACCAGTATAG TTCCAGGAGC
1851  GGTAAAAATG GAATAGAGC AAAATATGTG TGAAGTAAAT AGAAGCTTTT
```

Figure 6 b (iii)

```
1901  CTTTAAAGGA ATCAATAATG AAATGGCTCT TATTCTATCA GTTAGAGGGT
1951  GACTTAGAAA ATAGCACAGA AGTGCCTCCA ATTCTTCACA GTAATTTTCC
2001  TCATCTTGTA CTGGAGAAAA TTCTTGTGAG TCTCACTATG AAAAACTGTA
2051  AAGCTGCAAT GAATTTTTTC CAAAGCGTGC CAGAATGTGA ACACCACCAA
2101  AAAGATAAAG AAGAACTTTC ATTCTCAGAA GTAGAAGAAC TATTTCTTCA
2151  GACAACTTTT GACAAGATGG ACTTTTTAAC CATTGTGAGA GAATGTGGTA
2201  TAGAAAAGCA CCAGTCCAGT ATTGGCTTCT CTGTCCACCA GAATCTCAAG
2251  GAATCACTGG ATCGCTGTCT TCTGGGATTA TCAGAACAGC TTCTGAATAA
2301  TTACTCATCT GAGATTACAA ATTCAGAAAC TCTTGTCCGG TGTTCACGTC
2351  TTTTGGTGGG TGTCCTTGGC TGCTACTGTT ACATGGGTGT AATAGCTGAA.
2401  GAGGAAGCAT ATAAGTCAGA ATTATTCCAG AAAGCCAACT CTCTAATGCA
2451  ATGTGCAGGA GAAAGTATCA CTCTGTTTAA AAATAAGACA AATGAGGAAT
2501  TCAGAATTGG TTCCTTGAGA AATATGATGC AGCTATGTAC ACGTTGCTTG
2551  AGCAACTGTA CCAAGAAGAG TCCAAATAAG ATTGCATCTG GCTTTTTCCT
2601  GCGATTGTTA ACATCAAAGC TAATGAATGA CATTGCAGAT ATTTGTAAAA
2651  GTTTAGCATC CTTCATCAAA AAGCCATTTG ACCGTGGAGA AGTAGAATCA
2701  ATGGAAGATG ATACTAATGG AAATCTAATG GAGGTGGAGG ATCAGTCATC
2751  CATGAATCTA TTTAACGATT ACCCTGATAG TAGTGTTAGT GATGCAAACG
2801  AACCTGGAGA GAGCCAAAGT ACCATAGGTG CCATTAATCC TTTAGCTGAA
2851  GAATATCTGT CAAAGCAAGA TCTACTTTTC TTAGACATGC TCAAGTTCTT
2901  GTGTTTGTGT GTAACTACTG CTCAGACCAA TACTGTGTCC TTTAGGGCAG
2951  CTGATATTCG GAGGAAATTG TTAATGTTAA TTGATTCTAG CACGCTAGAA
3001  CCTACCAAAT CCCTCCACCT GCATATGTAT CTAATGCTTT TAAAGGAGCT
3051  TCCTGGAGAA GAGTACCCCT TGCCAATGGA AGATGTTCTT GAACTTCTGA
3101  AACCACTATC CAATGTGTGT TCTTTGTATC GTCGTGACCA AGATGTTTGT
3151  AAAACTATTT TAAACCATGT CCTTCATGTA GTGAAAAACC TAGGTCAAAG
3201  CAATATGGAC TCTGAGAACA CAAGGGATGC TCAAGGACAG TTTCTTACAG
3251  TAATTGGAGC ATTTTGGCAT CTAACAAAGG AGAGGAAATA TATATTCTCT
3301  GTAAGAATGG CCCTAGTAAA TTGCCTTAAA ACTTTGCTTG AGGCTGATCC
3351  TTATTCAAAA TGGGCCATTC TTAATGTAAT GGGAAAAGAC TTTCCTGTAA
3401  ATGAAGTATT TACACAATTT CTTGCTGACA ATCATCACCA AGTTCGCATG
3451  TTGGCTGCAG AGTCAATCAA TAGATTGTTC CAGGACACGA AGGGAGATTC
3501  TTCCAGGTTA CTGAAAGCAC TTCCTTTGAA GCTTCAGCAA ACAGCTTTTG
```

Figure 6b (iv)

```
3551 AAAATGCATA CTTGAAAGCT CAGGAAGGAA TGAGAGAAAT GTCCCATAGT
3601 GCTGAGAACC CTGAAACTTT GGATGAAATT TATAATAGAA AATCTGTTTT
3651 ACTGACGTTG ATAGCTGTGG TTTTATCCTG TAGCCCTATC TGCGAAAAAC
3701 AGGCTTTGTT TGCCCTGTGT AAATCTGTGA AAGAGAATGG ATTAGAACCT
3751 CACCTTGTGA AAAAGGTTTT AGAGAAAGTT TCTGAAACTT TTGGATATAG
3801 ACGTTTAGAA GACTTTATGG CATCTCATTT AGATTATCTG GTTTTGGAAT
3851 GGCTAAATCT TCAAGATACT GAATACAACT TATCTTCTTT TCCTTTTATT
3901 TTATTAAACT ACACAAATAT TGAGGATTTC TATAGATCTT GTTATAAGGT
3951 TTTGATTCCA CATCTGGTGA TTAGAAGTCA TTTTGATGAG GTGAAGTCCA
4001 TTGCTAATCA GATTCAAGAG GACTGGAAAA GTCTTCTAAC AGACTGCTTT
4051 CCAAAGATTC TTGTAAATAT TCTTCCTTAT TTTGCCTATG AGGGTACCAG
4101 AGACAGTGGG ATGGCACAGC AAAGAGAGAC TGCTACCAAG GTCTATGATA
4151 TGCTTAAAAG TGAAAACTTA TTGGGAAAAC AGATTGATCA CTTATTCATT
4201 AGTAATTTAC CAGAGATTGT GGTGGAGTTA TTGATGACGT TACATGAGCC
4251 AGCAAATTCT AGTGCCAGTC AGAGCACTGA CCTCTGTGAC TTTTCAGGGG
4301 ATTTGGATCC TGCTCCTAAT CCACCTCATT TTCCATCGCA TGTGATTAAA
4351 GCAACATTTG CCTATATCAG CAATTGTCAT AAAACCAAGT TAAAAAGCAT
4401 TTTAGAAATT CTTTCCAAAA GCCCTGATTC CTATCAGAAA ATTCTTCTTG
4451 CCATATGTGA GCAAGCAGCT GAAACAAATA ATGTTTATAA GAAGCACAGA
4501 ATTCTTAAAA TATATCACCT GTTTGTTAGT TTATTACTGA AAGATATAAA
4551 AAGTGGCTTA GGAGGAGCTT GGGCCTTTGT TCTTCGAGAC GTTATTTATA
4601 CTTTGATTCA CTATATCAAC CAAAGGCCTT CTTGTATCAT GGATGTGTCA
4651 TTACGTAGCT TCTCCCTTTG TTGTGACTTA TTAAGTCAGG TTTGCCAGAC
4701 AGCCGTGACT TACTGTAAGG ATGCTCTAGA AAACCATCTT CATGTTATTG
4751 TTGGTACACT TATACCCCTT GTGTATGAGC AGGTGGAGGT TCAGAAACAG
4801 GTATTGGACT TGTTGAAATA CTTAGTGATA GATAACAAGG ATAATGAAAA
4851 CCTCTATATC ACGATTAAGC TTTTAGATCC TTTTCCTGAC CATGTTGTTT
4901 TTAAGGATTT GCGTATTACT CAGCAAAAAA TCAAATACAG TAGAGGACCC
4951 TTTTCACTCT TGGAGGAAAT TAACCATTTT CTCTCAGTAA GTGTTTATGA
5001 TGCACTTCCA TTGACAAGAC TTGAAGGACT AAAGGATCTT CGAAGACAAC
5051 TGGAACTACA TAAAGATCAG ATGGTGGACA TTATGAGAGC TTCTCAGGAT
5101 AATCCGCAAG ATGGGATTAT GGTGAAACTA GTTGTCAATT TGTTGCAGTT
5151 ATCCAAGATG GCAATAAACC ACACTGGTGA AAAAGAAGTT CTAGAGGCTG
5201 TTGGAAGCTG CTTGGGAGAA GTGGGTCCTA TAGATTTCTC TACCATAGCT
```

Figure 6b (v)

```
5251  ATACAACATA GTAAAGATGC ATCTTATACC AAGGCCCTTA AGTTATTTGA
5301  AGATAAAGAA CTTCAGTGGA CCTTCATAAT GCTGACCTAC CTGAATAACA
5351  CACTGGTAGA AGATTGTGTC AAAGTTCGAT CAGCAGCTGT TACCTGTTTG
5401  AAAAACATTT TAGCCACAAA GACTGGACAT AGTTTCTGGG AGATTTATAA
5451  GATGACAACA GATCCAATGC TGGCCTATCT ACAGCCTTTT AGAACATCAA
5501  GAAAAAAGTT TTTAGAAGTA CCCAGATTTG ACAAGAAAA CCCTTTTGAA
5551  GGCCTGGATG ATATAAATCT GTGGATTCCT CTAAGTGAAA ATCATGACAT
5601  TTGGATAAAG ACACTGACTT GTGCTTTTTT GGACAGTGGA GGCACAAAAT
5651  GTGAAATTCT TCAATTATTA AAGCCAATGT GTGAAGTGAA AACTGACTTT
5701  TGTCAGACTG TACTTCCATA CTTGATTCAT GATATTTTAC TCCAAGATAC
5751  AAATGAATCA TGGAGAAATC TGCTTTCTAC ACATGTTCAG GGATTTTTCA
5801  CCAGCTGTCT TCGACACTTC TCGCAAACGA GCCGATCCAC AACCCCTGCA
5851  AACTTGGATT CAGAGTCAGA GCACTTTTTC CGATGCTGTT TGGATAAAAA
5901  ATCACAAAGA ACAATGCTTG CTGTTGTGGA CTACATGAGA AGACAAAAGA
5951  GACCTTCTTC AGGAACAATT TTTAATGATG CTTTCTGGCT GGATTTAAAT
6001  TATCTAGAAG TTGCCAAGGT AGCTCAGTCT TGTGCTGCTC ACTTTACAGC
6051  TTTACTCTAT GCAGAAATCT ATGCAGATAA GAAAAGTATG GATGATCAAG
6101  AGAAAAGAAG TCTTGCATTT GAAGAAGGAA GCCAGAGTAC AACTATTTCT
6151  AGCTTGAGTG AAAAAAGTAA AGAAGAAACT GGAATAAGTT TACAGGATCT
6201  TCTCTTAGAA ATCTACAGAA GTATAGGGGA GCCAGATAGT TTGTATGGCT
6251  GTGGTGGAGG GAAGATGTTA CAACCCATTA CTAGACTACG AACATATGAA
6301  CACGAAGCAA TGTGGGGCAA AGCCCTAGTA ACATATGACC TCAAACAGC
6351  AATCCCCTCA TCAACACGCC AGGCAGGAAT CATTCAGGCC TTGCAGAATT
6401  TGGGACTCTG CCATATTCTT TCCGTCTATT TAAAAGGATT GGATTATGAA
6451  AATAAAGACT GGTGTCCTGA ACTAGAAGAA CTTCATTACC AAGCAGCATG
6501  GAGGAATATG CAGTGGGACC ATTGCACTTC CGTCAGCAAA GAAGTAGAAG
6551  GAACCAGTTA CCATGAATCA TTGTACAATG CTCTACAATC TCTAAGAGAC
6601  AGAGAATTCT CTACATTTTA TGAAAGTCTC AAATATGCCA GAGTAAAAGA
6651  AGTGGAAGAG ATGTGTAAGC GCAGCCTTGA GTCTGTGTAT TCGCTCTATC
6701  CCACACTTAG CAGGTTGCAG GCCATTGGAG AGCTGGAAAG CATTGGGGAG
6751  CTTTTCTCAA GATCAGTCAC ACATAGACAA CTCTCTGAAG TATATATTAA
6801  GTGGCAGAAA CACTCCCAGC TTCTCAAGGA CAGTGATTTT AGTTTTCAGG
6851  AGCCTATCAT GGCTCTACGC ACAGTCATTT TGGAGATCCT GATGGAAAAG
```

Figure 6b (vi)

```
6901  GAAATGGACA ACTCACAAAG AGAATGTATT AAGGACATTC TCACCAAACA
6951  CCTTGTAGAA CTCTCTATAC TGGCCAGAAC TTTCAAGAAC ACTCAGCTCC
7001  CTGAAAGGGC AATATTTCAA ATTAAACAGT ACAATTCAGT TAGCTGTGGA
7051  GTCTCTGAGT GGCAGCTGGA AGAAGCACAA GTATTCTGGG CAAAAAAGGA
7101  GCAGAGTCTT GCCCTGAGTA TTCTCAAGCA AATGATCAAG AAGTTGGATG
7151  CCAGCTGTGC AGCGAACAAT CCCAGCCTAA AACTTACATA CACAGAATGT
7201  CTGAGGGTTT GTGGCAACTG GTTAGCAGAA ACGTGCTTAG AAAATCCTGC
7251  GGTCATCATG CAGACCTATC TAGAAAAGGC AGTAGAAGTT GCTGGAAATT
7301  ATGATGGAGA AAGTAGTGAT GAGCTAAGAA ATGGAAAAAT GAAGGCATTT
7351  CTCTCATTAG CCCGGTTTTC AGATACTCAA TACCAAAGAA TTGAAAACTA
7401  CATGAAATCA TCGGAATTTG AAAACAAGCA AGCTCTCCTG AAAAGAGCCA
7451  AAGAGGAAGT AGGTCTCCTT AGGGAACATA AAATTCAGAC AAACAGATAC
7501  ACAGTAAAGG TTCAGCGAGA GCTGGAGTTG GATGAATTAG CCCTGCGTGC
7551  ACTGAAAGAG GATCGTAAAC GCTTCTTATG TAAAGCAGTT GAAAATTATA
7601  TCAACTGCTT ATTAAGTGGA GAAGAACATG ATATGTGGGT ATTCCGGCTT
7651  TGTTCCCTCT GGCTTGAAAA TTCTGGAGTT TCTGAAGTCA ATGGCATGAT
7701  GAAGAGAGAC GGAATGAAGA TTCCAACATA TAAATTTTTG CCTCTTATGT
7751  ACCAATTGGC TGCTAGAATG GGACCAAGA TGATGGGAGG CCTAGGATTT
7801  CATGAAGTCC TCAATAATCT AATCTCTAGA ATTTCAATGG ATCACCCCCA
7851  TCACACTTTG TTTATTATAC TGGCCTTAGC AAATGCAAAC AGAGATGAAT
7901  TTCTGACTAA ACCAGAGGTA GCCAGAAGAA GCAGAATAAC TAAAAATGTG
7951  CCTAAACAAA GCTCTCAGCT TGATGAGGAT CGAACAGAGG CTGCAAATAG
8001  AATAATATGT ACTATCAGAA GTAGGAGACC TCAGATGGTC AGAAGTGTTG
8051  AGGCACTTTG TGATGCTTAT ATTATATTAG CAAACTTAGA TGCCACTCAG
8101  TGGAAGACTC AGAGAAAGG CATAAATATT CCAGCAGACC AGCCAATTAC
8151  TAAACTTAAG AATTTAGAAG ATGTTGTTGT CCCTACTATG GAAATTAAGG
8201  TGGACCACAC AGGAGAATAT GGAAATCTGG TGACTATACA GTCATTTAAA
8251  GCAGAATTTC GCTTAGCAGG AGGTGTAAAT TTACCAAAAA TAATAGATTG
8301  TGTAGGTTCC GATGGCAAGG AGAGGAGACA GCTTGTTAAG GGCCGTGATG
8351  ACCTGAGACA AGATGCTGTC ATGCAACAGG TCTTCCAGAT GTGTAATACA
8401  TTACTGCAGA GAAACACGGA AACTAGGAAG AGGAAATTAA CTATCTGTAC
8451  TTATAAGGTG GTTCCCCTCT CTCAGCGAAG TGGTGTTCTT GAATGGTGCA
8501  CAGGAACTGT CCCCATTGGT GAATTTCTTG TTAACAATGA AGATGGTGCT
8551  CATAAAAGAT ACAGGCCAAA TGATTTCAGT GCCTTTCAGT GCCAAAAGAA
```

Figure 6b (vii)

```
8601  AATGATGGAG GTGCAAAAAA AGTCTTTTGA AGAGAAATAT GAAGTCTTCA
8651  TGGATGTTTG CCAAAATTTT CAACCAGTTT TCCGTTACTT CTGCATGGAA
8701  AAATTCTTGG ATCCAGCTAT TTGGTTTGAG AAGCGATTGG CTTATACGCG
8751  CAGTGTAGCT ACTTCTTCTA TTGTTGGTTA CATACTTGGA CTTGGTGATA
8801  GACATGTACA GAATATCTTG ATAAATGAGC AGTCAGCAGA ACTTGTACAT
8851  ATAGATCTAG GTGTTGCTTT TGAACAGGGC AAAATCCTTC CTACTCCTGA
8901  GACAGTTCCT TTTAGACTCA CCAGAGATAT TGTGGATGGC ATGGGCATTA
8951  CGGGTGTTGA AGGTGTCTTC AGAAGATGCT GTGAGAAAAC CATGGAAGTG
9001  ATGAGAAACT CTCAGGAAAC TCTGTTAACC ATTGTAGAGG TCCTTCTATA
9051  TGATCCACTC TTTGACTGGA CCATGAATCC TTTGAAAGCT TTGTATTTAC
9101  AGCAGAGGCC GGAAGATGAA ACTGAGCTTC ACCCTACTCT GAATGCAGAT
9151  GACCAAGAAT GCAAACGAAA TCTCAGTGAT ATTGACCAGA GTTTCGACAA
9201  AGTAGCTGAA CGTGTCTTAA TGAGACTACA AGAGAAACTG AAAGGAGTGG
9251  AAGAAGGCAC TGTGCTCAGT GTTGGTGGAC AGGTGAATTT GCTCATACAG
9301  CAGGCCATAG ACCCCAAAAA TCTCAGCCGA CTTTTCCCAG GATGGAAAGC
9351  TTGGGTGTGA TCTTCAGTAT ATGAATTACC CTTTC
```

Figure 7a

```
XX
FH      Key             Location/Qualifiers
FH
FT      source          1..1303
FT                      /organism="Homo sapiens"
FT      CDS             122..1303
FT                      /codon_start=1
FT                      /db_xref="PID:g339816"
FT                      /db_xref="SWISS-PROT:P04637"
FT                      /note="p53 antigen; NCBI gi: 339816"
FT                      /gene="TP53"
FT                      /map="17p13.1"
FT                      /translation="MEEPQSDPSVEPPLSQETFSDLWKLLPENNVLSPLPSQAMDDLML
FT                      SPDDIEQWFTEDPGPDEAPRMPEAAPPVAPAPATPTPAAPAPAPSWPLSSSVPSQKTYQ
FT                      GSYGFRLGFLHSGTAKSVTCTYSPALNKMFCQLAKTCPVQLWVDSTPPPGTRVRAMAIY
FT                      KQSQHMTEVVRRCPHHERCSDSDGLAPPQHLIRVEGNLRVEYLDDRNTFRHSVVVPYEP
FT                      PEVGSDCTTIHYNYMCNSSCMGGMNRRPILTIITLEDSSGNLLGRNSFEVRVCACPGRD
FT                      RRTEEENLRKKGEPHHELPPGSTKRALPNNTSSSPQPKKKPLDGEYFTLQIRGRERFEM
FT                      FRELNEALELKDAQAGKEPGGSRAHSSHLKSKKGQSTSRHKKLMFKTEGPDSD"
XX
SQ      Sequence 1303 BP; 292 A; 403 C; 348 G; 260 T; 0 other;

M14695  Length: 1303  July 10, 1998 12:29  Type: N  Check: 4902

1  GTCCAGGAGC AGGTAGCTGC TGGGCTCCGG GGACACTTTG CGTTCGGGCT

51  GGGAGCGTGC TTTCCACGAC GGTGACACGC TTCCCTGGAT TGGCAGCCAG

101  ACTGCCTTCC GGGTCACTGC CATGGAGGAG CCGCAGTCAG ATCCTAGCGT

151  CGAGCCCCCT CTGAGTCAGG AAACATTTTC AGACCTATGG AAACTACTTC

201  CTGAAAACAA CGTTCTGTCC CCCTTGCCGT CCCAAGCAAT GGATGATTTG

251  ATGCTGTCCC CGGACGATAT TGAACAATGG TTCACTGAAG ACCCAGGTCC
```

```
 301  AGATGAAGCT CCCAGAATGC CAGAGGCTGC TCCCCCCGTG GCCCCTGCAC
 351  CAGCGACTCC TACACCGGCG GCCCCTGCAC CAGCCCCCTC CTGGCCCCTG
 401  TCATCTTCTG TCCCTTCCCA GAAAACCTAC CAGGGCAGCT ACGGTTTCCG
 451  TCTGGGCTTC TTGCATTCTG GGACAGCCAA GTCTGTGACT TGCACGTACT
 501  CCCCTGCCCT CAACAAGATG TTTTGCCAAC TGGCCAAGAC CTGCCCTGTG
 551  CAGCTGTGGG TTGATTCCAC ACCCCGCCC GGCACCGCG TCCGCGCCAT
 601  GGCCATCTAC AAGCAGTCAC AGCACATGAC GGAGGTTGTG AGGCGCTGCC
 651  CCCACCATGA GCGCTGCTCA GATAGCGATG GTCTGGCCCC TCCTCAGCAT
 701  CTTATCCGAG TGGAAGGAAA TTTGCGTGTG GAGTATTTGG ATGACAGAAA
 751  CACTTTTCGA CATAGTGTGG TGGTGCCCTA TGAGCCGCCT GAGGTTGGCT
 801  CTGACTGTAC CACCATCCAC TACAACTACA TGTGTAACAG TTCCTGCATG
 851  GGCGGCATGA ACCGGAGGCC CATCCTCACC ATCATCACAC TGGAAGACTC
 901  CAGTGGTAAT CTACTGGGAC GGAACAGCTT TGAGGTGCGT GTTTGTGCCT
 951  GTCCTGGGAG AGACCGGCGC ACAGAGGAAG AGAATCTCCG CAAGAAAGGG
1001  GAGCCTCACC ACGAGCTGCC CCCAGGGAGC ACTAAGCGAG CACTGCCCAA
1051  CAACACCAGC TCCTCTCCCC AGCCAAAGAA GAAACCACTG GATGGAGAAT
1101  ATTTCACCCT TCAGATCCGT GGGCGTGAGC GCTTCGAGAT GTTCCGAGAG
1151  CTGAATGAGG CCTTGGAACT CAAGGATGCC CAGGCTGGGA AGGAGCCAGG
1201  GGGGAGCAGG GCTCACTCCA GCCACCTGAA GTCCAAAAAG GGTCAGTCTA
1251  CCTCCCGCCA TAAAAAACTC ATGTTCAAGA CAGAAGGGCC TGACTCAGAC
1301  TGA
```

Figure 8a (i)

```
!!NA_SEQUENCE 1.0
ID   HS498441    standard; RNA; HUM; 8210 BP.
XX
AC   U49844;
XX
NI   g1235901
XX
DT   20-MAY-1996 (Rel. 47, Created)
DT   20-MAY-1996 (Rel. 47, Last updated, Version 1)
XX
DE   Human FRAP-related protein (FRP1) mRNA, complete cds.
XX
KW
XX
OS   Homo sapiens (human)
OC   Eukaryota; Metazoa; Chordata; Vertebrata; Mammalia; Eutheria; Primates;
OC   Catarrhini; Hominidae; Homo.
XX
RN   [1]
RP   1-8210
RA   Cimprich K.A., Shin T.B., Keith C.T., Schreiber S.L.;
RT   "cDNA cloning and gene mapping of a candidate human cell cycle
RT   checkpoint protein";
RL   Proc. Natl. Acad. Sci. U.S.A. 93:2850-2855(1996).
XX
RN   [2]
RP   1-8210
RA   Cimprich K.A., Shin T.B., Keith C.T., Schreiber S.L.;
RT   ;
RL   Submitted (22-FEB-1996) to the EMBL/GenBank/DDBJ databases.
RL   Karlene A. Cimprich, Chemistry, Harvard University, 12 Oxford Street,
RL   Cambridge, MA 02138, USA
XX
DR   SPTREMBL; Q13535; Q13535.
XX
FH   Key             Location/Qualifiers
FH
FT   source          1..8210
FT                   /organism="Homo sapiens"
FT                   /chromosome="3"
FT                   /cell_type="Jurkat T-cell"
FT                   /map="3q22-q24"
FT   CDS             106..8040
FT                   /codon_start=1
FT                   /db_xref="PID:g1235902"
FT                   /db_xref="SPTREMBL:Q13535"
FT                   /note="similar to FRAP, Meclp, Torlp, Tor2p, and ATM"
FT                   /gene="FRP1"  or ATR
FT                   /product="FRAP-related protein"
FT                   /translation="MGEHGLELASMIPALRELGSATPEEYNTVVQKPRQILCQFIDRIL
FT                   TDVNVVAVELVKKTDSQPTSVMLLDFIQHIMKSSPLMFVNVSGSHEAKGSCIEFSNWII
FT                   TRLLRIAATPSCHLLHKKICEVICSLLFLFKSKSPAIFGVLTKELLQLFEDLVYLHRRN
FT                   VMGHAVEWPVVMSRFLSQLDEHMGYLQSAPLQLMSMQNLEFIEVTLLMVLTRIIAIVFF
FT                   RRQELLLWQIGCVLLEYGSPKIKSLAISFLTELFQLGGLPAQPASTFFSSFLELLKHLV
FT                   EMDTDQLKLYEEPLSKLIKTLFPFEAEAYRNIEPVYLNMLLEKLCVMFEDGVLMRLKSD
FT                   LLKAALCHLLQYFLKFVPAGYESALQVRKVYVRNICKALLDVLGIEVDAEYLLGPLYAA
FT                   LKMESMEIIEEIQCQTQQENLSSNSDGISPKRRRLSSSLNPSKRAPKQTEEIKHVDMNQ
FT                   KSILWSALKQKAESLQISLEYSGLKNPVIEMLEGIAVVLQLTALCTVHCSHQNMNCRTF
FT                   KDCQHKSKKKPSVVITWMSLDFYTKVLKSCRSLLESVQKLDLEATIDKVVKIYDALIYM
FT                   QVNSSFEDHILEDLCGMLSLPWIYSHSDDGCLKLTTFAANLLTLSCRISDSYSPQAQSR
FT                   CVFLLTLFPRRIFLEWRTAVYNWALQSSHEVIRASCVSGFFILLQQQNSCNRVPKILID
FT                   KVKDDSDIVKKEFASILGQLVCTLHGMFYLTSSLTEPFSEHGHVDLFCRNLKATSQHEC
FT                   SSSQLKASVCKPFLFLLKKKIPSPVKLAFIDNLHHLCKHLDFREDETDVKAVLGTLLNL
FT                   MEDPDKDVRVAFSGNIKHILESLDSEDGFIKELFVLRMKEAYTHAQISRNNELKDTLIL
FT                   TTGDIGRAAKGDLVPFALLHLLHCLLSKSASVSGAAYTEIRALVAAKSVKLQSFFSQYK
FT                   KPICQFLVESLHSSQMTALPNTPCQNADVRKQDVAHQREMALNTLSEIANVFDFPDLNR
FT                   FLTRTLQVLLPDLAAKASPAASALIRTLGKQLNVNRREILINNFKYIFSHLVCSCSKDE
```

Figure 8a (ii)

```
FT            LERALHYLKNETEIELGSLLRQDFQGLHNELLLRIGEHYQQVFNGLSILASFASSDDPY
FT            QGPRDIISPELMADYLQPKLLGILAFFNMQLLSSSVGIEDKKMALNSLMSLMKLMGPKH
FT            VSSVRVKMMTTLRTGLRFKDDFPELCCRAWDCFVRCLDHACLGSLLSHVIVALLPLIHI
FT            QPKETAAIFHYLIIENRDAVQDFLHEIYFLPDHPELKKIKAVLQEYRKETSESTDLQTT
FT            LQLSMKAIQHENVDVRIHALTSLKETLYKNQEKLIKYATDSETVEPIISQLVTVLLKGC
FT            QDANSQARLLCGECLGELGAIDPGRLDFSTTETQGKDFTFVTGVEDSSFAYGLLMELTR
FT            AYLAYADNSRAQDSAAYAIQELLSIYDCREMETNGPGHQLWRRFPEHVREILEPHLNTR
FT            YKSSQKSTDWSGVKKPIYLSKLGSNFAEWSASWAGYLITKVRHDLASKIFTCCSIMMKH
FT            DFKVTIYLLPHILVYVLLGCNQEDQQEVYAEIMAVLKHDDQHTINTQDIASDLCQLSTQ
FT            TVFSMLDHLTQWARHKFQALKAEKCPHSKSNRNKVDSMVSTVDYEDYQSVTRFLDLIPQ
FT            DTLAVASFRSKAYTRAVMHFESFITEKKQNIQEHLGFLQKLYAAMHEPDGVAGVSAIRK
FT            AEPSLKEQILEHESLGLLRDATACYDRAIQLEPDQIIHYHGVVKSMLGLGQLSTVITQV
FT            NGVHANRSEWTDELNTYRVEAAWKLSQWDLVENYLAADGKSTTWSVRLGQLLLSAKKRD
FT            ITAFYDSLKLVRAEQIVPLSAASFERGSYQRGYEYIVRLHMLCELEHSIKPLFQHSPGD
FT            SSQEDSLNWVARLEMTQNSYRAKEPILALRRALLSLNKRPDYNEMVGECWLQSARVARK
FT            AGHHQTAYNALLNAGESRLAELYVERAKWLWSKGDVHQALIVLQKGVELCFPENETPPE
FT            GKNMLIHGRAMLLVGRFMEETANFESNAIMKKYKDVTACLPEWEDGHFYLAKYYDKLMP
FT            MVTDNKMEKQGDLIRYIVLHFGRSLQYGNQFIYQSMPRMLTLWLDYGTKAYEWEKAGRS
FT            DRVQMRNDLGKINKVITEHTNYLAPYQFLTAFSQLISRICHSHDEVFVVLMEIIAKVFL
FT            AYPQQAMWMMTAVSKSSYPMRVNRCKEILNKAIHMKKSLEKFVGDATRLTDKLLELGNK
FT            PVDGSSSTLSMSTHFKMLKKLVEEATFSEILIPLQSVMIPTLPSILGTHANHASHEPFP
FT            GHWAYIAGFDDMVEILASLQKPKKISLKGSDGKFYIMMCKPKDDLRKDCRLMEFNSLIN
FT            KCLRKDAESRRRELHIRTYAVIPLNDECGIIEWVNNTAGLRPILTKLYKEKGVYMTGKE
FT            LRQCMLPKSAALSEKLKVFREFLLPRHPPIFHEWFLRTFPDPTSWYSSRSAYCRSTAVM
FT            SMVGYILGLGDRHGENILFDSLTGECVHVDFNCLFNKGETFEVPEIVPFRLTHNMVNGM
FT            GPMGTEGLFRRACEVTMRLMRDQREPLMSVLKTFLHDPLVEWSKPVKGHSKAPLNETGE
FT            VVNEKAKTHVLDIEQRLQGVIKTRNRVTGLPLSIEGHVHYLIQEATDENLLCQMYLGWT
FT            PYM*
XX
SQ   Sequence 8210 BP; 2511 A; 1555 C; 1738 G; 2406 T; 0 other;

U49844   Length: 8210  July 10, 1998 12:08  Type: N  Check: 4511

1  GCCTCCACAC  GGCTCCGTCG  GGCGCCGCGC  TCTTCCGGCA  GCGGTAGCTT
    51  TGGAGACGCC  GGGAACCCGC  GTTGGCGTGG  TTGACTAGTG  CCTCGCAGCC
   101  TCAGCATGGG  GGAACATGGC  CTGGAGCTGG  CTTCCATGAT  CCCCGCCCTG
   151  CGGGAGCTGG  GCAGTGCCAC  ACCAGAGGAA  TATAATACAG  TTGTACAGAA
   201  GCCAAGACAA  ATTCTGTGTC  AATTCATTGA  CCGGATACTT  ACAGATGTAA
   251  ATGTTGTTGC  TGTAGAACTT  GTAAAGAAAA  CTGACTCTCA  GCCAACCTCC
   301  GTGATGTTGC  TTGATTTCAT  CCAGCATATC  ATGAAATCCT  CCCCACTTAT
   351  GTTTGTAAAT  GTGAGTGGAA  GCCATGAGGC  CAAAGGCAGT  TGTATTGAAT
   401  TCAGTAATTG  GATCATAACG  AGACTTCTGC  GGATTGCAGC  AACTCCCTCC
   451  TGTCATTTGT  TACACAAGAA  AATCTGTGAA  GTCATCTGTT  CATTATTATT
   501  TCTTTTTAAA  AGCAAGAGTC  CTGCTATTTT  TGGGGTACTC  ACAAAAGAAT
   551  TATTACAACT  TTTTGAAGAC  TTGGTTTACC  TCCATAGAAG  AAATGTGATG
   601  GGTCATGCTG  TGGAATGGCC  AGTGGTCATG  AGCCGATTTT  TAAGTCAATT
   651  AGATGAACAC  ATGGGATATT  TACAATCAGC  TCCTTTGCAG  TTGATGAGTA
   701  TGCAAAATTT  AGAATTTATT  GAAGTCACTT  TATTAATGGT  TCTTACTCGT
   751  ATTATTGCAA  TTGTGTTTTT  TAGAAGGCAA  GAACTCTTAC  TTTGGCAGAT
   801  AGGTTGTGTT  CTGCTAGAGT  ATGGTAGTCC  AAAAATTAAA  TCCCTAGCAA
```

```
 851  TTAGCTTTTT AACAGAACTT TTTCAGCTTG GAGGACTACC AGCACAACCA
 901  GCTAGCACTT TTTTCAGCTC ATTTTTGGAA TTATTAAAAC ACCTTGTAGA
 951  AATGGATACT GACCAATTGA AACTCTATGA AGAGCCATTA TCAAAGCTGA
1001  TAAAGACACT ATTTCCCTTT GAAGCAGAAG CTTATAGAAA TATTGAACCT
1051  GTCTATTTAA ATATGCTGCT GGAAAAACTC TGTGTCATGT TTGAAGACGG
1101  TGTGCTCATG CGGCTTAAGT CTGATTTGCT AAAAGCAGCT TTGTGCCATT
1151  TACTGCAGTA TTTCCTTAAA TTTGTGCCAG CTGGGTATGA ATCTGCTTTA
1201  CAAGTCAGGA AGGTCTATGT GAGAAATATT TGTAAAGCTC TTTTGGATGT
1251  GCTTGGAATT GAGGTAGATG CAGAGTACTT GTTGGGCCCA CTTTATGCAG
1301  CTTTGAAAAT GGAAAGTATG GAAATCATTG AGGAGATTCA ATGCCAAACT
1351  CAACAGGAAA ACCTCAGCAG TAATAGTGAT GGAATATCAC CCAAAAGGCG
1401  TCGTCTCAGC TCGTCTCTAA ACCCTTCTAA AAGAGCACCA AAACAGACTG
1451  AGGAAATTAA ACATGTGGAC ATGAACCAAA AGAGCATATT ATGGAGTGCA
1501  CTGAAACAGA AAGCTGAATC CCTTCAGATT TCCCTTGAAT ACAGTGGCCT
1551  AAAGAATCCT GTTATTGAGA TGTTAGAAGG AATTGCTGTT GTCTTACAAC
1601  TGACTGCTCT GTGTACTGTT CATTGTTCTC ATCAAAACAT GAACTGCCGT
1651  ACTTTCAAGG ACTGTCAACA TAAATCCAAG AAGAAACCTT CTGTAGTGAT
1701  AACTTGGATG TCATTGGATT TTTACACAAA AGTGCTTAAG AGCTGTAGAA
1751  GTTTGTTAGA ATCTGTTCAG AAACTGGACC TGGAGGCAAC CATTGATAAG
1801  GTGGTGAAAA TTTATGATGC TTTGATTTAT ATGCAAGTAA ACAGTTCATT
1851  TGAAGATCAT ATCCTGGAAG ATTTATGTGG TATGCTCTCA CTTCCATGGA
1901  TTTATTCCCA TTCTGATGAT GGCTGTTTAA AGTTGACCAC ATTTGCCGCT
1951  AATCTTCTAA CATTAAGCTG TAGGATTTCA GATAGCTATT CACCACAGGC
2001  ACAATCACGA TGTGTGTTTC TTCTGACTCT GTTTCCAAGA AGAATATTCC
2051  TTGAGTGGAG AACAGCAGTT TACAACTGGG CCCTGCAGAG CTCCCATGAA
2101  GTAATCCGGG CTAGTTGTGT TAGTGGATTT TTTATCTTAT TGCAGCAGCA
2151  GAATTCTTGT AACAGAGTTC CCAAGATTCT TATAGATAAA GTCAAAGATG
2201  ATTCTGACAT TGTCAAGAAA GAATTTGCTT CTATACTTGG TCAACTTGTC
2251  TGTACTCTTC ACGGCATGTT TTATCTGACA AGTTCTTTAA CAGAACCTTT
2301  CTCTGAACAC GGACATGTGG ACCTCTTCTG TAGGAACTTG AAAGCCACTT
2351  CTCAACATGA ATGTTCATCT TCTCAACTAA AAGCTTCTGT CTGCAAGCCA
2401  TTCCTTTTCC TACTGAAAAA AAAAATACCT AGTCCAGTAA AACTTGCTTT
2451  CATAGATAAT CTACATCATC TTTGTAAGCA TCTTGATTTT AGAGAAGATG
2501  AAACAGATGT AAAAGCAGTT CTTGGAACTT TATTAAATTT AATGGAAGAT
```

Figure 8b (iii)

```
2551  CCAGACAAAG ATGTTAGAGT GGCTTTTAGT GGAAATATCA AGCACATATT
2601  GGAATCCTTG GACTCTGAAG ATGGATTTAT AAAGGAGCTT TTTGTCTTAA
2651  GAATGAAGGA AGCATATACA CATGCCCAAA TATCAAGAAA TAATGAGCTG
2701  AAGGATACCT TGATTCTTAC AACAGGGGAT ATTGGAAGGG CCGCAAAAGG
2751  AGATTTGGTA CCATTTGCAC TCTTACACTT ATTGCATTGT TTGTTATCCA
2801  AGTCAGCATC TGTCTCTGGA GCAGCATACA CAGAAATTAG AGCTCTGGTT
2851  GCAGCTAAAA GTGTTAAACT GCAAAGTTTT TTCAGCCAGT ATAAGAAACC
2901  CATCTGTCAG TTTTTGGTAG AATCCCTTCA CTCTAGTCAG ATGACAGCAC
2951  TTCCGAATAC TCCATGCCAG AATGCTGACG TGCGAAAACA AGATGTGGCT
3001  CACCAGAGAG AAATGGCTTT AAATACGTTG TCTGAAATTG CCAACGTTTT
3051  CGACTTTCCT GATCTTAATC GTTTTCTTAC TAGGACATTA CAAGTTCTAC
3101  TACCTGATCT TGCTGCCAAA GCAAGCCCTG CAGCTTCTGC TCTCATTCGA
3151  ACTTTAGGAA AACAATTAAA TGTCAATCGT AGAGAGATTT TAATAAACAA
3201  CTTCAAATAT ATTTTTTCTC ATTTGGTCTG TTCTTGTTCC AAAGATGAAT
3251  TAGAACGTGC CCTTCATTAT CTGAAGAATG AAACAGAAAT TGAACTGGGG
3301  AGCCTGTTGA GACAAGATTT CCAAGGATTG CATAATGAAT TATTGCTGCG
3351  TATTGGAGAA CACTATCAAC AGGTTTTTAA TGGTTTGTCA ATACTTGCCT
3401  CATTTGCATC CAGTGATGAT CCATATCAGG GCCCGAGAGA TATCATATCA
3451  CCTGAACTGA TGGCTGATTA TTTACAACCC AAATTGTTGG GCATTTTGGC
3501  TTTTTTTAAC ATGCAGTTAC TGAGCTCTAG TGTTGGCATT GAAGATAAGA
3551  AAATGGCCTT GAACAGTTTG ATGTCTTTGA TGAAGTTAAT GGGACCCAAA
3601  CATGTCAGTT CTGTGAGGGT GAAGATGATG ACCACACTGA GAACTGGCCT
3651  TCGATTCAAG GATGATTTTC CTGAATTGTG TTGCAGAGCT TGGGACTGCT
3701  TTGTTCGCTG CCTGGATCAT GCTTGTCTGG GCTCCCTTCT CAGTCATGTA
3751  ATAGTAGCTT TGTTACCTCT TATACACATC CAGCCTAAAG AAACTGCAGC
3801  TATCTTCCAC TACCTCATAA TTGAAAACAG GGATGCTGTG CAAGATTTTC
3851  TTCATGAAAT ATATTTTTTA CCTGATCATC CAGAATTAAA AAAGATAAAA
3901  GCCGTTCTCC AGGAATACAG AAAGGAGACC TCTGAGAGCA CTGATCTTCA
3951  GACAACTCTT CAGCTCTCTA TGAAGGCCAT TCAACATGAA AATGTCGATG
4001  TTCGTATTCA TGCTCTTACA AGCTTGAAGG AAACCTTGTA TAAAAATCAG
4051  GAAAAACTGA TAAAGTATGC AACAGACAGT GAAACAGTAG AACCTATTAT
4101  CTCACAGTTG GTGACAGTGC TTTTGAAAGG TTGCCAAGAT GCAAACTCTC
4151  AAGCTCGGTT GCTCTGTGGG GAATGTTTAG GGAATTGGG GGCGATAGAT
```

Figure 8b (iv)

```
4201  CCAGGTCGAT TAGATTTCTC AACAACTGAA ACTCAAGGAA AAGATTTTAC
4251  ATTTGTGACT GGAGTAGAAG ATTCAAGCTT TGCCTATGGA TTATTGATGG
4301  AGCTAACAAG AGCTTACCTT GCGTACGCTG ATAATAGCCG AGCTCAAGAT
4351  TCAGCTGCCT ATGCCATTCA GGAGTTGCTT TCTATTTATG ACTGTAGAGA
4401  GATGGAGACC AACGGCCCAG GTCACCAATT GTGGAGGAGA TTTCCTGAGC
4451  ATGTTCGGGA AATACTAGAA CCTCATCTAA ATACCAGATA CAAGAGTTCT
4501  CAGAAGTCAA CCGATTGGTC TGGAGTAAAG AAGCCAATTT ACTTAAGTAA
4551  ATTGGGTAGT AACTTTGCAG AATGGTCAGC ATCTTGGGCA GGTTATCTTA
4601  TTACAAAGGT TCGACATGAT CTTGCCAGTA AAATTTTCAC CTGCTGTAGC
4651  ATTATGATGA AGCATGATTT CAAAGTGACC ATCTATCTTC TTCCACATAT
4701  TCTGGTGTAT GTCTTACTGG GTTGTAATCA AGAAGATCAG CAGGAGGTTT
4751  ATGCAGAAAT TATGGCAGTT CTAAAGCATG ACGATCAGCA TACCATAAAT
4801  ACCCAAGACA TTGCATCTGA TCTGTGTCAA CTCAGTACAC AGACTGTGTT
4851  CTCCATGCTT GACCATCTCA CACAGTGGGC AAGGCACAAA TTTCAGGCAC
4901  TGAAAGCTGA GAAATGTCCA CACAGCAAAT CAAACAGAAA TAAGGTAGAC
4951  TCAATGGTAT CTACTGTGGA TTATGAAGAC TATCAGAGTG TAACCCGTTT
5001  TCTAGACCTC ATACCCCAGG ATACTCTGGC AGTAGCTTCC TTTCGCTCCA
5051  AAGCATACAC ACGAGCTGTA ATGCACTTTG AATCATTTAT TACAGAAAAG
5101  AAGCAAAATA TTCAGGAACA TCTTGGATTT TTACAGAAAT TGTATGCTGC
5151  TATGCATGAA CCTGATGGAG TGGCCGGAGT CAGTGCAATT AGAAAGGCAG
5201  AACCATCTCT AAAAGAACAG ATCCTTGAAC ATGAAAGCCT TGGCTTGCTG
5251  AGGGATGCCA CTGCTTGTTA TGACAGGGCT ATTCAGCTAG AACCAGACCA
5301  GATCATTCAT TATCATGGTG TAGTAAAGTC CATGTTAGGT CTTGGTCAGC
5351  TGTCTACTGT TATCACTCAG GTGAATGGAG TGCATGCTAA CAGGTCCGAG
5401  TGGACAGATG AATTAAACAC GTACAGAGTG GAAGCAGCTT GGAAATTGTC
5451  ACAGTGGGAT TTGGTGGAAA ACTATTTGGC AGCAGATGGA AAATCTACAA
5501  CATGGAGTGT CAGACTGGGA CAGCTATTAT TATCAGCCAA AAAAAGAGAT
5551  ATCACAGCTT TTTATGACTC ACTGAAACTA GTGAGAGCAG AACAAATTGT
5601  ACCTCTTTCA GCTGCAAGCT TGAAAGAGG CTCCTACCAA CGAGGATATG
5651  AATATATTGT GAGATTGCAC ATGTTATGTG AGTTGGAGCA TAGCATCAAA
5701  CCACTTTTCC AGCATTCTCC AGGTGACAGT TCTCAAGAAG ATTCTCTAAA
5751  CTGGGTAGCT CGACTAGAAA TGACCCAGAA TTCCTACAGA GCCAAGGAGC
5801  CTATCCTGGC TCTCGGAGG GCTTTACTAA GCCTCAACAA AAGACCAGAT
5851  TACAATGAAA TGGTTGGAGA ATGCTGGCTG CAGAGTGCCA GGGTAGCTAG
```

Figure 8b (v)

```
5901  AAAGGCTGGT CACCACCAGA CAGCCTACAA TGCTCTCCTT AATGCAGGGG
5951  AATCACGACT CGCTGAACTG TACGTGGAAA GGGCAAAGTG GCTCTGGTCC
6001  AAGGGTGATG TTCACCAGGC ACTAATTGTT CTTCAAAAAG GTGTTGAATT
6051  ATGTTTTCCT GAAAATGAAA CCCCACCTGA GGGTAAGAAC ATGTTAATCC
6101  ATGGTCGAGC TATGCTACTA GTGGGCCGAT TTATGGAAGA AACAGCTAAC
6151  TTTGAAAGCA ATGCAATTAT GAAAAAATAT AAGGATGTGA CCGCGTGCCT
6201  GCCAGAATGG GAGGATGGGC ATTTTTACCT TGCCAAGTAC TATGACAAAT
6251  TGATGCCCAT GGTCACAGAC AACAAAATGG AAAAGCAAGG TGATCTCATC
6301  CGGTATATAG TTCTTCATTT TGGCAGATCT CTACAATATG GAAATCAGTT
6351  CATATATCAG TCAATGCCAC GAATGTTAAC TCTATGGCTT GATTATGGTA
6401  CAAAGGCATA TGAATGGGAA AAAGCTGGCC GCTCCGATCG TGTACAAATG
6451  AGGAATGATT TGGGTAAAAT AAACAAGGTT ATCACAGAGC ATACAAACTA
6501  TTTAGCTCCA TATCAATTTT TGACTGCTTT TTCACAATTG ATCTCTCGAA
6551  TTTGTCATTC TCACGATGAA GTTTTTGTTG TCTTGATGGA AATAATAGCC
6601  AAAGTATTTC TAGCCTATCC TCAACAAGCA ATGTGGATGA TGACAGCTGT
6651  GTCAAAGTCA TCTTATCCCA TGCGTGTGAA CAGATGCAAG GAAATCCTCA
6701  ATAAAGCTAT TCATATGAAA AAATCCTTAG AGAAGTTTGT TGGAGATGCA
6751  ACTCGCCTAA CAGATAAGCT TCTAGAATTG TGCAATAAAC CGGTTGATGG
6801  AAGTAGTTCC ACATTAAGCA TGAGCACTCA TTTTAAAATG CTTAAAAAGC
6851  TGGTAGAAGA AGCAACATTT AGTGAAATCC TCATTCCTCT ACAATCAGTC
6901  ATGATACCTA CACTTCCATC AATTCTGGGT ACCCATGCTA ACCATGCTAG
6951  CCATGAACCA TTTCCTGGAC ATTGGGCCTA TATTGCAGGG TTTGATGATA
7001  TGGTGGAAAT TCTTGCTTCT CTTCAGAAAC CAAAGAAGAT TTCTTTAAAA
7051  GGCTCAGATG GAAAGTTCTA CATCATGATG TGTAAGCCAA AAGATGACCT
7101  GAGAAAGGAT TGTAGACTAA TGGAATTCAA TTCCTTGATT AATAAGTGCT
7151  TAAGAAAAGA TGCAGAGTCT CGTAGAAGAG AACTTCATAT TCGAACATAT
7201  GCAGTTATTC CACTAAATGA TGAATGTGGG ATTATTGAAT GGGTGAACAA
7251  CACTGCTGGT TTGAGACCTA TTCTGACCAA ACTATATAAA GAAAAGGGAG
7301  TGTATATGAC AGGAAAAGAA CTTCGCCAGT GTATGCTACC AAAGTCAGCA
7351  GCTTTATCTG AAAAACTCAA AGTATTCCGA GAATTTCTCC TGCCCAGGCA
7401  TCCTCCTATT TTTCATGAGT GGTTTCTGAG AACATTCCCT GATCCTACAT
7451  CATGGTACAG TAGTAGATCA GCTTACTGCC GTTCCACTGC AGTAATGTCA
7501  ATGGTTGGTT ATATTCTGGG GCTTGGAGAC CGTCATGGTG AAAATATTCT
```

Figure 8b (vi)

```
7551  CTTTGATTCT TTGACTGGTG AATGCGTACA TGTAGATTTC AATTGTCTTT
7601  TCAATAAGGG AGAAACCTTT GAAGTTCCAG AAATTGTGCC ATTTCGCCTG
7651  ACTCATAATA TGGTTAATGG AATGGGTCCT ATGGGAACAG AGGGTCTTTT
7701  TCGAAGAGCA TGTGAAGTTA CAATGAGGCT GATGCGTGAT CAGCGAGAGC
7751  CTTTAATGAG TGTCTTAAAG ACTTTTCTAC ATGATCCTCT TGTGGAATGG
7801  AGTAAACCAG TGAAAGGGCA TTCCAAAGCG CCACTGAATG AAACTGGAGA
7851  AGTTGTCAAT GAAAAGGCCA AGACCCATGT TCTTGACATT GAGCAGCGAC
7901  TACAAGGTGT AATCAAGACT CGAAATAGAG TGACAGGACT GCCGTTATCT
7951  ATTGAAGGAC ATGTGCATTA CCTTATACAG GAAGCTACTG ATGAAAACTT
8001  ACTATGCCAG ATGTATCTTG GTTGGACTCC ATATATGTGA AATGAAATTA
8051  TGTAAAAGAA TATGTTAATA ATCTAAAAGT AATGCATTTG GTATGAATCT
8101  GTGGTTGTAT CTGTTCAATT CTAAAGTACA ACATAAATTT ACGTTCTCAG
8151  CAACTGTTAT TTCTCTCTGA TCATTAATTA TATGTAAAAT AATATACATT
8201  CACTCGTGCC
```

Figure 9a (1)

```
!!NA_SEQUENCE 1.0
ID   HS349941     standard; RNA; HUM; 12780 BP.
XX
AC   U34994;
XX
NI   g995940
XX
DT   26-SEP-1995 (Rel. 45, Created)
DT   22-FEB-1997 (Rel. 51, Last updated, Version 4)
XX
DE   Human DNA-dependent protein kinase catalytic subunit (DNA-PKcs)
DE   mRNA, complete cds.
XX
KW   .
XX
OS   Homo sapiens (human)
OC   Eukaryota; Metazoa; Chordata; Vertebrata; Mammalia; Eutheria; Primates;
OC   Catarrhini; Hominidae; Homo.
XX
RN   [1]
RP   1-12780
RX   MEDLINE; 95401275.
RA   Hartley K.O., Gell D., Smith G.C., Zhang H., Divecha N., Connelly M.A.,
RA   Admon A., Lees-Miller S.P., Anderson C.W., Jackson S.P.;
RT   "DNA-dependent protein kinase catalytic subunit: a relative of
RT   phosphatidylinositol 3-kinase and the ataxia telangiectasia gene
RT   product";
RL   Cell 82:849-856(1995).
XX
RN   [2]
RP   1-12780
RA   Gell D.;
RT   ;
RL   Submitted (29-AUG-1995) to the EMBL/GenBank/DDBJ databases.
RL   Dave Gell, Zoology, Wellcome/CRC, Tennis Court Road, Cambridge CB2 1QR,
RL   UK
XX
DR   SPTREMBL; Q13327; Q13327.
XX
CC   NCBI gi: 995940
XX
FH   Key             Location/Qualifiers
FH
FT   source          1..12780
FT                   /organism="Homo sapiens"
FT                   /chromosome="8"
FT                   /cell_type="He-La"
FT                   /map="8q11"
FT   CDS             53..12343
FT                   /codon_start=1
FT                   /db_xref="PID:g995941"
FT                   /db_xref="SPTREMBL:Q13327"
FT                   /note="DNA-activated protein kinase catalytic subunit; PI
FT                   kinase family member; partial genomic sequence located in
FT                   GenBank Accession Number L27425; Method: conceptual
FT                   translation supplied by author. NCBI gi: 995941"
FT                   /gene="DNA-PKcs"
FT                   /product="DNA dependent protein kinase catalytic subunit"
FT                   /translation="MAGSGAGVRCSLLRLQETLSAADRCGAALAGHQLIRGLGQECVLS
FT                   SSPAVLALQTSLVFSRDFGLLVFVRKSLNSIEFRECREEILKFLCIFLEKMGQKIAPYS
FT                   VEIKNTCTSVYTKDRAAKCKIPALDLLIKLLQTFRSSRLMDEFKIGELFSKFYGELALK
FT                   KKIPDTVLEKVYELLGLLGEVHPSEMINNAENLFRAFLGELKTQMTSAVREPKLPVLAG
FT                   CLKGLSSLLCNFTKSMEEDPQTSREIFNFVLKAIRPQIDLKRYAVPSAGLRLFALHASQ
FT                   FSTCLLDNYVSLFEVLLKWCAHTNVELKKAALSALESFLKQVSNMVAKNAEMHKNKLQY
FT                   FMEQFYGIIRNVDSNNKELSIAIRGYGLFAGPCKVINAKDVDFMYVELIQRCKQMFLTQ
FT                   TDTGDYRVYQMPSFLQSVASVLLYLDTVPEVYTPVLEHLVVMQIDSFPQYSPKMQLVCC
FT                   RAIVKVFLALAAKGPVLRNCISTVVHQGLIRICSKPVVLPKGPESESEDHRASGEVRTG
```

Figure 9a(11)

```
FT        KWKVPTYKDYVDLFRHLLSSDQMMDSILADEAFFSVNSSSESLNHLLYDEFVKSVLKIV
FT        EKLDLTLEIQTVGEQENGDEAPGWWMIPTSDPAANLHPAKPKDFSAFINLVEFCREILP
FT        EKQAEFFEPWVYSFSYELILQSTRLPLISGFYKLLSITVRNAKKIKYFEGVSPKSLKHS
FT        PEDPEKYSCFALFVKFGKEVAVKMKQYKDELLASCLTFLLSLPHNIIELDVRAYVPALQ
FT        MAFKLGLSYTPLAEVGLNALEEWSIYIDRHVMQPYYKDILPCLDGYLKTSALSDETKNN
FT        WEVSALSRAAQKGFNKVVLKHLKKTKNLSSNEAISLEEIRIRVVQMLGSLGGQINKNLL
FT        TVTSSDEMMKSYVAWDREKRLSFAVPFREMKPVIFLDVFLPRVTELALTASDRQTKVAA
FT        CELLHSMVMFMLGKATQMPEGGQGAPPMYQLYKRTFPVLLRLACDVDQVTRQLYEPLVM
FT        QLIHWFTNNKKFESQDTVSLLEAILDGIVDPVDSTLRDFCGRCIREFLKWSIKQITPQQ
FT        QEKSPVNTKSLFKRLYSLALHPNAFKRLGASLAFNNIYREFREEESLVEQFVFEALVIY
FT        MESLALAHADEKSLGTIQQCCDAIDHLCRIIEKKHVSLNKAKKRRLPRGFPPSASLCLL
FT        DLVKWLLAHCGRPQTECRHKSIELFYKFVPLLPGNRSPNLWLKDVLKEBGVSFLINTFE
FT        GGGCGQPSGILAQPTLLYLRGPFSLQATLCWLDLLLAALECYNTFIGERTVGALQVLGT
FT        EAQSSLLKAVAFFLESIAMHDIIAAEKCFGTGAAGNRTSPQEGERYNYSKCTVVVRIME
FT        FTTTLLNTSPEGWKLLKKDLCNTHLMRVLVQTLCEPASIGFNIGDVQVMAHLPDVCVNL
FT        MKALKMSPYKDILETHLREKITAQSIEELCAVNLYGPDAQVDRSRLAAVVSACKQLHRA
FT        GLLHNILPSQSTDLHHSVGTELLSLVYKGIAPGDERQCLPSLDLSCKQLASGLLELAFA
FT        PGGLCERLVSLLLNPAVLSTASLGSSQGSVIHFSHGEYFYSLFSETINTELLKNLDLAV
FT        LELMQSSVDNTKMVSAVLNGMLDQSFRERANQKHQGLKLATTILQHWKKCDSWWAKDSP
FT        LETKMAVLALLAKILQIDSSVSFNTSHGSFPEVFTTYISLLADTKLDLHLKGQAVTLLP
FT        FFTSLTGGSLEELRRVLEQLIVAHFPMQSREFPEGTPRFNNYVDGMKKFLDALELSQSP
FT        MLLELMTEVLCREQQHVMEELFQSSFRRIARRGSCVTQVGLLESVYEMFRKDDPRLSFT
FT        RQSFVDRSLLTLLWHCSLDALREFFSTIVVDAIDVLKSRFTKLNESTFDTQITKKMGYY
FT        KILDVMYSRLPKDDVHAKESKINQVFHGSCITEGNELTKTLIKLCYDAFTENMAGENQL
FT        LERRRLYHCAAYNCAISVICCVFNELKFYQGFLFSEKPEKNLLIFENLIDLKRRYNFPV
FT        EVEVPMERKKKYIEIRKEAREAANGDSDGPSYMSSLSYLADSTLSEEMSQFDFSTGVQS
FT        YSYSSQDPRPATGRFRRREQRDPTVHDDVLELEMDELNRHECMAPLTALVKHMHRSLGP
FT        PQGEEDSVPRDLPSWMKFLHGKLGNPIVPLNIRLFLAKLVINTEEVFRPYAKHWLSPLL
FT        QLAASENNGGEGIHYMVVEIVATILSWTGLATPTGVPKDEVLANRLLNFLMKHVFHPKR
FT        AVFRHNLEIIKTLVECWKDCLSIPYRLIFEKFSGKDPNSKDNSVGIQLLGIVMANDLPP
FT        YDPQCGIQSSEYFQALVNNMSFVRYKEVYAAAAEVLGLILRYVMERKNILEESLCELVA
FT        KQLKQHQNTMEDKFIVCLNKVTKSFPPLADRFMNAVFFLLPKFHGVLKTLCLEVVLCRV
. FT      EGMTELYFQLKSKDFVQVMRHRDERQKVCLDIIYKMMPKLKPVELRELLNPVVEFVSHP
FT        STTCREQMYNILMWIHDNYRDPESETDNDSQEIFKLAKDVLIQGLIDENPGLQLIIRNF
FT        WSHETRLPSNTLDRLLALNSLYSPKIEVHFLSLATNFLLEMTSMSPDYPNPMFEHPLSE
FT        CEFQEYTIDSDWRFRSTVLTPMFVETQASQGTLQTRTQEGSLSARWPVAGQIRATQQQH
FT        DFTLTQTADGRSSFDWLTGSSTDPLVDHTSPSSDSLLFAHKRSERLQRAPLKSVGPDFG
FT        KKRLGLPGDEVDNKVKGAAGRTDLLRLRRRFMRDQEKLSLMYARKGVAEQKREKEIKSE
FT        LKMKQDAQVVLYRSYRHGDLPDIQIKHSSLITPLQAVAQRDPIIAKQLFSSLFSGILKE
FT        MDKFKTLSEKNNITQKLLQDFNRFLNTTFSFFPPFVSCIQDISCQHAALLSLDPAAVSA
FT        GCLASLQQPVGIRLLEEALLRLLPAELPAKRVRGKARLPPDVLRWVELAKLYRSIGEYD
FT        VLRGIFTSEIGTKQITQSALLAEARSDYSEAAKQYDEALNKQDWVDGEPTEAEKDFWEL
FT        ASLDCYNHLAEWKSLEYCSTASIDSENPPDLNKIWSEPFYQETYLPYMIRSKLKLLQG
FT        EADQSLLTFIDKAMHGELQKAILELHYSQELSLLYLLQDDVDRAKYYIQNGIQSFMQNY
FT        SSIDVLLHQSRLTKLQSVQALTEIQEFISFISKQGNLSSQVPLKRLLNTWTNRYPDAKM
FT        DPMNIWDDIITNRCFFLSKIEEKLTPLPEDNSMNVDQDGDPSDRMEVQEQEEDISSLIR
FT        SCKFSMKMKMIDSARRQNNFSLAMKILLKELHKESKTRDDWLVSWVQSYCRLSHCRSRSQ
FT        GCSEQVLTVLKTVSLLDENNVSSYLKKNILAFRDQNILLGTTYRIIANALSSEPACLAE
FT        IEEDKARRILELSGSSSEDSEKVIAGLYQRAFQHLSEAVQAAEEEAQPPSWSCGPAAGV
FT        IDAYMTLADFCDQQLRKEEENASVTDSAELQAYPALVVEKMLKALKLNSNEARLKFPRL
FT        LQIIERYPEETLSLMTKEISSVPCWQFISWISHMVALLDKDQAVAVQHSVEEITIDNYPQ
FT        AIVYPFIISSESYSFKDTSTGHKNKEFVARIKSKLDQGGVIQDFINALDQLSNPELLFK
FT        DWSNDVRAELARTPVNKKNIEKMYERMYAALGDPKAPGLGAFRRKFIQTFGKEFDKHFG
FT        KGGSKLLRHKLSDFNDITNMLLLKMNKDSKPPGNLKECSPWMSDFKVEFLRNELEIPGQ
FT        YDGRGKPLPEYHVRIAGFDERVTVMASLRRPKRIIIRGHDEREHPFLVKGGEDLRQDQR
FT        VEQLFQVMNGILAQDSACSQRALQLRTYSVVPMTSSDPRAPPCEYKIWLTKMSGKHDVG
FT        AYMLMYKGANRTETVTSFRKRESKVPADLLKKRAFVRMSTSPEAFLALRSHFASSHALIC
FT        ISHWILGIGDRHLNNFMVAMETGGVIGIDFGHAFGSATQFLPVPELMPFRLTRQFINLM
FT        LPMKETGLMYSIMVHALRAFSRDPGLLTNTMDVFVKEPSFDWKNFBQKMLKKGGSWIQE
FT        INVAEKNWYPRQKICYAKRKLAGANPAVITCDELLLGHEKAPAFRDYVAVARGSKDHNI
FT        RAQEPESGLSEETQVKCLMDQATDPNILGRTWEGWEPWM*
XX
SQ        Sequence 12780 BP; 3612 A; 2769 C; 3084 G; 3314 T; 1 other;
     U34994 Length: 12780  July 10, 1998 12:15  Type: N  Check: 8189  .. Figure 9b(1)
            1 ATTTCCGGGT CCGGGCCGAG CGGGCGCACG CGCGGGAGCG GGACTCGGCG
```

Figure 9b (ii)

```
  51  GCATGGCGGG CTCCGGAGCC GGTGTGCGTT GCTCCCTGCT GCGGCTGCAG
 101  GAGACCTTGT CCGCTGCGGA CCGCTGCGGT GCTGCCCTGG CCGGTCATCA
 151  ACTGATCCGC GGCCTGGGGC AGGAATGCGT CCTGAGCAGC AGCCCCGCGG
 201  TGCTGGCATT ACAGACATCT TTAGTTTTTT CCAGAGATTT CGGTTTGCTT
 251  GTATTTGTCC GGAAGTCACT CAACAGTATT GAATTTCGTG AATGTAGAGA
 301  AGAAATCCTA AAGTTTTTAT GTATTTTCTT AGAAAAAATG GGCCAGAAGA
 351  TCGCACCTTA CTCTGTTGAA ATTAAGAACA CTTGTACCAG TGTTTATACA
 401  AAAGATAGAG CTGCTAAATG TAAAATTCCA GCCCTGGACC TTCTTATTAA
 451  GTTACTTCAG ACTTTTAGAA GTTCTAGACT CATGGATGAA TTTAAAATTG
 501  GAGAATTATT TAGTAAATTC TATGGAGAAC TTGCATTGAA AAAAAAAATA
 551  CCAGATACAG TTTTAGAAAA AGTATATGAG CTCCTAGGAT TATTGGGTGA
 601  AGTTCATCCT AGTGAGATGA TAAATAATGC AGAAAACCTG TTCCGCGCTT
 651  TTCTGGGTGA ACTTAAGACC CAGATGACAT CAGCAGTAAG AGAGCCCAAA
 701  CTACCTGTTC TGGCAGGATG TCTGAAGGGG TTGTCCTCAC TTCTGTGCAA
 751  CTTCACTAAG TCCATGGAAG AAGATCCCCA GACTTCAAGG GAGATTTTTA
 801  ATTTTGTACT AAAGGCAATT CGTCCTCAGA TTGATCTGAA GAGATATGCT
 851  GTGCCCTCAG CTGGCTTGCG CCTATTTGCC CTGCATGCAT CTCAGTTTAG
 901  CACCTGCCTT CTGGACAACT ACGTGTCTCT ATTTGAAGTC TTGTTAAAGT
 951  GGTGTGCCCA CACAAATGTA GAATTGAAAA AAGCTGCACT TTCAGCCCTG
1001  GAATCCTTTC TGAAACAGGT TTCTAATATG GTGGCGAAAA ATGCAGAAAT
1051  GCATAAAAAT AAACTGCAGT ACTTTATGGA GCAGTTTTAT GGAATCATCA
1101  GAAATGTGGA TTCGAACAAC AAGGAGTTAT CTATTGCTAT CCGTGGATAT
1151  GGACTTTTTG CAGGACCGTG CAAGGTTATA AACGCAAAAG ATGTTGACTT
1201  CATGTACGTT GAGCTCATTC AGCGCTGCAA GCAGATGTTC CTCACCCAGA
1251  CAGACACTGG TGACTACCGT GTTTATCAGA TGCCAAGCTT CCTCCAGTCT
1301  GTTGCAAGCG TCTTGCTGTA CCTTGACACA GTTCCTGAGG TGTATACTCC
1351  AGTTCTGGAG CACCTCGTGG TGATGCAGAT AGACAGTTTC CCACAGTACA
1401  GTCCAAAAAT GCAGCTGGTG TGTTGCAGAG CCATAGTGAA GGTGTTCCTA
1451  GCTTTGGCAG CAAAAGGGCC AGTTCTCAGG AATTGCATTA GTACTGTGGT
1501  GCATCAGGGT TTAATCAGAA TATGTTCTAA ACCAGTGGTC CTTCCAAAGG
1551  GCCCTGAGTC TGAATCTGAA GACCACCGTG CTTCAGGGGA AGTCAGAACT
1601  GGCAAATGGA AGGTGCCCAC ATACAAAGAC TACGTGGATC TCTTCAGACA
1651  TCTCCTGAGC TCTGACCAGA TGATGGATTC TATTTTAGCA GATGAAGCAT
```

Figure 9b (iii)

```
1701  TTTTCTCTGT GAATTCCTCC AGTGAAAGTC TGAATCATTT ACTTTATGAT
1751  GAATTTGTAA AATCCGTTTT GAAGATTGTT GAGAAATTGG ATCTTACACT
1801  TGAAATACAG ACTGTTGGGG AACAAGAGAA TGGAGATGAG GCGCCTGGTG
1851  TTTGGATGAT CCCAACTTCA GATCCAGCGG CTAACTTGCA TCCAGCTAAA
1901  CCTAAAGATT TTTCGGCTTT CATTAACCTG GTGGAATTTT GCAGAGAGAT
1951  TCTCCCTGAG AAACAAGCAG AATTTTTTGA ACCATGGGTG TACTCATTTT
2001  CATATGAATT AATTTTGCAA TCTACAAGGT TGCCCCTCAT CAGTGGTTTC
2051  TACAAATTGC TTTCTATTAC AGTAAGAAAT GCCAAGAAAA TAAAATATTT
2101  CGAGGGAGTT AGTCCAAAGA GTCTGAAACA CTCTCCTGAA GACCCAGAAA
2151  AGTATTCTTG CTTTGCTTTA TTTGTGAAAT TTGGCAAAGA GGTGGCAGTT
2201  AAAATGAAGC AGTACAAAGA TGAACTTTTG GCCTCTTGTT TGACCTTTCT
2251  TCTGTCCTTG CCACACAACA TCATTGAACT CGATGTTAGA GCCTACGTTC
2301  CTGCACTGCA GATGGCTTTC AAACTGGGCC TGAGCTATAC CCCCTTGGCA
2351  GAAGTAGGCC TGAATGCTCT AGAAGAATGG TCAATTTATA TTGACAGACA
2401  TGTAATGCAG CCTTATTACA AAGACATTCT CCCCTGCCTG GATGGATACC
2451  TGAAGACTTC AGCCTTGTCA GATGAGACCA AGAATAACTG GAAGTGTCA
2501  GCTCTTTCTC GGGCTGCCCA GAAAGGATTT AATAAAGTGG TGTTAAAGCA
2551  TCTGAAGAAG ACAAAGAACC TTTCATCAAA CGAAGCAATA TCCTTAGAAG
2601  AAATAAGAAT TAGAGTAGTA CAAATGCTTG GATCTCTAGG AGGACAAATA
2651  AACAAAAATC TTCTGACAGT CACGTCCTCA GATGAGATGA TGAAGAGCTA
2701  TGTGGCCTGG GACAGAGAGA AGCGGCTGAG CTTTGCAGTG CCCTTTAGAG
2751  AGATGAAACC TGTCATTTTC CTGGATGTGT TCCTGCCTCG AGTCACAGAA
2801  TTAGCGCTCA CAGCCAGTGA CAGACAAACT AAAGTTGCAG CCTGTGAACT
2851  TTTACATAGC ATGGTTATGT TTATGTTGGG CAAAGCCACG CAGATGCCAG
2901  AAGGGGACA GGGAGCCCCA CCCATGTACC AGCTCTATAA GCGGACGTTT
2951  CCTGTGCTGC TTCGACTTGC GTGTGATGTT GATCAGGTGA CAAGGCAACT
3001  GTATGAGCCA CTAGTTATGC AGCTGATTCA CTGGTTCACT AACAACAAGA
3051  AATTTGAAAG TCAGGATACT GTTTCCTTAC TAGAAGCTAT ATTGGATGGA
3101  ATTGTGGACC CTGTTGACAG TACTTTAAGA GATTTTTGTG GTCGGTGTAT
3151  TCGAGAATTC CTTAAATGGT CCATTAAGCA AATAACACCA CAGCAGCAGG
3201  AGAAGAGTCC AGTAAACACC AAATCGCTTT TCAAGCGACT TTATAGCCTT
3251  GCGCTTCACC CCAATGCTTT CAAGAGGCTG GGAGCATCAC TTGCCTTTAA
3301  TAATATCTAC AGGGAATTCA GGGAAGAAGA GTCTCTGGTG GAACAGTTTG
3351  TGTTTGAAGC CTTGGTGATA TACATGGAGA GTCTGGCCTT AGCACATGCA
```

Figure 9b (iv)

```
3401  GATGAGAAGT CCTTAGGTAC AATTCAACAG TGTTGTGATG CCATTGATCA
3451  CCTATGCCGC ATCATTGAAA AGAAGCATGT TTCTTTAAAT AAAGCAAAGA
3501  AACGACGTTT GCCGCGAGGA TTTCCACCTT CCGCATCATT GTGTTTATTG
3551  GATCTGGTCA AGTGGCTTTT AGCTCATTGT GGGAGGCCCC AGACAGAATG
3601  TCGACACAAA TCCATTGAAC TCTTTTATAA ATTCGTTCCT TTATTGCCAG
3651  GCAACAGATC CCCTAATTTG TGGCTGAAAG ATGTTCTCAA GGAAGAAGGT
3701  GTCTCTTTTC TCATCAACAC CTTTGAGGGG GGTGGCTGTG CCAGCCCTC
3751  GGGCATCCTG GCCCAGCCCA CCCTCTTGTA CCTTCGGGGG CCATTCAGCC
3801  TGCAGGCCAC GCTATGCTGG CTGGACCTGC TCCTGGCCGC GTTGGAGTGC
3851  TACAACACGT TCATTGGCGA GAGAACTGTA GGAGCGCTCC AGGTCCTAGG
3901  TACTGAAGCC CAGTCTTCAC TTTTGAAAGC AGTGGCTTTC TTCTTAGAAA
3951  GCATTGCCAT GCATGACATT ATAGCAGCAG AAAAGTGCTT TGGCACTGGG
4001  GCAGCAGGTA ACAGAACAAG CCCACAAGAG GGAGAAAGGT ACAACTACAG
4051  CAAATGCACC GTTGTGGTCC GGATTATGGA GTTACCACG ACTCTGCTAA
4101  ACACCTCCCC GGAAGGATGG AAGCTCCTGA AGAAGGACTT GTGTAATACA
4151  CACCTGATGA GAGTCCTGGT GCAGACGCTG TGTGAGCCCG CAAGCATAGG
4201  TTTCAACATC GGAGACGTCC AGGTTATGGC TCATCTTCCT GATGTTTGTG
4251  TGAATCTGAT GAAAGCTCTA AAGATGTCCC CATACAAAGA TATCCTAGAG
4301  ACCCATCTGA GAGAGAAAAT AACAGCACAG AGCATTGAGG AGCTTTGTGC
4351  CGTCAACTTG TATGGCCCTG ACGCGCAAGT GGACAGGAGC AGGCTGGCTG
4401  CTGTTGTGTC TGCCTGTAAA CAGCTTCACA GAGCTGGGCT TCTGCATAAT
4451  ATATTACCGT CTCAGTCCAC AGATTTGCAT CATTCTGTTG GCACAGAACT
4501  TCTTTCCCTG GTTTATAAAG GCATTGCCCC TGGAGATGAG AGACAGTGTC
4551  TGCCTTCTCT AGACCTCAGT TGTAAGCAGC TGGCCAGCGG ACTTCTGGAG
4601  TTAGCCTTTG CTTTTGGAGG ACTGTGTGAG CGCCTTGTGA GTCTTCTCCT
4651  GAACCCAGCG GTGCTGTCCA CGGCGTCCTT GGGCAGCTCA CAGGGCAGCG
4701  TCATCCACTT CTCCCATGGG GAGTATTTCT ATAGCTTGTT CTCAGAAACG
4751  ATCAACACGG AATTATTGAA AAATCTGGAT CTTGCTGTAT TGGAGCTCAT
4801  GCAGTCTTCA GTGGATAATA CCAAAATGGT GAGTGCCGTT TTGAACGGCA
4851  TGTTAGACCA GAGCTTCAGG GAGCGAGCAA ACCAGAAACA CCAAGGACTG
4901  AAACTTGCGA CTACAATTCT GCAACACTGG AAGAAGTGTG ATTCATGGTG
4951  GGCCAAAGAT TCCCCTCTCG AAACTAAAAT GGCAGTGCTG GCCTTACTGG
5001  CAAAAATTTT ACAGATTGAT TCATCTGTAT CTTTTAATAC AAGTCATGGT
```

Figure 9b (v)

```
5051  TCATTCCCTG AAGTCTTTAC AACATATATT AGTCTACTTG CTGACACAAA
5101  GCTGGATCTA CATTTAAAGG GCCAAGCTGT CACTCTTCTT CCATTCTTCA
5151  CCAGCCTCAC TGGAGGCAGT CTGGAGGAAC TTAGACGTGT TCTGGAGCAG
5201  CTCATCGTTG CTCACTTCCC CATGCAGTCC AGGGAATTTC CTCCAGGAAC
5251  TCCGCGGTTC AATAATTATG TGGACTGCAT GAAAAAGTTT CTAGATGCAT
5301  TGGAATTATC TCAAAGCCCT ATGTTGTTGG AATTGATGAC AGAAGTTCTT
5351  TGTCGGGAAC AGCAGCATGT CATGGAAGAA TTATTTCAAT CCAGTTTCAG
5401  GAGGATTGCC AGAAGGGGTT CATGTGTCAC ACAAGTAGGC CTTCTGGAAA
5451  GCGTGTATGA AATGTTCAGG AAGGATGACC CCCGCCTAAG TTTCACACGC
5501  CAGTCCTTTG TGGACCGCTC CCTCCTCACT CTGCTGTGGC ACTGTAGCCT
5551  GGATGCTTTG AGAGAATTCT TCAGCACAAT TGTGGTGGAT GCCATTGATG
5601  TGTTGAAGTC CAGGTTTACA AAGCTAAATG AATCTACCTT TGATACTCAA
5651  ATCACCAAGA AGATGGGCTA CTATAAGATT CTAGACGTGA TGTATTCTCG
5701  CCTTCCCAAA GATGATGTTC ATGCTAAGGA ATCAAAAATT AATCAAGTTT
5751  TCCATGGCTC GTGTATTACA GAAGGAAATG AACTTACAAA GACATTGATT
5801  AAATTGTGCT ACGATGCATT TACAGAGAAC ATGGCAGGAG AGAATCAGCT
5851  GCTGGAGAGG AGAAGACTTT ACCATTGTGC AGCATACAAC TGCGCCATAT
5901  CTGTCATCTG CTGTGTCTTC AATGAGTTAA AATTTTACCA AGGTTTTCTG
5951  TTTAGTGAAA AACCAGAAAA GAACTTGCTT ATTTTTGAAA ATCTGATCGA
6001  CCTGAAGCGC CGCTATAATT TTCCTGTAGA AGTTGAGGTT CCTATGGAAA
6051  GAAAGAAAAA GTACATTGAA ATTAGGAAAG AAGCCAGAGA AGCAGCAAAT
6101  GGGGATTCAG ATGGTCCTTC CTATATGTCT TCCCTGTCAT ATTTGGCAGA
6151  CAGTACCCTG AGTGAGGAAA TGAGTCAATT TGATTTCTCA ACCGGAGTTC
6201  AGAGCTATTC ATACAGCTCC CAAGACCCTA GACCTGCCAC TGGTCGTTTT
6251  CGGAGACGGG AGCAGCGGGA CCCCACGGTG CATGATGATG TGCTGGAGCT
6301  GGAGATGGAC GAGCTCAATC GGCATGAGTG CATGGCGCCC CTGACGGCCC
6351  TGGTCAAGCA CATGCACAGA AGCCTGGGCC CGCCTCAAGG AGAAGAGGAT
6401  TCAGTGCCAA GAGATCTTCC TTCTTGGATG AAATTCCTCC ATGGCAAACT
6451  GGGAAATCCA ATAGTACCAT TAAATATCCG TCTCTTCTTA GCCAAGCTTG
6501  TTATTAATAC AGAAGAGGTC TTTCGCCCTT ACGCGAAGCA CTGGCTTAGC
6551  CCCTTGCTGC AGCTGGCTGC TTCTGAAAAC AATGGAGGAG AAGGAATTCA
6601  CTACATGGTG GTTGAGATAG TGGCCACTAT TCTTTCATGG ACAGGCTTGG
6651  CCACTCCAAC AGGGGTCCCT AAAGATGAAG TGTTAGCAAA TCGATTGCTT
6701  AATTTCCTAA TGAAACATGT CTTTCATCCA AAAAGAGCTG TGTTTAGACA
```

Figure 9b (vi)

```
6751  CAACCTTGAA ATTATAAAGA CCCTTGTCGA GTGCTGGAAG GATTGTTTAT
6801  CCATCCCTTA TAGGTTAATA TTTGAAAAGT TTTCCGGTAA AGATCCTAAT
6851  TCTAAAGACA ACTCAGTAGG GATTCAATTG CTAGGCATCG TGATGGCCAA
6901  TGACCTGCCT CCCTATGACC CACAGTGTGG CATCCAGAGT AGCGAATACT
6951  TCCAGGCTTT GGTGAATAAT ATGTCCTTTG TAAGATATAA AGAAGTGTAT
7001  GCCGCTGCAG CAGAAGTTCT AGGACTTATA CTTCGATATG TTATGGAGAG
7051  AAAAAACATA CTGGAGGAGT CTCTGTGTGA ACTGGTTGCG AAACAATTGA
7101  AGCAACATCA GAATACTATG GAGGACAAGT TTATTGTGTG CTTGAACAAA
7151  GTGACCAAGA GCTTCCCTCC TCTTGCAGAC AGGTTCATGA ATGCTGTGTT
7201  CTTTCTGCTG CCAAAATTTC ATGGAGTGTT GAAACACTC TGTCTGGAGG
7251  TGGTACTTTG TCGTGTGGAG GGAATGACAG AGCTGTACTT CCAGTTAAAG
7301  AGCAAGGACT TCGTTCAAGT CATGAGACAT AGAGATGAAA GACAAAAAGT
7351  ATGTTTGGAC ATAATTTATA AGATGATGCC AAAGTTAAAA CCAGTAGAAC
7401  TCCGAGAACT TCTGAACCCC GTTGTGGAAT TCGTTTCCCA TCCTTCTACA
7451  ACATGTAGGG AACAAATGTA TAATATTCTC ATGTGGATTC ATGATAATTA
7501  CAGAGATCCA GAAAGTGAGA CAGATAATGA CTCCCAGGAA ATATTTAAGT
7551  TGGCAAAAGA TGTGCTGATT CAAGGATTGA TCGATGAGAA CCCTGGACTT
7601  CAATTAATTA TTCGAAATTT CTGGAGCCAT GAAACTAGGT TACCTTCAAA
7651  TACCTTGGAC CGGTTGCTGG CACTAAATTC CTTATATTCT CCTAAGATAG
7701  AAGTGCACTT TTTAAGTTTA GCAACAAATT TTCTGCTCGA AATGACCAGC
7751  ATGAGCCCAG ATTATCCAAA CCCCATGTTC GAGCATCCTC TGTCAGAATG
7801  CGAATTTCAG GAATATACCA TTGATTCTGA TTGGCGTTTC CGAAGTACTG
7851  TTCTCACTCC GATGTTTGTG GAGACCCAGG CCTCCCAGGG CACTCTCCAG
7901  ACCCGTACCC AGGAAGGGTC CCTCTCAGCT CGCTGGCCAG TGGCAGGGCA
7951  GATAAGGGCC ACCCAGCAGC AGCATGACTT CACACTGACA CAGACTGCAG
8001  ATGGAAGAAG CTCATTTGAT TGGCTGACCG GGAGCAGCAC TGACCCGCTG
8051  GTCGACCACA CCAGTCCCTC ATCTGACTCC TTGCTGTTTG CCCACAAGAG
8101  GAGTGAAAGG TTACAGAGAG CACCCTTGAA GTCAGTGGGG CCTGATTTTG
8151  GGAAAAAAAG GCTGGGCCTT CCAGGGGACG AGGTGGATAA CAAAGTGAAA
8201  GGTGCGGCCG GCCGGACGGA CCTACTACGA CTGCGCAGAC GGTTTATGAG
8251  GGACCAGGAG AAGCTCAGTT TGATGTATGC CAGAAAAGGC GTTGCTGAGC
8301  AAAAACGAGA GAAGGAAATC AAGAGTGAGT TAAAAATGAA GCAGGATGCC
8351  CAGGTCGTTC TGTACAGAAG CTACCGGCAC GGAGACCTTC CTGACATTCA
```

Figure 9b (vii)

```
8401  GATCAAGCAC AGCAGCCTCA TCACCCCGTT ACAGGCCGTG GCCCAGAGGG
8451  ACCCAATAAT TGCAAAACAG CTCTTTAGCA GCTTGTTTTC TGGAATTTTG
8501  AAAGAGATGG ATAAATTTAA GACACTGTCT GAAAAAAACA ACATCACTCA
8551  AAAGTTGCTT CAAGACTTCA ATCGTTTTCT TAATACCACC TTCTCTTTCT
8601  TTCCACCCTT TGTCTCTTGT ATTCAGGACA TTAGCTGTCA GCACGCAGCC
8651  CTGCTGAGCC TCGACCCAGC GGCTGTTAGC GCTGGTTGCC TGGCCAGCCT
8701  ACAGCAGCCC GTGGGCATCC GCCTGCTAGA GGAGGCTCTG CTCCGCCTGC
8751  TGCCTGCTGA GCTGCCTGCC AAGCGAGTCC GTGGGAAGGC CCGCCTCCCT
8801  CCTGATGTCC TCAGATGGGT GGAGCTTGCT AAGCTGTATA GATCAATTGG
8851  AGAATACGAC GTCCTCCGTG GGATTTTTAC CAGTGAGATA GGAACAAAGC
8901  AAATCACTCA GAGTGCATTA TTAGCAGAAG CCAGAAGTGA TTATTCTGAA
8951  GCTGCTAAGC AGTATGATGA GGCTCTCAAT AAACAAGACT GGGTAGATGG
9001  TGAGCCCACA GAAGCCGAGA AGGATTTTTG GAACTTGCA TCCCTTGACT
9051  GTTACAACCA CCTTGCTGAG TGGAAATCAC TTGAATACTG TTCTACAGCC
9101  AGTATAGACA GTGAGAACCC CCCAGACCTA AATAAAATCT GGAGTGAACC
9151  ATTTTATCAG GAAACATATC TACCTTACAT GATCCGCAGC AAGCTGAAGC
9201  TGCTGCTCCA GGGAGAGGCT GACCAGTCCC TGCTGACATT TATTGACAAA
9251  GCTATGCACG GGGAGCTCCA GAAGGCGATT CTAGAGCTTC ATTACAGTCA
9301  AGAGCTGAGT CTGCTTTACC TCCTGCAAGA TGATGTTGAC AGAGCCAAAT
9351  ATTACATTCA AAATGGCATT CAGAGTTTTA TGCAGAATTA TTCTAGTATT
9401  GATGTCCTCT TACACCAAAG TAGACTCACC AAATTGCAGT CTGTACAGGC
9451  TTTAACAGAA ATTCAGGAGT TCATCAGCTT TATAAGCAAA CAAGGCAATT
9501  TATCATCTCA AGTTCCCCTT AAGAGACTTC TGAACACCTG GACAAACAGA
9551  TATCCAGATG CTAAAATGGA CCCAATGAAC ATCTGGGATG ACATCATCAC
9601  AAATCGATGT TTCTTTCTCA GCAAAATAGA GGAGAAGCTT ACCCCTCTTC
9651  CAGAAGATAA TAGTATGAAT GTGGATCAAG ATGGAGACCC CAGTGACAGG
9701  ATGGAAGTGC AAGAGCAGGA AGAAGATATC AGCTCCCTGA TCAGGAGTTG
9751  CAAGTTTTCC ATGAAAATGA AGATGATAGA CAGTGCCCGG AAGCAGAACA
9801  ATTTCTCACT TGCTATGAAA CTACTGAAGG AGCTGCATAA AGAGTCAAAA
9851  ACCAGAGACG ATTGGCTGGT GAGCTGGGTG CAGAGCTACT GCCGCCTGAG
9901  CCACTGCCGG AGCCGGTCCC AGGGCTGCTC TGAGCAGGTG CTCACTGTGC
9951  TGAAAACAGT CTCTTTGTTG GATGAGAACA ACGTGTCAAG CTACTTAARC
10001 AAAAATATTC TGGCTTTCCG TGACCAGAAC ATTCTCTTGG GTACAACTTA
10051 CAGGATCATA GCGAATGCTC TCAGCAGTGA GCCAGCCTGC CTTGCTGAAA
```

INTERACTIONS OF ATM, ATR OR DAN-PK WITH P53

CROSS REFERENCE TO RELATED APPLICATIONS

This application is a 35 U.S.C. §371 National Stage filing of International Application PCT/GB98/02115, filed Jul. 16, 1998, which claims priority to Great Britain application no. 9714971.0, filed Jul. 16, 1997.

The present invention relates to screening methods, peptides, mimetics, and methods of use based on the surprising discovery and characterisation of an interaction between known proteins, and thus numerous cellular processes of interest in therapeutic contexts. The proteins in question are ATM and p53, and the inventors have found that ATM phosphorylates p53 at a number of specific sites. This interaction is observed with other related proteins with associated kinase activity, in particular ATR and DNA-PK, and other proteins having similar phosphorylation sites to p53. Further aspects of the present invention are founded on the discovery that ATM binds DNA and that such binding has an effect on phosphorylation of p53 by ATM.

Ataxia-telangiectasia (A-T) is a human autosomal recessive disorder characterised by a number of debilitating symptoms, including a progressive cerebellar degeneration, occulocutaneous telangiectasia, growth retardation, immune deficiencies and certain characteristics of premature ageing (reviewed in Jackson, 1995; Meyn, 1995; Shiloh, 1995). A-T patients exhibit an approximately 100-fold increased incidence of cancer, with patients being particularly predisposed to malignancies of lymphoid origin. Furthermore, A-T heterozygotes, which comprise ~1% of the population, are reported to exhibit a higher incidence of breast cancer (Easton, 1994; Meyn, 1995), although this remains controversial (Fitzgerald et al., 1997). At the cellular level, A-T is characterised by a high degree of chromosomal instability, radioresistant DNA synthesis, and hypersensitivity to ionising radiation (IR) and radiomimetic drugs. In addition, A-T cells are defective in the radiation induced G1-S, S, and G2-M cell cycle checkpoints that are thought to arrest the cell cycle in response to DNA damage in order to allow repair of the genome prior to DNA replication or mitosis (Halazonetis et al., 1993; Beamish et al., 1994; Beamish and Lavin, 1994; Khanna et al., 1995; Barlow et al., 1996; Xu and Baltimore, 1996). A-T cells exhibit deficient or severely delayed induction of p53 in response to IR (Kastan et al., 1992; Khanna and Lavin, 1993; Lu and Lane, 1993; Xu and Baltimore, 1996). p53 mediated transcriptional activation of p21/WAF1/CIP1 and Gadd45, and the subsequent inhibition of G1 cyclin-dependent kinases, are also defective in A-T cells following IR exposure (Artuso et al., 1995; Khanna et al., 1995). Lu and Lane, 1993, however, reported very little difference in the p53 response from normal and A-T cells.

Furthermore, yeast have an ATM homologue (Mec1) but do not have p53 (Goffeau et al.). The best data for a possible substrate for Mec1p is Spk1/Rad53 (Sun et al; Sanchez et al.)

The gene mutated in A-T patients, termed ATM (A-T mutated), has been mapped and its cDNA cloned (Savitsky et al., 1995a; Savitsky et al., 1995b). Sequence analyses reveal that the ATM gene encodes a ~350 kDa polypeptide that is a member of the phosphatidylinositol (PI) 3-kinase family of proteins by virtue of a putative kinase domain in its carboxy-terminal region (Savitsky et al., 1995a; Savitsky et al., 1995b). Classical PI 3-kinases, such as PI 3-kinase itself, are involved in signal transduction and phosphorylate inositol lipids that act as intracellular second messengers (reviewed in Kapeller and Cantley, 1994). ATM bears sequence similarity with a subset of the PI 3-kinase protein family that comprises proteins which, like ATM, are involved in cell cycle control and/or in the detection and signalling of DNA damage (for reviews see Hunter, 1995; Keith and Schreiber, 1995; Zakian, 1995; Jackson, 1996). Included in this sub-group are *Saccharomyces cerevisiae* Tor1p and Tor2p and their mammalian homologue FRAP, which control progression into S-phase and, at least in part, function by regulating translation (Brown and Schreiber, 1996). Also in this sub-group is the DNA dependent protein kinase (DNA-PK) catalytic subunit (DNA-PKcs), defects in which lead to sensitivity to IR and an inability to perform site-specific V(D)J recombination (reviewed in Jackson and Jeggo, 1995; Jackson, 1996). Other members of the ATM sub-group of the PI 3-kinase family that have been identified include *S. cerevisiae* Tel1p and Mec1p, together with the Mec1p homologues of *Schizosaccharomyces pombe* (rad3), *Drosophila melanogaster* (mei-41) and humans FRP1/ATR; (Keith and Schreiber, 1995; Zakian, 1995; Jackson, 1996). As with ATM, defects in these proteins lead to genomic instability, hypersensitivity towards DNA damaging agents and defects in DNA damage-induced cell cycle checkpoint controls.

ATM is most similar to *S. cerevisiae* Tel1p, which has not been shown to have any biochemical function so far (identity and similarity are 45% and 66%, respectively). ATM is much further diverged from DNA-PKcs (28% identical and 51% similar), with essentially the same homology to PI 3-kinase (a bona fide lipid kinase: 24% identical and 51% similar). Thus, from the sequence comparisons alone, one could not predict that ATM would be a protein kinase akin to DNA-PKcs or a lipid kinase akin to PI 3-kinase.

Although genetic data indicate an involvement of ATM-like proteins in DNA damage recognition and its repair, the mechanisms by which these proteins function are not well understood. Much is known about the clinical symptoms and cellular phenotypes that arise from mutations in ATM, but little is known about the mechanisms by which the ATM protein functions. Recent studies have revealed that, like DNA-PKcs, ATM is expressed ubiquitously and is localised predominantly in the cell nucleus (Chen and Lee, 1996; Lakin et al., 1996; Brown et al., 1997; Watters et al., 1997).

The realisation that ATM is a member of the PI 3-kinase family has suggested to some that the primary function of ATM might phosphorylate inositol phospholipids. Savitsky et al (1995 Science 268, 1749–1753), for example, do not discuss protein phosphorylation. Indeed, several lines of evidence suggest that ATM might have functioned in a very different way from that which we have established herein. For example, defective protein tyrosine phosphorylation and calcium mobilization in response to the triggering of B-cells and T-cells of A-T patients support the idea of defects in intra-cytoplasmic signalling pathways in A-T cells (cited in the Savitski Science paper 1995). These data are provided in the paper Khanna et al (1997; J. Biol. Chem.). This paper also summarises a variety of other data suggesting different ways in which ATM might function.

Savitsky et al (Science 1995) state that the insulin-dependent diabetes observed in some A-T patients could reflect ATM acting in an analogous way to PI 3-kinase affecting glucose transport by insulin. They also discuss PI 3-kinase in terms of controlling apoptosis as a paradigm for ATM, ie. one can explain many of the features of A-T by suggesting that it works analogously to PI 3-kinase.

Some A-T cells have been shown to be complemented by a gene called ATDC, whose product interacts with an intermediate filament protein called vimentin, which is cytoplasmic (Brzoska et al; PNAS). They state that A-T cell lines have aberrantly aggregated actin filaments, suggesting the role of ATM lies in the cytoplasm.

We have purified ATM. We report that, ATM binds to DNA and possesses an associated protein kinase activity that is stimulated by DNA. Furthermore, we show that ATM serves as a kinase for p53 and that the sites of phosphorylation reside in functionally important regions of the p53 polypeptide. These sites are Ser15 and Thr18. We also show that DNA-PK is also capable of phosphorylating the Ser15 and Thr18 sites of p53, and that ATR phosphorylates Ser15. Further, we show that phosphorylation of these sites of p53 disrupts the interaction of p53 with Mdm-2, a protein which targets p53 for degradation within the cell.

By targeting these sites, ATM may activate p53 for DNA binding and/or cause disassociation of Mdm-2, thus stabilising p53 (leading to increased amounts of the protein) and would allow it to activate transcription.

Thr18 of p53 has to our knowledge never been shown to be phosphorylated in vivo or in vitro. This site does not conform to a characterized DNA-PK consensus phosphorylation site. Thus, our finding of phosphorylation here is totally unexpected.

Ser15 is phosphorylated by DNA-PK, but nonetheless its phosphorylation by ATM is also surprising, particularly since there are no data indicating its phosphorylation in reponse to DNA damage being altered in A-T cells.

Based on this and other work described below, the present invention in various aspects provides for modulation of interaction between ATM (and ATR) and p53, particularly phosphorylation of p53 by ATM and ATR, and DNA binding by these proteins, which is further shown to have a potentiating effect on phosphorylation of p53.

Various aspects of the present invention provide for the use of ATM (or related kinases such as ATR or DNA-PK) and p53, with or without DNA, in screening methods and assays for agents which modulate interaction between ATM and p53, particularly phosphorylation of p53 by ATM.

Further aspects provide for modulation of interaction between ATM, or related kinases such as ATR or DNA-PK, and other molecules including a phosphorylation site homologous to those in p53 which are phosphorylated by ATM, and use of these molecules in screening methods and assays for useful agents. For simplicity, much of the present disclosure refers to ATM and p53. However, unless the context requires otherwise, every such reference should be taken to be equally applicable to the interaction between ATM and other molecules including a site homologous to one of those in p53 phosphorylated by ATM. Similarly, based on the disclosure herein, the invention extends to the use of other protein kinases which have an associated protein kinase activity capable of phosphorylating sites of p53, in particular Ser15 and Thr18. Typically, the protein kinase domain of these other kinases will share at least 30% amino acid sequence identity with the corresponding domain of ATM, more preferably at least 35% sequence identity, more preferably at least 40% sequence identity, more preferably at least 50% sequence identity, more preferably at least 70% sequence identity, still more preferably at least 90% sequence identity. Examples of such kinases are ATR (also known as FRP1, see Cimprich et al, 1996) and DNA-PKcs.

Such molecules may be identified by various means. For instance, information may be obtained about residues which are important for p53 phosphorylation by ATM using alanine scanning and deletion analysis of p53 and/or peptide fragments, for instance the N-terminal 42 amino acids or so of p53, or a fragment of around 10 amino acids including the relevant site of phosphorylation. Mutation may be used to identify residues which affect phosphorylation and those which do not. When key residues are identified, computer sequence databases may be scanned for proteins including the same or similar pattern of residues, taking into account conservative variation in sequence (see below) as appropriate. Candidate molecules may then be used in one or more assays for phosphorylation by ATM (such as discussed below).

Identification of key residues for phosphorylation at any of the sites in p53 phosphorylated by ATM may also be used in the design of peptide and non-peptidyl agents which modulate, particularly inhibit, phosphorylation of p53 by ATM, as discussed further below.

Methods of obtaining agents able to modulate interaction between ATM and p53 (or, it must be remembered, ATR, or a related protein having a similar associated kinase activity, and other molecules including a phosphorylation site homologous to one of those phosphorylated in p53 by ATM) include methods wherein a suitable end-point is used to assess interaction in the presence and absence of a test substance. Assay systems may be used to determine ATM kinase activity, ATM DNA binding and/or ATM interaction with one or more other molecules. For phosphorylation assays, full-length p53, truncated portions of p53, or portions of p53 fused to other proteins (eg. GST), or a suitable variant or derivative of any of these may be used. Peptide phosphorylation assays may be developed using peptides that correspond to the phosphorylated regions of p53. The phosphorylation of any of the above may be assayed by any of a variety of procedures such as discussed below and may be adapted to high throughput screening approaches. Interference of DNA binding may be assayed but the inhibition of kinase activity may be more sensitive and identify a greater breadth of inhibitors to DNA binding inhibition, and so may be preferred by the skilled operator of the present invention.

ATM kinase activity may be assayed for either of the two N-terminal p53 sites. When assaying for phosphorylation, DNA is preferably included in the assay system. Related but different screens may be set up for inhibitors and activators of the two sites of ATM-mediated phosphorylation event.

Generally of most interest is modulation of the phosphorylation of p53 (or other molecule) by ATM. Detailed disclosure in this respect is included below. It is worth noting, however, that combinatorial library technology provides an efficient way of testing a potentially vast number of different substances for ability to modulate an interaction with and/or activity of a polypeptide. Such libraries and their use are known in the art, for all manner of natural products, small molecules and peptides, among others. The use of peptide libraries may be preferred in certain circumstances.

At the cellular level, A-T cells display chromosomal instability, radiosensitivity, are impaired in p53 induction following treatment with ionising radiation, and show altered regulation of transcription factor NFkB. Thus, the wild-type ATM gene functions as a tumour suppressor, and is a suppressor of neurological degeneration and other degenerative states commonly associated with ageing.

Given the results reported herein on which the present invention is based, activators and inhibitors of ATM-associated kinase activity may be identified and appropriate agents may be obtained, designed and used for any of a variety of purposes:

A-T Therapy. Activators of ATM or ATR function may prove to have utility in treating humans with A-T (discussed further below).

Modulation of immune system function. A-T patients display immunodeficiencies, demonstrating that ATM is required for generation of a fully functional immune system. Modulators of ATM or ATR may, therefore, be used in regulating immune system function.

AIDS therapy. It has been shown that the lymphocytes of humans entering the final stages of AIDS have shortened telomeres and this may contribute to them being no longer able to replenish the immune system. Cells of A-T patients lose their telomeres more quickly than those of normal individuals, revealing that ATM plays a positive role in telomere length homeostasis. Activators of ATM function may, therefore, find utility in treatment of individuals with AIDS through lengthening the telomeres of senescent lymphocytes in these individuals, thus allowing replenishment of the immune system.

p53 therapy. The identification of the site of p53 phosphorylated by ATM indicates that this of extreme regulatory importance. Indeed, the N-terminal sites on p53 phosphorylated by ATM reside within the region known as "conserved region I" that has been shown to function together with flanking sequences in the interaction with the protein Mdm-2 (see Kussie et al 1996; Picksley et al., 1994; Momand et al., 1992; Chen et al., 1993 and references therein). Mdm-2 serves as a negative regulator of p53 by two mechanisms. First, it masks the p53 transcriptional activation domain, stopping p53 activating genes (Momand et al., 1992). Second, Mdm-2 has been shown recently to target p53 for degradation within the cell (Kubbutat et al., 1997; Haupt et al., 1997). Our data therefore provide an indication that phosphorylation of p53 by ATM will disrupt its interactions with Mdm-2, thus resulting in increased levels of transcriptionally active p53. This knowledge may, therefore, be utilised to generate novel therapeutic agents that target p53—such as small molecules that, through binding to mutant p53, mimic ATM-mediated activation of this molecule.

Phosphorylation at any one or more of these sites may affect interaction of p53 with a number of proteins. Mdm2 is one particularly example given the location of Thr18 within the site on p53 to which Mdm2 binds (see e.g. Chen et al., (1993), Kussie et al., (1996), Picksley et al., (1994) and Momand et al., (1992) for characterisation of this interaction) and Ser15 which lies immediately adjacent to the minimal Mdm2 binding sequence. Indeed, a report by Shieh et al published in October 1997 indicates that phosphorylation at Ser15 can disrupt the p53-Mdm2 interaction. Phosphorylation of p53 may be used to affect interaction of p53 with any of a number of other proteins, including CBP (Gu et al.; Lill et al.), adenovirus E1B protein, which binds within the amino terminal 123 amino acids of p53 (Kao et al., 1990), with residues Leu-22 and Trp-23 playing an important role (Lin et al., 1994), transcription factors XPD (Rad3) and XPB, as well as CSB involved in strand-specific DNA repair (Wang et al., 1995), TFIIH (Xiao et al., 1994), E2F1 and DP1 (O'Connor et al., 1995), Cellular Replication Protein A (Li and Botchan, 1993), replication factor RPA (Dutta et al., 1993), WT1 (Maheswaran et al., 1993), TATA-binding protein (Seto et al., 1992, Truant et al., 1992, Martin et al., 1993), and TAF(II)40 and TAF(II)60 (Thut et al., 1995).

An assay according to the present invention as discussed further below may determine the role of phosphorylation of p53 by ATM on any of these interactions and an agent found to be able to modulate such phosphorylation may be used to disrupt or promote any of these interactions, e.g. in a therapeutic context.

Modulating telomere length. A-T cells show accelerated rates of telomere shortening (Metcalfe et al., 1996, *Nature Genetics* 13, 350–353). Thus, regulators of ATM activity may be used to control telomere length. ATM does not appear to be part of the telomerase enzyme itself (Metcalfe et al. shows that telomerase levels are normal in A-T cells; also, our data and the data of Pandita et al. 1995 show that A-T cells have somewhat shortened telomeres but do not have repressed levels of telomerase). Thus, ATM works not as part of telomerase but as part of a telomere length homeostatic mechanism. It is therefore likely that anti-ATM drugs will work synergistically with anti-telomerase drugs.

Ageing. A-T patients display enhanced rates of ageing, display a number of symptoms associated with increased age (neurological deterioration, cancers, immunological deficiencies etc), and their cells show shortened lifespan in culture. Agents that modulate ATM activity may therefore be used to treat/prevent disease states associated with premature and normal ageing.

Tumour/Cancer therapy. This is discussed below. Drugs that modulate ATM action may be used to treat A-T patients; treat cancer—through affecting cellular growth capacity by shortening cells telomeres; manipulate the immune system—A-T patients are somewhat immunodeficient; treat cancer—radiosensitization of tumours etc (see below). Also, ATM modulators may be used to limit cell growth potential by affecting telomere length etc. The linkage to p53 may allow p53 therapy, activating p53 in cancer cells, which may lead to cell growth arrest and/or cell death via apoptosis or another route.

Activators of ATM (or ATR, DNA-PK or related kinases) may be used, for example, to inhibit cell proliferation by activating cell cycle checkpoint arrest in the absence of cellular damage, which may be used in the treatment of tumours, cancer, psoriasis, arteriosclerosis and other hyperproliferative disorders. Activators may be employed to activate p53 in cells without damaging the cells. Cells of a patient may be treated so that normal cells (p53+) stop growing and are thus refractory to killing by administration of a drug that kills cells via interfering with cell division or DNA replication, while tumour cells (many of which are p53 negative) do not arrest and are consequently selectively killed by the aforementioned agents. By way of example, ATM activators include peptides capable of recognising and binding to both ATM and p53 but which do not interfere with the phosphorylation of the Ser15 and Thr18 sites of p53, or substances capable of activating ATM in a similar manner to the activation observed using DNA.

Cancer radiotherapy and chemotherapy may be augmented using agents in accordance with the present invention. Ionising radiation (IR) and radiomimetic drugs are used commonly to treat cancers, and kill cancer cells predominantly via inflicting DNA damage. Cells deficient in ATM are hypersensitive to ionising radiation and radiomimetics. Thus, inhibitors of the ATM will hypersensitise cells to the killing effects of ionising radiation and radiomimetics. ATM inhibitors may thus be used as adjuncts in cancer radiotherapy and chemotherapy.

Cell growth capacity may be modulated e.g. in treatment of cancer, ageing, and AIDS. It is established that ATM plays a crucial role in controlling the length of telomeric chromosomal ends (Metcalfe et al.). Telomeric ends in most normal cell types shorten at each cell division, and cells with excessively shortened telomeres are unable to divide. Thus, telomeres are thought to function as a "division counting apparatus" that limits the proliferative capacity of most normal mammalian cells. Inhibitors of ATM function may, therefore, have utility in preventing cancer progression by limiting the growth potential of cancerous or pre-cancerous cells. Activators of ATM may be used to release senescent cells from growth arrest and may thus have utility in treatments of aged individuals. In addition, it has been shown recently that the lymphocytes of humans entering the final stages of AIDS have shortened telomeres and this may contribute to these cells being no longer able to proliferate and replenish the immune system. ATM activators may, therefore, result in lengthening of the telomeres of such cells and restoring their proliferative capacity.

Interaction between ATM and p53 may be inhibited by inhibition of the production of the relevant protein. For instance, production of one or more of these components may be inhibited by using appropriate nucleic acid to influence expression by antisense regulation. The use of anti-sense genes or partial gene sequences to down-regulate gene expression is now well-established. Double-stranded DNA is placed under the control of a promoter in a "reverse orientation" such that transcription of the "anti-sense" strand of the DNA yields RNA which is complementary to normal mRNA transcribed from the "sense" strand of the target gene. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works.

Another possibility is that nucleic acid is used which on transcription produces a ribozyme, able to cut nucleic acid at a specific site—thus also useful in influencing gene expression. Background references for ribozymes include Kashani-Sabet and Scanlon, 1995, *Cancer Gene Therapy*, 2(3): 213–223, and Mercola and Cohen, 1995, *Cancer Gene Therapy*, 2(1), 47–59.

Thus, various methods and uses of modulators, which inhibit or potentiate interaction of ATM and p53, particularly phosphorylation of p53 by ATM, are provided as further aspects of the present invention. The purpose of disruption, interference with or modulation of interaction between ATM and p53, particularly the phosphorylation of p53 by ATM may be to modulate any activity mediated by virtue of such interaction, as discussed above and further below.

Various aspects of the present invention relate to modulation of interaction between ATM and DNA. Such interaction is established here we believe for the first time, and is further shown to have an effect on p53 phosphorylation by ATM. It was surprising that ATM is a DNA binding protein, as there are data suggesting that it is associated with microsomal membranes in the cytoplasm (Watters et al, 1997 and Brown et al, 1997; show ATM is also present in cytoplasmic vesicles) and A-T cells have also been reported to be defective in signalling from the cell membrane in B- and T-cells (see above). It was furthermore surprising that ATM would bind DNA so well. The purification method used and described below does not purify a variety of other (known) DNA binding factors, yet ATM is purified very selectively (about 100-fold in a single step) using a DNA affinity chromatography procedure.

The present invention provides in one aspect the use of DNA for purifying ATM or ATR. In further aspects, the present invention provides for the use of DNA in assays for activity of ATM or ATR, particularly phosphorylation of p53 (or other molecule).

We have also purified ATM and ATR via another surprising route, using nitrilo-tri-acetic acid (NTA) agarose. NTA has 4 chelating sites for $Ni^{2+}$. Another $Ni^{2+}$ matrix, imino-diacetic acid (IDA) agarose (with 3-chelating sites for $Ni^{2+}$) we have found to bind ATM only weakly. These $Ni^{2+}$ matrices are generally used interchangeably to purify proteins that chelate metal ions, usually, via a run of His residues (usually 6 give best binding). ATM does not have a run of 6, 5 or even 4 His residues, so it is surprising that ATM or ATR is purifiable by the Ni-linked columns. Furthermore, since the two matrices are generally used interchangeably, it is further surprising that ATM binds to the NTA well but only poorly to the IDA matrix.

ATM no doubt works in concert with other factors in the detection and signalling of DNA damage. Indeed, although our data reveal that ATM possesses intrinsic DNA-stimulated p53 kinase function, we have observed repeatedly that the presence of additional polypeptides correlates with increased ATM activity. Thus, our most highly purified preparations have considerably less activity than preparations containing an equivalent amount of ATM but also possessing additional co-purifying polypeptides. It is likely that these serve to help tether ATM to the DNA and/or trigger its kinase activity by altering the conformation of the ATM polypeptide. Accordingly, references to ATM, or a protein having a associated kinase activity, include both purified ATM (or the related protein) and ATM (or the related protein) in combination with associated polypeptides or co-factors present in preparations as obtainable by the methods described herein.

Assays according to the present invention may be used in the identification of such additional polypeptides, for example by assaying for protein fractions that stimulate ATM activity. The use of ATM or ATR in identifying and/or obtaining cofactors which (e.g. naturally) enhance its kinase activity is further provided by the present invention. ATM activity may under certain circumstances be masked by one or more factors (see discussion section below). Accordingly, the present invention also provides for the use of ATM in identifying and/or obtaining such factors.

Protein or other co-factors of ATM, e.g. which enhance ATM kinase activity, may be used in the design of inhibitors of this, providing another route for modulating ATM activity. This may similarly be used to provide a route to deriving agents that activate ATM, e.g. by inhibiting one or more repressors of ATM activity.

BRIEF DESCRIPTION OF THE FIGURES

FIG. 2: Purification of ATM from HeLa cell nuclear extract. (A) ATM Purification strategy. HeLa nuclear extract was subjected to ion exchange chromatography using Q-Sepharose and peak ATM fractions, eluting between 160–200 mM KCl, were passed over heparin-agarose ion exchange resin. ATM fractions eluting from heparin-agarose between 200–220 mM KCl were pooled and subjected to DNA affinity purification and elution from DNA-bearing beads at 500 mM KCl resulting in an essentially homogeneous preparation of ATM. (B) Purification of ATM to essential homogeneity. Equivalent volumes (5 μl) of HeLa cell nuclear extract (50 μg protein), or pooled fractions following Q-sepharose, Heparin-agarose or DNA affinity chromatography were subjected to 7% SDS-PAGE and proteins visualised by silver staining (upper panel). Fractions were also subjected to Western blot analysis (lower panel) using antibodies raised against ATM, DNA-PK$_{CS}$, Ku70 plus Ku80 or the 70 kDa subunit of RPA, as indicated.

FIG. 6a shows the amino acid sequence of human ATM, with the kinase domain marked by underlining. FIG. 6b shows the ATM nucleic acid sequence with the initiation codon underlined.

FIG. 7a shows the amino acid sequence of human p53 (SEQ ID NO:3) with residues phosphorylated by ATM marked by underlining. FIGS. 7b i–ii show the p53 nucleic acid sequence (SEQ ID NO:4) with the initiation codon underlined.

FIG. 8a shows the amino acid sequence of human ATR (FRP-1) (SEQ ID NO:5). FIGS. 8b i–vi show the ATR nucleic acid sequence (SEQ ID NO:6) with the initiation codon underlined.

FIGS. 9a i–ii show the amino acid sequence of DNA-PKcs (SEQ ID NO:7). FIGS. 9b i–vii show the DNA-PK nucleic acid sequence (SEQ ID NO:8) with the initiation codon underlined.

Figure 1:
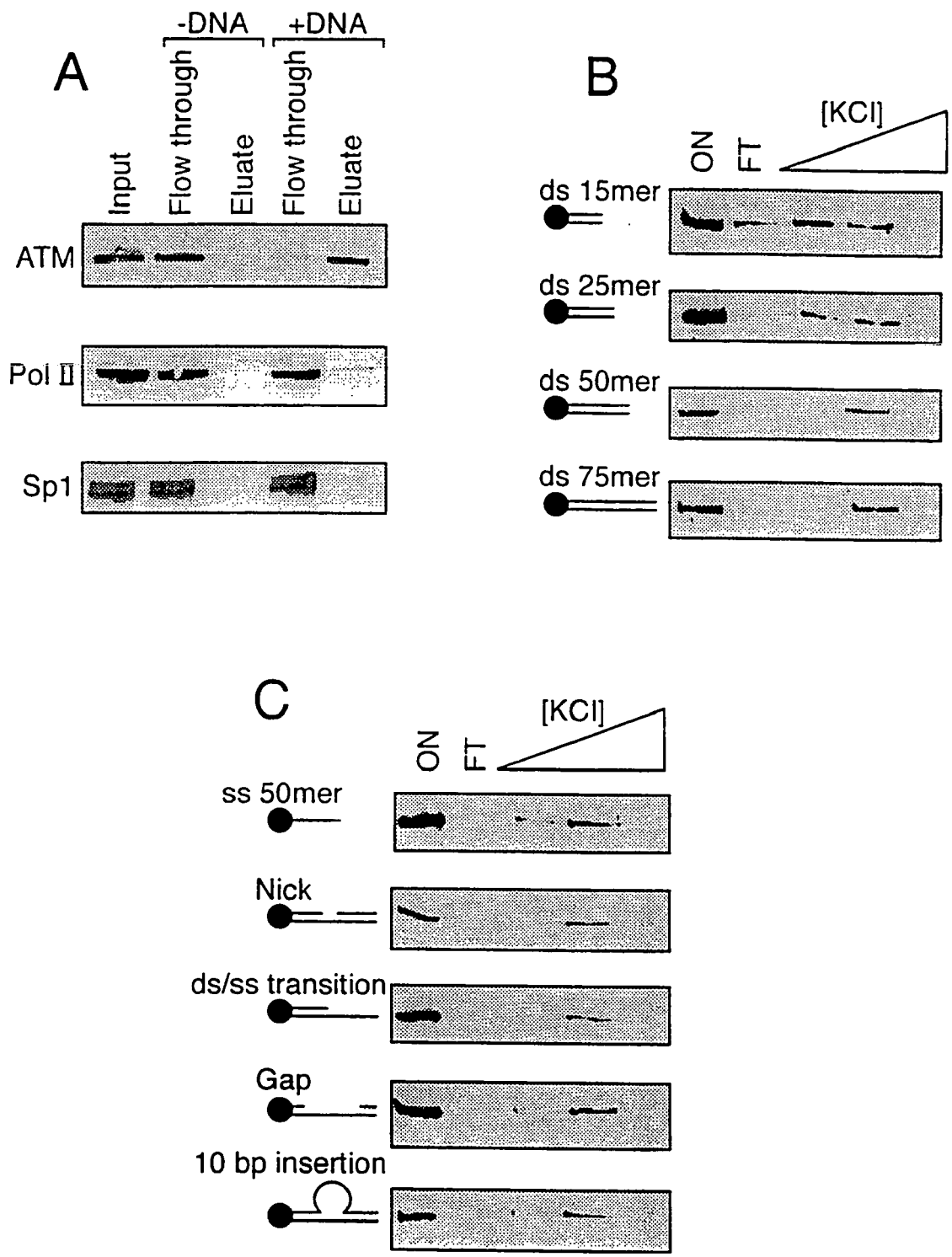
FIG. 1: ATM binds to DNA. (A) ATM binds to a dsDNA oligonucleotide. HeLa nuclear extract was bound to either streptavidin iron oxide beads (−DNA) or streptavidin iron oxide beads bearing a 50-mer ds DNA oligonucleotide (+DNA). After extensive washing, ATM was eluted from DNA in 500 mM KCl. Eluted proteins were subjected to 7% SDS-PAGE and ATM visualised by Western blotting using ATM.B antiserum. (B) Binding of ATM is dependent on DNA length. ATM enriched extract was bound to streptavidin iron oxide beads attached to ds DNA of various sizes (15, 25, 50 or 75 bp). After extensive washing, ATM was eluted by sequential washes with 100, 250 and 500 mM KCl. Eluates were analysed as in (A). (C) ATM binds DNA containing a variety of different architectures. ATM enriched extract was bound to streptavidin iron oxide beads bound to either ss or ds DNA containing a nick, ds/ss transition, gap or 10 bp insertion. Washing, elution and ATM detection was as in (B).

The present invention in various aspects provides for modulating, interfering with or interrupting, increasing or potentiating interaction between the ATM protein and p53, particularly phosphorylation of p53 by ATM, using an appropriate agent. As noted, it having now been established for the first time that ATM is a protein kinase, it is highly likely to act on other molecules, particularly proteins including a site which is homologous to one of the sites in p53 phosphorylated by ATM. The present invention further extends to the use of proteins having an associated kinase activity similar to ATM, especially DNA-PK and ATR. The present invention extends to modulation of such phosphorylation and this should be borne in mind when considering the disclosure herein which for convenience uses p53 for illustrative purposes, and as a preferred embodiment in certain contexts.

An agent capable of modulating interaction between ATM and p53 may be capable of blocking interaction between a site located within amino acid residues including Ser15 or Thr18.

In addition to interacting at the site of phosphorylation of p53, ATM and p53 may interact at one or more other sites within either or both proteins. Affecting interaction at such a site may have an effect on phosphorylation of p53 by ATM. Various fragments and derivatives of the proteins, particular of p53, may be used to analyse this, using techniques such as alanine scanning and deletion analysis. The present invention encompasses modulation of interaction between ATM and p53 at any site, preferably resulting in modulation of p53 phosphorylation by ATM.

The full amino acid sequence of the ATM protein has been elucidated and is set out in Savitsky et al 1995a, 1995b, and FIG. 6a, of which the amino acid residue numbering is used. The kinase domain is marked in FIG. 6a. The p53 amino acid sequence is shown in FIG. 7a, of which the amino acid residue numbering is used. These sequences are human sequences. ATM and p53 are conserved among vertebrates, particular mammals—see e.g. FIG. 2 of Soussi et al. For p53 conservation in the regions of the residues shown herein to be phosphorylated by ATM—so the present invention extends to use in any of its aspects of other vertebrate, particularly mammalian, p53 and/or ATM, e.g. primate, such as monkey, rodent, such as mouse or rat, pig, horse, cow, sheep, goat, dog, cat, and so on. The amino acid and nucleic acid sequences of ATR (also known as FRP1) are set out in Cimpich et al, 1996. The amino acid sequence is reproduced as FIG. 8a. The amino acid sequence of DNA-PK is provided in Hartley et al, 1995 and is set out in FIG. 9a. The nucleic acid sequences of these proteins are also included as FIGS. 6b, 7b, 8b and 9b.

Agents useful in accordance with the present invention may be identified by screening techniques which involve determining whether an agent under test inhibits or disrupts the interaction of ATM protein or a suitable fragment thereof (e.g. including amino acid residues of the kinase domain, as marked on FIG. 6, or a smaller fragment of any of these regions) of ATM, with p53 or a fragment thereof, or a suitable analogue, fragment or variant thereof. One class of preferred fragments of p53 are those which include one or both of the phosphorylation sites at Ser15 or Thr18.

Suitable fragments of ATM or p53 include those which include residues which interact with the counterpart protein. Smaller fragments, and analogues and variants of this fragment may similarly be employed, e.g. as identified using techniques such as deletion analysis or alanine scanning.

Thus, the present invention provides a peptide fragment of ATM which is able to interact with p53 and/or inhibit interaction between ATM and p53, particularly phosphorylation of p53 by ATM, and provides a peptide fragment of p53 which is able to interact with ATM and/or inhibit interaction between p53 and ATM, particularly phosphorylation of p53 by ATM, such peptide fragments being obtainable by means of deletion analysis and/or alanine scanning of the relevant protein—making an appropriate mutation in sequence, bringing together a mutated fragment of one of the proteins with the other or a fragment thereof and determining interaction, preferably phosphorylation of p53 or fragment thereof. In preferred embodiments, the peptide is short, as discussed below, and may be a minimal portion that is able to interact with the relevant counterpart protein and/or inhibit the relevant interaction.

Screening methods and assays are discussed in more detail below.

One class of agents that can be used to disrupt the interaction of ATM and p53 are peptides based on the sequence motifs of ATM or p53 that interact with counterpart p53 or ATM (as discussed already above). Such peptides tend to be short, and may be about 40 amino acids in length or less, preferably about 35 amino acids in length or less, more preferably about 30 amino acids in length, or less, more preferably about 25 amino acids or less, more preferably about 20 amino acids or less, more preferably about 15 amino acids or less, more preferably about 10 amino acids or less, or 9, 8, 7, 6, 5 or less in length. The present invention also encompasses peptides which are sequence variants or derivatives of a wild type ATM or p53 sequence, but which retain ability to interact with p53 or ATM (respectively, as the case may be) and/or ability to modulate interaction between ATM and p53, particularly phosphorylation of p53 by ATM.

Instead of using a wild-type ATM or p53 fragment, a peptide or polypeptide may include an amino acid sequence which differs by one or more amino acid residues from the wild-type amino acid sequence, by one or more of addition, insertion, deletion and substitution of one or more amino acids. Thus, variants, derivatives, alleles, mutants and homologues, e.g. from other organisms, are included.

Preferably the amino acid sequence shares homology with a fragment of the relevant ATM or p53 fragment sequence shown preferably at least about 30%, or 40%, or 50%, or 60%, or 70%, or 75%, or 80%, 90%, or 95% homology. Thus, a peptide fragment of ATM or p53 may include 1, 2, 3, 4, 5, greater than 5, or greater than 10 amino acid alterations such as substitutions with respect to the wild-type sequence. Preferably the peptide fragments of ATM are based on the sequence of all or part of the kinase domain as shown in FIG. 6. Preferably, the p53 fragments are based on the N-terminal sequence of the molecule around the sites phosphorylated by ATM, i.e. comprising the amino acid motif (SEQ ID NO:9) PPLSQETFSD, or more generally, the motif (SEQ ID NO:10) SxxT, where x is any amino acid.

A derivative of a peptide for which the specific sequence is disclosed herein may be in certain embodiments the same length or shorter than the specific peptide. In other embodiments the peptide sequence or a variant thereof may be included in a larger peptide, as discussed above, which may or may not include an additional portion of ATM or p53. 1, 2, 3, 4 or 5 or more additional amino acids, adjacent to the relevant specific peptide fragment in ATM or p53, or heterologous thereto may be included at one end or both ends of the peptide.

(It should not be forgotten that references to ATM and p53 apply equally to ATM and related proteins such as ATR and DNA-PK and other proteins including a phosphorylation site homologous to one in p53 phosphorylated by ATM.)

As is well-understood, homology at the amino acid level is generally in terms of amino acid similarity or identity. Similarity allows for "conservative variation", i.e. substitution of one hydrophobic residue such as isoleucine, valine, leucine or methionine for another, or the substitution of one polar residue for another, such as arginine for lysine, glutamic for aspartic acid, or glutamine for asparagine. Similarity may be as defined and determined by the TBLASTN program, of Altschul et al. (1990) *J. Mol. Biol.* 215: 403–10, which is in standard use in the art. Homology may be over the full-length of the relevant peptide or over a contiguous sequence of about 5, 10, 15, 20, 25, 30, 35, 50, 75, 100 or more amino acids, compared with the relevant wild-type amino acid sequence.

As noted, variant peptide sequences and peptide and non-peptide analogues and mimetics may be employed, as discussed further below.

Various aspects of the present invention provide a substance, which may be a single molecule or a composition including two or more components, which includes a peptide fragment of ATM or p53 which includes a sequence as recited in FIG. 6 or FIG. 7, particularly within the ATM kinase domain marked in FIG. 6, a peptide consisting essentially of such a sequence, a peptide including a variant, derivative or analogue sequence, or a non-peptide analogue or mimetic which has the ability to interact with ATM or p53 and/or modulate, disrupt or interfere with interaction between ATM or p53.

Variants include peptides in which individual amino acids can be substituted by other amino acids which are closely related as is understood in the art and indicated above.

Non-peptide mimetics of peptides are discussed further below.

As noted, a peptide according to the present invention and for use in various aspects of the present invention may include or consist essentially of a fragment of ATM or p53 as disclosed, such as a fragment whose sequence is shown in FIG. 6 or FIG. 7, respectively. Where one or more additional amino acids are included, such amino acids may be from ATM or p53 or may be heterologous or foreign to ATM or p53. A peptide may also be included within a larger fusion protein, particularly where the peptide is fused to a non-ATM or p53 (i.e. heterologous or foreign) sequence, such as a polypeptide or protein domain.

The invention also includes derivatives of the peptides, including the peptide linked to a coupling partner, e.g. an effector molecule, a label, a drug, a toxin and/or a carrier or transport molecule, and/or a targeting molecule such as an antibody or binding fragment thereof or other ligand. Techniques for coupling the peptides of the invention to both peptidyl and non-peptidyl coupling partners are well known in the art. In one embodiment, the carrier molecule is a 16 aa peptide sequence derived from the homeodomain of Antennapedia (e.g. as sold under the name "Penetratin"), which can be coupled to a peptide via a terminal Cys residue. The "Penetratin" molecule and its properties are described in WO 91/18981.

Peptides may be generated wholly or partly by chemical synthesis. The compounds of the present invention can be readily prepared according to well-established, standard liquid or, preferably, solid-phase peptide synthesis methods, general descriptions of which are broadly available (see, for example, in J. M. Stewart and J. D. Young, Solid Phase Peptide Synthesis, 2nd edition, Pierce Chemical Company, Rockford, Ill. (1984), in M. Bodanzsky and A. Bodanzsky, The Practice of Peptide Synthesis, Springer Verlag, New York (1984); and Applied Biosystems 430A Users Manual, ABI Inc., Foster City, Calif.), or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a peptidyl molecule according to the present invention (peptide or polypeptide) is to express nucleic acid encoding it, by use of nucleic acid in an expression system.

Accordingly the present invention also provides in various aspects nucleic acid encoding the polypeptides and peptides of the invention.

Generally, nucleic acid according to the present invention is provided as an isolate, in isolated and/or purified form, or free or substantially free of material with which it is naturally associated, such as free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding a polypeptide or peptide in accordance with the present invention can be readily prepared by the skilled person using the information and references contained herein and techniques known in the art (for example, see Sambrook, Fritsch and Maniatis, "Molecular Cloning, A Laboratory Manual", Cold Spring Harbor Laboratory Press, 1989, and Ausubel et al, Short Protocols in Molecular Biology, John Wiley and Sons, 1992), given the nucleic acid sequence and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding ATM or p53 fragments may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially available expression system. Another recombinant approach is to amplify the relevant portion of the DNA with suitable PCR primers. Modifications to the ATM or p53 sequences can be made, e.g. using site directed mutagenesis, to lead to the expression of modified ATM or p53 peptide or to take account of codon preference in the host cells used to express the nucleic acid.

In order to obtain expression of the nucleic acid sequences, the sequences can be incorporated in a vector having one or more control sequences operably linked to the nucleic acid to control its expression. The vectors may include other sequences such as promoters or enhancers to drive the expression of the inserted nucleic acid, nucleic acid sequences so that the polypeptide or peptide is produced as a fusion and/or nucleic acid encoding secretion signals so that the polypeptide produced in the host cell is secreted from the cell. Polypeptide can then be obtained by transforming the vectors into host cells in which the vector is functional, culturing the host cells so that the polypeptide is produced and recovering the polypeptide from the host cells or the surrounding medium. Prokaryotic and eukaryotic cells are used for this purpose in the art, including strains of *E. coli*, yeast, and eukaryotic cells such as COS or CHO cells.

Thus, the present invention also encompasses a method of making a polypeptide or peptide (as disclosed), the method including expression from nucleic acid encoding the polypeptide or peptide (generally nucleic acid according to the invention). This may conveniently be achieved by growing a host cell in culture, containing such a vector, under appropriate conditions which cause or allow expression of the polypeptide. Polypeptides and peptides may also be expressed in in vitro systems, such as reticulocyte lysate.

Systems for cloning and expression of a polypeptide in a variety of different host cells are well known. Suitable host cells include bacteria, eukaryotic cells such as mammalian and yeast, and baculovirus systems. Mammalian cell lines available in the art for expression of a heterologous polypeptide include Chinese hamster ovary cells, HeLa cells, baby hamster kidney cells, COS cells and many others. A common, preferred bacterial host is *E. coli*.

Suitable vectors can be chosen or constructed, containing appropriate regulatory sequences, including promoter sequences, terminator fragments, polyadenylation sequences, enhancer sequences, marker genes and other sequences as appropriate. Vectors may be plasmids, viral e.g. phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, 1992.

Thus, a further aspect of the present invention provides a host cell containing heterologous nucleic acid as disclosed herein.

The nucleic acid of the invention may be-integrated into the genome (e.g. chromosome) of the host cell. Integration may be promoted by inclusion of sequences which promote recombination with the genome, in accordance with standard techniques. The nucleic acid may be on an extra-chromosomal vector within the cell, or otherwise identifiably heterologous or foreign to the cell.

A still further aspect provides a method which includes introducing the nucleic acid into a host cell. The introduction, which may (particularly for in vitro introduction) be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. As an alternative, direct injection of the nucleic acid could be employed.

Marker genes such as antibiotic resistance or sensitivity genes may be used in identifying clones containing nucleic acid of interest, as is well known in the art.

The introduction may be followed by causing or allowing expression from the nucleic acid, e.g. by culturing host cells (which may include cells actually transformed although more likely the cells will be descendants of the transformed cells) under conditions for expression of the gene, so that the encoded polypeptide (or peptide) is produced. If the polypeptide is expressed coupled to an appropriate signal leader peptide it may be secreted from the cell into the culture medium. Following production by expression, a polypeptide or peptide may be isolated and/or purified from the host cell and/or culture medium, as the case may be, and subsequently used as desired, e.g. in the formulation of a composition which may include one or more additional components, such as a pharmaceutical composition which includes one or more pharmaceutically acceptable excipients, vehicles or carriers (e.g. see below).

Introduction of nucleic acid encoding a peptidyl molecule according to the present invention may take place in vivo by way of gene therapy, to disrupt or interfere with interaction between ATM or p53

Thus, a host cell containing nucleic acid according to the present invention, e.g. as a result of introduction of the nucleic acid into the cell or into an ancestor of the cell and/or genetic alteration of the sequence endogenous to the cell or ancestor (which introduction or alteration may take place in vivo or ex vivo), may be comprised (e.g. in the soma) within an organism which is an animal, particularly a mammal, which may be human or non-human, such as rabbit, guinea pig, rat, mouse or other rodent, cat, dog, pig, sheep, goat, cattle or horse, or which is a bird, such as a chicken. Genetically modified or transgenic animals or birds comprising such a cell are also provided as further aspects of the present invention.

This may have a therapeutic aim. (Gene therapy is discussed below). Also, the presence of a mutant, allele, derivative or variant sequence within cells of an organism, particularly when in place of a homologous endogenous sequence, may allow the organism to be used as a model in testing and/or studying substances which modulate activity of the encoded polypeptide in vitro or are otherwise indicated to be of therapeutic potential. Knock-out mice, for instance, may be used to test for radiosensitivity. Conveniently, however, at least preliminary assays for such substances may be carried out in vitro, that is within host cells or in cell-free systems. Where an effect of a test compound is established on cells in vitro, those cells or cells of the same or similar type may be grafted into an appropriate host animal for in vivo testing.

For instance, p53 function or activity may be measured in an animal system such as a tumour model, e.g. involving a xenograft, relying on active p53. The animal may be subject to radio- or chemo-therapy and a test substance administered. An augmentation of the reaction in the animal to the radio- or chemo-therapy may be indicative of blocking of ATM phosphorylation of p53. Suitable screening methods are conventional in the art. They include techniques such as radioimmunosassay, scintillation proximetry assay and ELISA methods. Suitably either the ATM protein or fragment or p53 or fragment, or an analogue, derivative, variant or functional mimetic thereof, is immobilised whereupon the other is applied in the presence of the agents under test. In a scintillation proximetry assay, a biotinylated protein fragment may be bound to streptavidin coated scintillant— impregnated beads (produced by Amersham). Binding of radiolabelled peptide is then measured by determination of radioactivity induced scintillation as the radioactive peptide binds to the immobilized fragment. Agents which intercept this are thus inhibitors of the interaction. Further ways and means of screening for agents which modulate interaction between ATM and p53 are discussed below.

In one general aspect, the present invention provides an assay method for a substance with ability to modulate, e.g. disrupt or interfere with interaction between ATM and p53, the method including:

(a) bringing into contact a substance according to the invention including a peptide fragment of ATM, or a protein having an associated kinase activity, or a derivative, variant or analogue thereof as disclosed, a substance including the relevant fragment of p53 or a variant, derivative or analogue thereof.

A test compound which disrupts, reduces, interferes with or wholly or partially abolishes interaction between said substances (e.g. including a ATM fragment and including a p53 fragment), and which may modulate ATM and/or p53 activity, may thus be identified.

Agents which increase or potentiate interaction between the two substances may be identified using conditions which, in the absence of a positively-testing agent, prevent the substances interacting.

Another general aspect of the present invention provides an assay method for a substance able to interact with the relevant region of ATM or p53 as the case may be, the method including:

(a) bringing into contact a substance which includes a peptide fragment of ATM or a protein having an associated kinase activity which interacts with p53 as disclosed, or which includes a peptide fragment of p53 which interacts with ATM or a protein having an associated kinase activity, or a variant, derivative or analogue of such peptide fragment, as disclosed, and a test compound; and, (b) determining interaction between said substance and the test compound.

A test compound found to interact with the relevant portion of ATM may be tested for ability to modulate, e.g. disrupt or interfere with, ATM interaction with p53 and/or ability to affect p53 and/or ATM activity or other activity mediated by ATM or p53 as discussed already above.

Similarly, a test compound found to interact with the relevant portion of p53 may be tested for abiliy to modulate, e.g. disrupt or interfere with, p53 interaction with ATM and/or ability to affect ATM and/or p53 activity or other activity mediated by p53 or ATM as discussed elsewhere herein.

Another general aspect of the present invention provides an assay method for a substance able to affect p53 activity, the method including:

(a) bringing into contact p53 and a test compound; and, (b) determining p53 activity.

p53 activity may be determined in the presence and absence of ATM to allow for an effect of a test compound on activity to be attributed to an effect on interaction between p53 and ATM, preferably phosphorylation of p53 by ATM (discussed further below).

p53 activities which may be determined include induction of expression of a protein such as p21 (WAF1), cellular sensitivity to ionizing radiation, p53-induced apoptosis activity, p53-induced anti-proliferative activity, p53-induced senescence of cells In assaying for agents able to modulate phosphorylation of p53 by ATM, suitable fragments of p53 may be employed including any of the sites of such phosphorylation. Where it is desired to determine phosphorylation at the Ser15 and/or Thr18 site, DNA will generally be included in the assay system to stimulate the requisite kinase activity of ATM. As noted, the present invention extends also to non-human p53 and phosphorylation at sites equivalent to those of human p53 identified herein. Thus, the assays may employ derivatives of full length p53 or the p53 fragments including the phosphorylation sites at Ser15 and/or Thr18.

The present invention further provides the use of DNA for stimulating phosphorylation of p53 by ATM, e.g. in an assay but also in many other contexts. Such phosphorylation may include at the Ser15 and/or Thr18 site of human p53 or equivalent site in p53 of another species, particularly of a vertebrate such as a mammal.

An assay according to the present invention may include an inhibitor of DNA-PKcs kinase activity, to avoid complications of redundant phosphorylation by that kinase. Such an inhibitor of DNA-PKcs kinase activity might not affect ATM kinase activity.

Further assays according to the present invention are for agents which modulate DNA binding by ATM. Inhibitors and/or activators may be screened using appropriate conditions for determination of DNA binding by ATM.

Thus, a further aspect of the present invention provides an assay method for a compound able to affect DNA binding by ATM or a protein having an associated kinase activity, the method including:

(a) bringing into contact a substance which is ATM or a protein having an associated kinase activity, or a fragment, variant or derivative thereof able to bind DNA, DNA and a test compound, under conditions wherein, in the absence of the test compound being an inhibitor of DNA binding by ATM or the protein having an associated kinase activity, said substance binds said DNA; and, (b) determining binding between said substance and said DNA.

Activators of DNA binding by ATM may similarly be identified using an assay method wherein said substance, the DNA and the test compound are brought together under conditions wherein in the absence of the test compound being a potentiator of DNA binding by ATM, the substance does not bind the DNA. Activators include substances which activate ATM associated kinase activity in the absence of DNA or substances which enhance the interaction of ATM and p53, both of which may allow the induction of a p53 response in the absence of DNA damage, e.g. as caused by irradiation.

DNA binding may be determined using any suitable technique, including an electrophoretic mobility shift assay (EMSA), UV protein-DNA crosslinking, chemical or DNaseI footprinting, and so on.

Determination of DNA binding by ATM may be performed in conjunction with determination of phosphorylation, sequentially or simultaneously. For instance a preliminary screen may identify molecules which modulate DNA binding by ATM and such substances may then be used in assays to determine their ability (or not) to modulate phosphorylation of p53. The converse, in which ability to modulate phosphorylation is determined prior to ability to modulate ATM DNA binding, is also possible, as is to run two assays in parallel.

Preliminary assays in vitro may be followed by, or run in parallel with, in vivo assays.

Of course, the person skilled in the art will design any appropriate control experiments with which to compare results obtained in test assays.

Performance of an assay method according to the present invention may be followed by isolation and/or manufacture and/or use of a compound, substance or molecule which tests positive for ability to modulate interaction between ATM and p53 and/or inhibit ATM or p53 activity or a mediated activity.

The precise format of an assay of the invention may be varied by those of skill in the art using routine skill and knowledge. For example, interaction between substances may be studied in vitro by labelling one with a detectable label and bringing it into contact with the other which has been immobilised on a solid support. Suitable detectable labels, especially for peptidyl substances include $^{35}$S-methionine which may be incorporated into recombinantly produced peptides and polypeptides. Recombinantly produced peptides and polypeptides may also be expressed as a fusion protein containing an epitope which can be labelled with an antibody.

The protein which is immobilized on a solid support may be immobilized using an antibody against that protein bound to a solid support or via other technologies which are known per se. A preferred in vitro interaction may utilise a fusion protein including glutathione-S-transferase (GST). This may be immobilized on glutathione agarose beads. In an in vitro assay format of the type described above a test compound can be assayed by determining its ability to diminish the amount of labelled peptide or polypeptide which binds to the immobilized GST-fusion polypeptide. This may be determined by fractionating the glutathione-agarose beads by SDS-polyacrylamide gel electrophoresis. Alternatively, the beads may be rinsed to remove unbound protein and the amount of protein which has bound can be determined by counting the amount of label present in, for example, a suitable scintillation counter.

An assay according to the present invention may also take the form of an in vivo assay. The in vivo assay may be performed in a cell line such as a yeast strain or mammalian cell line in which the relevant polypeptides or peptides are expressed from one or more vectors introduced into the cell.

The ability of a test compound to modulate interaction between ATM and p53 may be determined using a so-called two-hybrid assay.

For example, a polypeptide or peptide containing a fragment of ATM or p53 as the case may be, or a peptidyl analogue or variant thereof as disclosed, may be fused to a DNA binding domain such as that of the yeast transcription factor GAL4. (A particularly preferred fragment of ATM may include or be the kinase domain or a fragment of the kinase domain.) The GAL4 transcription factor includes two functional domains. These domains are the DNA binding domain (GAL4 DBD) and the GAL4 transcriptional activation domain (GAL4TAD). By fusing one polypeptide or peptide to one of those domains and another polypeptide or peptide to the respective counterpart, a functional GAL4 transcription factor is restored only when two polypeptides or peptides of interest interact. Thus, interaction of the polypeptides or peptides may be measured by the use of a reporter gene probably linked to a GAL4 DNA binding site which is capable of activating transcription of said reporter gene. This assay format is described by Fields and Song, 1989, Nature 340; 245–246. This type of assay format can be used in both mammalian cells and in yeast. Other combinations of DNA binding domain and transcriptional activation domain are available in the art and may be preferred, such as the LexA DNA binding domain and the VP60 transcriptional activation domain.

When looking for peptides or other substances which interfere with interaction between a ATM polypeptide or peptide and p53 polypeptide or peptide, the ATM or p53 polypeptide or peptide may be employed as a fusion with (e.g.) the LexA DNA binding domain, and the counterpart p53 or ATM polypeptide or peptide as a fusion with (e.g.) VP60, and involves a third expression cassette, which may be on a separate expression vector, from which a peptide or a library of peptides of diverse and/or random sequence may be expressed. A reduction in reporter gene expression (e.g. in the case of β-galactosidase a weakening of the blue colour) results from the presence of a peptide which disrupts the ATM/p53 interaction, which interaction is required for transcriptional activation of the β-galactosidase gene. Where a test substance is not peptidyl and may not be expressed from encoding nucleic acid within a said third expression cassette, a similar system may be employed with the test substance supplied exogenously.

When performing a two hybrid assay to look for substances which interfere with the interaction between two polypeptides or peptides it may be preferred to use mammalian cells instead of yeast cells. The same principles apply and appropriate methods are well known to those skilled in the art.

In preferred assays according to the present invention, the end-point of the assay, that is to say that which is determined in order to assess the effect of the test agent on the interaction of interest, is phosphorylation of p53 or a fragment, variant or derivative thereof, or other molecule including a phosphorylation site homologous to one of those in p53 phosphorylated by ATM.

Thus, a further aspect of the present invention provides an assay method including (a) bringing into contact a substance which includes at least a fragment of ATM which phosphorylates p53, a substance which includes at least a fragment of p53 including a site phosphorylated by ATM, and a test compound; and, (b) determining phosphorylation at said site.

Of course, any suitable variant or derivative of ATM and/or p53 may be employed in such an assay.

Phosphorylation may be determined for example by immobilising p53 or a fragment, variant or derivative thereof, e.g. on a bead or plate, and detecting phosphorylation using an antibody or other binding molecule (such as Mdm2 or a fragment thereof) which binds the relevant site of phosphorylation with a different affinity when the site is phosphorylated from when the site is not phosphorylated. Such antibodies may be obtained by means of any standard technique as discussed elsewhere herein, e.g. using a phosphorylated peptide (such as a fragment of p53). Binding of a binding molecule which discriminates between the phosphorylated and non-phosphorylated form of p53 or relevant fragment, variant or derivative thereof may be assessed using any technique available to those skilled in the art, which may involve determination of the presence of a suitable label, such as fluorescence. Phosphorylation may be determined by immobilisation of p53 or a fragment, variant or derivative thereof, on a suitable substrate such as a bead or plate, wherein the substrate is impregnated with scintillant, such as in a standard scintillation proximetry assay, with phosphorylation being determined via measurement of the incorporation of radioactive phosphate. Phosphate incorporation into p53 or a fragment, variant or derivative thereof, may be determined by precipitation with acid, such as trichloroacetic acid, and collection of the precipitate on a nitrocellulose filter paper, followed by measurement of incorporation of radiolabeled phosphate.

An agent able to inhibit phosphorylation of p53 by ATM may include an ATP analogue or other substance able to affect the catalytic properties of the enzymically active site of ATM. An inhibitor of phosphorylation may interact with ATM within the kinase domain marked (for human ATM) in FIG. 6. Residues within this domain are involved with interaction with p53 and catalysis of the phosphorylation. Residues outside of the domain may also be involved in interacting with p53 and agents which interfere with such interaction may affect the phosphorylation as discussed elsewhere herein.

The amount of test substance or compound which may be added to an assay of the invention will normally be determined by trial and error depending upon the type of compound used. Typically, from about 0.001 nM to 1 mM or more concentrations of putative inhibitor compound may be used, for example from 0.01 nM to 100 μM, e.g. 0.1 to 50 μM, such as about 10 μM. Greater concentrations may be used when a peptide is the test substance. Even a molecule which has a weak effect may be a useful lead compound for further investigation and development. Compounds which may be used may be natural or synthetic chemical compounds used in drug screening programmes. Extracts of plants which contain several characterised or uncharacterised components may also be used.

Antibodies directed to the site of interaction in either protein form a further class of putative inhibitor compounds. Candidate inhibitor antibodies may be characterised and their binding regions determined to provide single chain antibodies and fragments thereof which are responsible for disrupting the interaction.

Antibodies may be obtained using techniques which are standard in the art. Methods of producing antibodies include immunising a mammal (e.g. mouse, rat, rabbit, horse, goat, sheep or monkey) with the protein or a fragment thereof. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

As an alternative or supplement to immunising a mammal with a peptide, an antibody specific for a protein may be obtained from a recombinantly produced library of expressed immunoglobulin variable domains, e.g. using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimicks that of an antibody enabling it to bind an antigen or epitope.

Example antibody fragments, capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

A hybridoma producing a monoclonal antibody according to the present invention may be subject to genetic mutation or other changes. It will further be understood by those skilled in the art that a monoclonal antibody can be subjected to the techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP184187A, GB 2188638A or EP-A-0239400. Cloning and expression of chimeric antibodies are described in EP-A-0120694 and EP-A-0125023.

Hybridomas capable of producing antibody with desired binding characteristics are within the scope of the present invention, as are host cells, eukaryotic or prokaryotic, containing nucleic acid encoding antibodies (including antibody fragments) and capable of their expression. The invention also provides methods of production of the antibodies including growing a cell capable of producing the antibody under conditions in which the antibody is produced, and preferably secreted.

The reactivities of antibodies on a sample may be determined by any appropriate means. Tagging with individual reporter molecules is one possibility. The reporter molecules may directly or indirectly generate detectable, and preferably measurable, signals. The linkage of reporter molecules may be directly or indirectly, covalently, e.g. via a peptide bond or non-covalently. Linkage via a peptide bond may be as a result of recombinant expression of a gene fusion encoding antibody and reporter molecule. The mode of determining binding is not a feature of the present invention and those skilled in the art are able to choose a suitable mode according to their preference and general knowledge.

Antibodies may also be used in purifying and/or isolating a polypeptide or peptide according to the present invention, for instance following production of the polypeptide or peptide by expression from encoding nucleic acid therefor. Antibodies may be useful in a therapeutic context (which may include prophylaxis) to disrupt the ATM/p53 (or ATR/p53) interaction with a view to inhibiting their activity. Antibodies can for instance be micro-injected into cells, e.g. at a tumour site, subject to radio- and/or chemo-therapy (as discussed already above). Antibodies may be employed in accordance with the present invention for other therapeutic and non-therapeutic purposes which are discussed elsewhere herein.

Other candidate inhibitor compounds may be based on modelling the 3-dimensional structure of a polypeptide or peptide fragment and using rational drug design to provide potential inhibitor compounds with particular molecular shape, size and charge characteristics.

A compound found to have the ability to affect ATM and/or p53 activity has therapeutic and other potential in a number of contexts, as discussed. For therapeutic treatment such a compound may be used in combination with any other active substance, e.g. for anti-tumour therapy another anti-tumour compound or therapy, such as radiotherapy or chemotherapy. In such a case, the assay of the invention, when conducted in vivo, need not measure the degree of modulation of interaction between p53 and ATM (or appropriate fragment, variant or derivative thereof) or of modulation of p53 phosphorylation or activity caused by the compound being tested. Instead the effect on DNA repair, homologous recombination, cell viability, cell killing (e.g. in the presence and absence of radio- and/or chemo-therapy), retroviral integration, and so on, may be measured. It may be that such a modified assay is run in parallel with or subsequent to the main assay of the invention in order to confirm that any such effect is as a result of the inhibition of interaction between ATM and p53 caused by said inhibitor compound and not merely a general toxic effect.

Thus, an agent identified using one or more primary screens (e.g. in a cell-free system) as having ability to interact with ATM and/or p53 and/or modulate activity of ATM and/or p53 may be assessed further using one or more secondary screens. A secondary screen may involve testing for cellular radiosensitisation and/or sensitisation to radiomimetic drugs, effect on chromosome telomere length, inducing or preventing cell-cycle arrest following irradiation or other cellular insult, an effect of p53 induction following ionising radiation or other cellular insult, or induction of p21 or other downstream p53 target.

Following identification of a substance or agent which modulates or affects ATM and/or p53 activity, the substance or agent may be investigated further. Furthermore, it may be manufactured and/or used in preparation, i.e. manufacture or formulation, of a composition such as a medicament, pharmaceutical composition or drug. These may be administered to individuals, e.g. for any of the purposes discussed elsewhere herein.

As noted, the agent may be peptidyl, e.g. a peptide which includes a sequence as recited above, or may be a functional analogue of such a peptide.

As used herein, the expression "functional analogue" relates to peptide variants or organic compounds having the same functional activity as the peptide in question, which may interfere with the interaction between ATM and p53. Examples of such analogues include chemical compounds which are modelled to resemble the three dimensional structure of the ATM or p53 domain in the contact area, and in particular the arrangement of the key amino acid residues as they appear in ATM or p53.

In a further aspect, the present invention provides the use of the above substances in methods of designing or screening for mimetics of the substances.

Accordingly, the present invention provides a method of designing mimetics of ATM or p53 having the biological activity of p53 or ATM binding or inhibition, the activity of allosteric inhibition of p53 or ATM and/or the activity of modulating, e.g. inhibiting, ATM/p53 interaction, said method comprising:

(i) analysing a substance having the biological activity to determine the amino acid residues essential and important for the activity to define a pharmacophore; and, (ii) modelling the pharmacophore to design and/or screen candidate mimetics having the biological activity.

Suitable modelling techniques are known in the art. This includes the design of so-called "mimetics" which involves the study of the functional interactions fluorogenic oligonucleotide the molecules and the design of compounds which contain functional groups arranged in such a manner that they could reproduced those interactions.

The designing of mimetics to a known pharmaceutically active compound is a known approach to the development of pharmaceuticals based on a "lead" compound. This might be desirable where the active compound is difficult or expensive to synthesise or where it is unsuitable for a particular method of administration, e.g. peptides are not well suited as active agents for oral compositions as they tend to be quickly degraded by proteases in the alimentary canal. Mimetic design, synthesis and testing may be used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, e.g. by substituting each residue in turn. These parts or residues constituting the active region of the compound are known as its "pharmacophore".

Once the pharmacophore has been found, its structure is modelled to according its physical properties, e.g. stereochemistry, bonding, size and/or charge, using data from a range of sources, e.g. spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

The mimetic or mimetics found by this approach can then be screened to see whether they have the target property, or to what extent they exhibit it. Further optimisation or modification can then be carried out to arrive at one or more final mimetics for in vivo or clinical testing.

Mimetics of this type together with their use in therapy form a further aspect of the invention.

The present invention further provides the use of a peptide which includes a sequence as disclosed, or a derivative, active portion, analogue, variant or mimetic, thereof able to interact with ATM or p53 and/or modulate, e.g. inhibit, interaction between ATM and p53 and/or modulate, e.g inhibit, ATM and/or p53 activity, in screening for a substance able to interact with p53 and/or ATM, and/or modulate, e.g. inhibit, interaction between ATM and p53, and/or inhibit ATM and/or p53 activity.

Generally, such a substance, e.g. inhibitor, according to the present invention is provided in an isolated and/or purified form, i.e. substantially pure. This may include being in a composition where it represents at least about 90% active ingredient, more preferably at least about 95%, more preferably at least about 98%. Such a composition may, however, include inert carrier materials or other pharmaceutically and physiologicaly acceptable excipients. As noted below, a composition according to the present invention may include in addition to an inhibitor compound as disclosed, one or more other molecules of therapeutic use, such as an anti-tumour agent.

The present invention extends in various aspects not only to a substance identified as a modulator of ATM and p53 interaction and/or ATM or p53-mediated activity, property or pathway, in accordance with what is disclosed herein, but also a pharmaceutical composition, medicament, drug or other composition comprising such a substance, a method comprising administration of such a composition to a patient, e.g. for a purpose discussed elsewhere herein, which may include preventative treatment, use of such a substance in manufacture of a composition for administration, e.g. for a purpose discussed elsewhere herein, and a method of making a pharmaceutical composition comprising admixing such a substance with a pharmaceutically acceptable excipient, vehicle or carrier, and optionally other ingredients.

A substance according to the present invention such as an inhibitor of ATM and p53 interaction may be provided for use in a method of treatment of the human or animal body by therapy which affects an ATM or p53-mediated activity in cells, e.g. tumour cells. Other purposes of a method of treatment employing a substance in accordance with the present invention are dicussed elsewhere herein.

Thus, the invention further provides a method of modulating an ATM and/or p53-mediated activity, e.g. for a purpose discussed elsewhere herein, which includes administering an agent which modulates, inhibits or blocks the interaction of ATM with p53 protein, such a method being useful in treatment where such modulation, inhibition or blocking is desirable, or an agent which increase, potentiates or strengthens interaction of ATM with p53, useful in treatment where this is desirable.

The invention further provides a method of treatment which includes administering to a patient an agent which interferes with the interaction of ATM with p53. Exemplary purposes of such treatment are discussed elsewhere herein.

Whether it is a polypeptide, antibody, peptide, nucleic acid molecule, small molecule, mimetic or other pharmaceutically useful compound according to the present invention that is to be given to an individual, administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g. decisions on dosage etc, is within the responsibility of general practioners and other medical doctors.

A composition may be administered alone or in combination with other treatments, either simultaneously or sequentially dependent upon the condition to be treated.

Pharmaceutical compositions according to the present invention, and for use in accordance with the present invention, may include, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil.

Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer-'s Injection, Lactated Ringer's Injection. Preservatives, stabilisers, buffers, antioxidants and/or other additives may be included, as required.

Liposomes, particularly cationic liposomes, may be used in carrier formulations.

Examples of techniques and protocols mentioned above can be found in Remington's Pharmaceutical Sciences, 16th edition, Osol, A. (ed), 1980.

The agent may be administered in a localised manner to a tumour site or other desired site or may be delivered in a manner in which it targets tumour or other cells.

Targeting therapies may be used to deliver the active agent more specifically to certain types of cell, by the use of targeting systems such as antibody or cell specific ligands. Targeting may be desirable for a variety of reasons, for example if the agent is unacceptably toxic, or if it would otherwise require too high a dosage, or if it would not otherwise be able to enter the target cells.

Instead of administering these agents directly, they may be produced in the target cells by expression from an encoding gene introduced into the cells, eg in a viral vector (a variant of the VDEPT technique—see below). The vector may targeted to the specific cells to be treated, or it may contain regulatory elements which are switched on more or less selectively by the target cells.

The agent (e.g. small molecule, mimetic) may be administered in a precursor form, for conversion to the active form by an activating agent produced in, or targeted to, the cells to be treated. This type of approach is sometimes known as ADEPT or VDEPT, the former involving targeting the activator to the cells by conjugation to a cell-specific antibody, while the latter involves producing the activator, e.g. an enzyme, in a vector by expression from encoding DNA in a viral vector (see for example, EP-A-415731 and WO 90/07936).

An agent may be administered in a form which is inactive but which is converted to an active form in the body. For instance, the agent may be phosphorylated (e.g. to improve solubility) with the phosphate being cleaved to provide an active form of the agent in the body.

A composition may be administered alone or in combination with other treatments, either simultaneously or sequentially dependent upon the condition to be treated, such as cancer, virus infection or any other condition in which a ATM or p53-mediated effect is desirable.

Nucleic acid according to the present invention, encoding a polypeptide or peptide able to modulate, e.g. interfere with, ATM and p53 interaction and/or induce or modulate activity or other ATM or p53-mediated cellular pathway or function, may be used in methods of gene therapy, for instance in treatment of individuals, e.g. with the aim of preventing or curing (wholly or partially) a disorder or for another purpose as discussed elsewhere herein.

Vectors such as viral vectors have been used in the prior art to introduce nucleic acid into a wide variety of different target cells. Typically the vectors are exposed to the target cells so that transfection can take place in a sufficient proportion of the cells to provide a useful therapeutic or prophylactic effect from the expression of the desired polypeptide. The transfected nucleic acid may be permanently incorporated into the genome of each of the targeted cells, providing long lasting effect, or alternatively the treatment may have to be repeated periodically.

A variety of vectors, both viral vectors and plasmid vectors, are known in the art, see U.S. Pat. No. 5,252,479 and WO 93/07282. In particular, a number of viruses have been used as gene transfer vectors, including papovaviruses, such as SV40, vaccinia virus, herpesviruses, including HSV and EBV, and retroviruses. Many gene therapy protocols in the prior art have used disabled murine retroviruses.

As an alternative to the use of viral vectors other known methods of introducing nucleic acid into cells includes electroporation, calcium phosphate co-precipitation, mechanical techniques such as microinjection, transfer mediated by liposomes and direct DNA uptake and receptor-mediated DNA transfer.

Receptor-mediated gene transfer, in which the nucleic acid is linked to a protein ligand via polylysine, with the ligand being specific for a receptor present on the surface of the target cells, is an example of a technique for specifically targeting nucleic acid to particular cells.

A polypeptide, peptide or other substance able to modulate able to modulate or interfere with the interaction of the relevant polypeptide, peptide or other substance as disclosed herein, or a nucleic acid molecule encoding a peptidyl such molecule, may be provided in a kit, e.g. sealed in a suitable container which protects its contents from the external environment. Such a kit may include instructions for use.

In further aspects the present invention provides for the provision of purified ATM and purified ATR. Purified ATM or ATR, for instance about 10% pure, more preferably about 20% pure, more preferably about 30% pure, more preferably about 40% pure, more preferably about 50% pure, more preferably about 60% pure, more preferably about 70% pure, more preferably about 80% pure, more preferably about 90% pure, more preferably about 95% pure, or substantially pure ATM or ATR is obtainable using DNA. Such DNA may be in any form which ATM or ATR bind, including single-stranded DNA, double-stranded DNA, nicked DNA, covalently closed DNA circles and so on. It is surprising that any and all of these are bound by ATM as shown experimentally below.

In one aspect the present invention provides the use of DNA for purifying ATM or ATR.

In another aspect the present invention provides a method of purifying ATM or ATR, the method including contacting ATM or ATR with DNA. A mixture of material including ATM or ATR may be contacted against immobilised DNA (e.g. on a bead or agarose, and either covalently or non-covalently such as via a specific binding molecule such as streptavidin or biotin) and molecules which do not bind washed off.

We have also established that ATM and ATR may be purified using NTA, preferably in the presence of $Ni^{2+}$. The NTA may be on any suitable support such as agarose or sepharose. Thus, a further aspect of the present invention provides the use of NTA, preferably with $Ni^{2+}$, for purifying ATM or ATR.

Another aspect of the present invention provides a method of purifying ATM or ATR which includes, contacting ATM or ATR with NTA, preferably with $Ni^{2+}$ and washing off molecules which do not bind.

Purification using DNA may be combined with purification using NTA, preferably with $Ni^{2+}$, sequentially or simultaneously.

Either technique may be used for identification of co-factors of ATM which modulate ATM activity, such as factors which affect the interaction between ATM and DNA.

The ATM contacted by DNA and/or NTA in a purification may be in a mixture of molecules, such as a cellular extract, such as from a cell of an A-T patient, a normal cell of an organism such as a human or a recombinant host cell expressing the protein from encoding DNA, such as a bacterial, eukaryotic (e.g. mammalian or yeast) or insect cell, such as in a baculovirus expression system. Purification may follow production of ATM recombinantly in a suitable expression system, such as a cell, by expression from encoding nucleic acid.

Following purification, ATM may be used as desired, e.g. in an assay for an agent which modulates its phosphorylation of p53 or other molecule, in raising or obtaining a specific antibody or other binding molecule, or in a therapeutic context such as to compensate in an individual for the absence of wild-type ATM (as in, for example, a patient with A-T).

Various further aspects and embodiments of the present invention will be apparent to those skilled in the art in view of the present disclosure. Certain aspects and embodiments of the invention will now be illustrated by way of example and with reference to the figures discussed already above.

ATM Binds to DNA

A biotinylated random ds 50-mer oligonucleotide was coupled to streptavidin iron-oxide particles and these were employed to recover DNA binding proteins from HeLa cell nuclear extracts. This approach revealed that ATM interacts with particles bearing this random piece of ds DNA (FIG. 1A). This binding is due to the presence of DNA, since streptavidin iron-oxide particles alone are unable to bind ATM (FIG. 1A). Importantly, the sequence specific DNA-binding protein Sp1 and the non-specific DNA interacting protein complex containing RNA polymerase II (Pol II) are both unable to interact stably with the random DNA fragment employed in these studies (FIG. 1A). Furthermore, DNA-$PK_{CS}$ present in the crude nuclear extract binds only very inefficiently to the immobilised DNA despite the fact that its DNA-targeting component Ku is present (data not shown). Notably, protein quantification reveals that, under conditions in which over 90% of ATM binds to the DNA-coupled particles, less than 2% of total nuclear protein is retained. Hence, the retention of ATM by DNA in these studies is highly specific.

The above assay revealed that ATM, or an ATM complex, is capable of binding to a random piece of duplex DNA. Additional studies revealed that ATM is also retained by particles containing another unrelated oligonucleotide, suggesting strongly that the interaction is not sequence-specific (data not shown). To investigate the DNA binding properties of ATM further, we tested a series of DNAs with a variety of sizes and architectures. In these studies, binding and initial washes were conducted in the presence of 50 mM KCl, then bound material was eluted by sequential washes at 100, 250 and 500 nM KCl. FIG. 1B demonstrates that the interaction between DNA and ATM is dependent on the size of the DNA-duplex. Thus, with a ds 15-mer, some ATM is still present in the unbound fraction and most bound material elutes in the lower salt wash. However, as the duplex size is increased, it becomes progressively more effective at binding ATM, such that when ds oligonucleotides of 50 bp or larger are employed, binding of ATM is almost quantitative and all bound ATM elutes in the higher salt wash (FIG. 1B).

Since a variety of DNA structures are known to be produced by IR and are present during DNA-repair processes, we assessed the ability of ATM to bind to various types of DNA structure. Thus, assays were conducted employing particles coupled to a ds 100-mer oligonucleotide bearing a nick, a single-strand to double-strand transition, a gap of 35 bp, or a 10 base insertion loop. Notably, under the assay conditions employed, ATM binds to these DNA molecules with equal efficiency and apparent affinity as it does to the fully ds DNA oligonucleotide (FIG. 1C). Additional studies show that ATM also binds effectively to ss DNA (FIG. 1C) and that, as with ds-DNA, this binding is dependent on oligonucleotide length (data not shown). Furthermore, ATM binding in such experiments is competed effectively by linear and circular plasmid DNA, suggesting that DNA termini are not required for ATM binding (NDL, unpublished data). Taken together, these data show that ATM, or a complex containing this factor, is capable of interacting with DNA molecules containing a variety of different structures in an apparently non-sequence specific fashion. Our results also show that ATM prefers to bind to linear DNA, preferentially binding to the ends of the DNA.

Purification of ATM

To increase our understanding of ATM further, we decided to attempt to purify this protein to essential homogeneity and thus separate it from other DNA-binding proteins, DNA repair factors, and protein and lipid kinases. The purification strategy we developed is outlined in FIG. 2A. Since ATM is expressed ubiquitously and is located primarily in the cell nucleus, HeLa cell nuclear extract was used as starting material. Because no biochemical assay was available for ATM protein function, we monitored its purification by Western blot analysis using antibodies raised against two different portions of the protein (Lakin et al., 1996). This approach not only revealed the fractionation of ATM but also allowed us to pool fractions that were devoid of the abundant DNA-PK enzyme through simultaneously testing for the presence of DNA-$PK_{CS}$ and Ku. In light of the DNA-binding properties of ATM, we employed a final DNA affinity step in the purification scheme (FIG. 2B, lane 4). Silver staining demonstrates that this leads to an essentially homogenous preparation of a ~350 kDa polypeptide, and Western blotting studies reveal that this is recognised strongly by ATM antiserum ATM.B (FIG. 2B). Since this protein is also recognised by two other antibodies raised to distinct regions of the ATM polypeptide (data not shown), we conclude that the purified protein is indeed ATM. As revealed in FIG. 2B, whilst ATM is enriched throughout the purification procedure, Ku, DNA-$PK_{CS}$, and the abundant ss DNA binding protein Replication Protein A (RPA) are all efficiently removed. Quantitative Western blotting and silver-staining reveal that the final yield of ATM is approximately 25% and indicate that ATM is of relatively low abundance, comprising around 0.002% of total nuclear protein by weight.

Purified ATM Possesses an Associated p53 Kinase Activity

Notably, as for DNA-PK (Hartley et al., 1995), purified ATM preparations were found to be devoid of detectable kinase activity towards PI and a variety of phosphorylated PI derivatives. Although we cannot exclude that ATM phosphorylates these or related phospholipids under certain conditions or in the presence of additional components, we conclude that ATM is not a lipid kinase. To assay for possible ATM-associated protein kinase activity, we performed in vitro kinase assays using equivalent amounts of various recombinant or purified proteins that we speculated may be ATM substrates. Certain candidate substrates, such as DNA-$PK_{CS}$, Ku, proliferating cellular nuclear antigen (PCNA), and the 34 kDa subunit of RPA (RPA-p34), were chosen by virtue of their association with DNA damage detection and/or involvement in DNA repair. We also tested Sp1 and p53, since these are both good substrates for DNA-PK and because A-T cells display aberrant induction of p53 in response to IR. A final protein tested was $I_kB$, since recent data have implicated this is an ATM target (Jung et al., 1995; Jung et al., 1997). Given that we had found that ATM binds to DNA, we included a DNA oligonucleotide known to activate DNA-PK in all initial kinase reactions.

Figure 3:
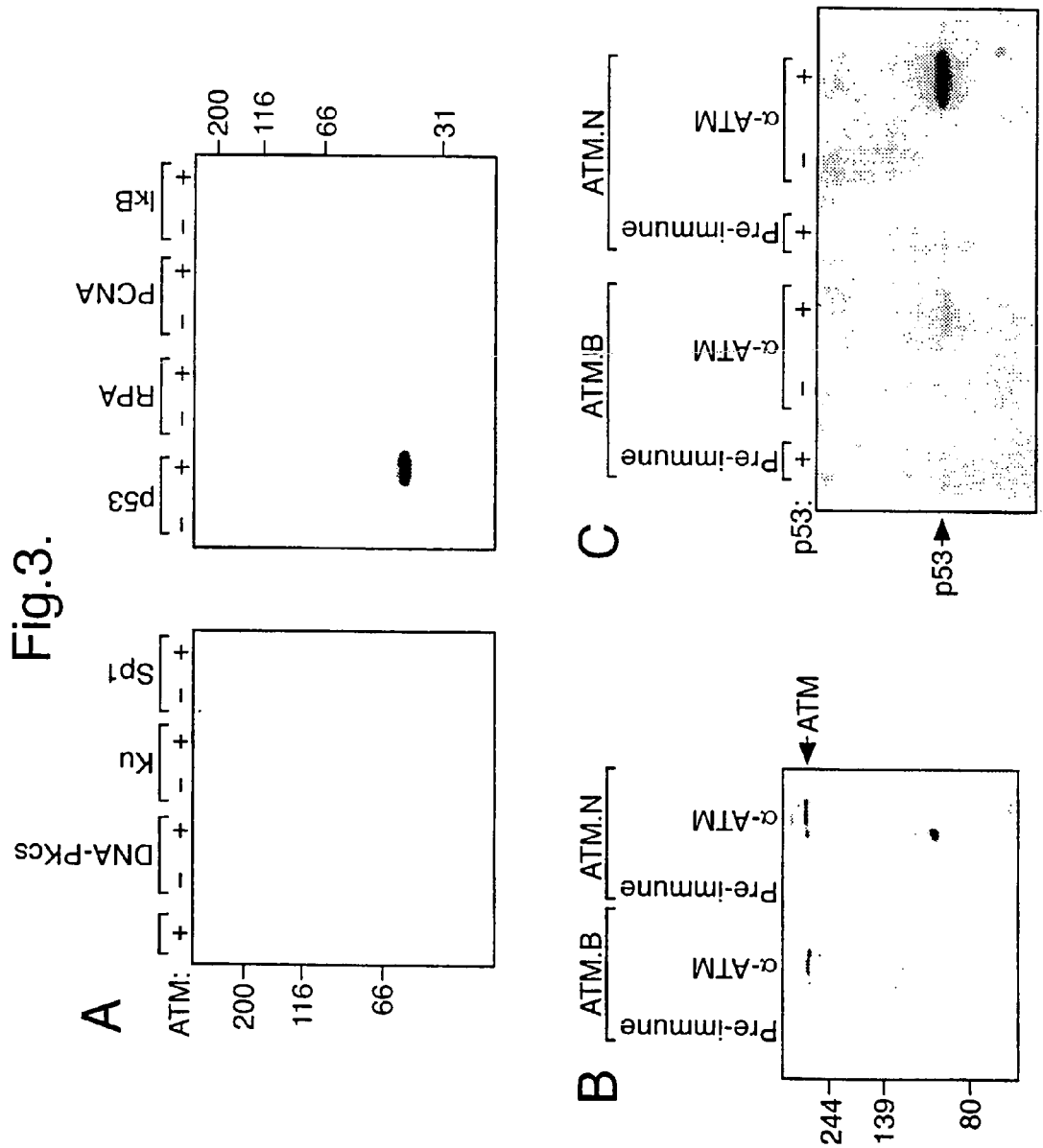
FIG. 3: Purified ATM possesses an associated p53 kinase activity. (A) Analysis of putative ATM substrates. DNA-PK$_{CS}$ (60 ng), Ku (100 ng), Sp1 (100 ng), p53 (100 ng), RPA-p34 (100 ng) or PCNA (100 ng) were used in kinase reactions in conjunction with approximately 11 fmole of purified ATM (see Experimental Procedures). Proteins were resolved on either 7% (left panel) or 10% (right panel) polyacrylamide gels and phosphorylated proteins detected by autoradiography. (B) Analysis of total proteins immunoprecipitated from purified ATM preparations. Purified ATM was biotinylated and subjected to immunoprecipitation using either pre-immune sera, or ATM antisera raised against amino acid residues 1980–2337 (ATM.B) or the N-terminus (ATM.N) of ATM. Precipitated proteins were resolved on 7.8% polyacrylamide gels and, after transfer to nitrocellulose, total precipitated proteins were detected by probing filters with streptavidin-conjugated horseradish peroxidase. (C) Immunoprecipitated ATM possesses p53 kinase activity. Purified-ATM was immunoprecipitated using preimmune sera, or anti-ATM antisera ATM.B or ATM.N. Following immunoprecipitation, kinase reactions were performed either in the presence or absence of p53 as indicated. Phosphorylated proteins were resolved on 10% polyacrylamide gels and detected by autoradiography.

Notably, none of DNA-$PK_{CS}$, RPA-p45 and PCNA was phosphorylated efficiently by purified ATM (FIG. 3A). However, longer exposures of autoradiograms reveals weak phosphorylation of both the 70 kDa subunit of Ku (Ku70) and Sp1 by ATM preparations (data not shown). Furthermore, prolonged exposures also reveal that ATM is capable of autophosphorylation (data not shown), consistent with previous rough studies employing ATM that had been immunoprecipitated directly from crude cell extracts (Keegan et al., 1996) (likely to contain all sorts of impurities). Most significantly, however, several independently purified ATM preparations were consistently found to phosphorylate p53 with high efficiency (FIG. 3A) (contrary to the mentioned results of Keegan et al.). Taken together, these data reveal that, under our assay conditions, a protein kinase activity co-purifies with ATM that phosphorylates p53 efficiently, and Sp1 and Ku70 weakly. Importantly, DNA-PK efficiently phosphorylates p53, Sp1, Ku70 and RPA-p34 in vitro, revealing that the ATM-associated kinase activity exhibits a different substrate specificity from that of DNA-PK. This, together with the absence of detectable DNA-PKcs or Ku in our ATM preparations argues strongly against the possibility that the ATM-associated protein kinase activity is imparted by DNA-PK contamination.

Although the above results reveal that a p53 kinase activity co-purifies with ATM, prolonged silver staining reveals additional polypeptides in our ATM preparations (data now shown). The possibility therefore existed that the p53 kinase activity that we had detected was not mediated by ATM but by a contaminating protein. To address this issue, we immunoprecipitated ATM from purified ATM preparations using polyclonal antibodies raised against either the N-terminal region (ATM.N) or an internal region (ATM.B) of the ATM polypeptide (Lakin et al., 1996). After washing the immunoprecipitated material extensively in the presence of 500 mM KCl and 0.1% Nonidet-P40, it was employed in kinase reactions using p53 as substrate. To establish the purity of the immunoprecipitated material, purified ATM was biotinylated and immunoprecipitated in parallel with ATM employed in the kinase reactions. The biotinylated precipitated proteins were then visualised by Western transfer and probing with streptavidin conjugated horseradish peroxidase.

As illustrated in FIG. 3B, a biotinylated protein of approximately 350 kDa in size, the predicted molecular mass of ATM, is precipitated in these studies by anti-ATM antisera but not by pre-immune sera. Notably, no other proteins are consistently precipitated by both ATM antisera in these assays (a polypeptide of –100 kDa is apparent in the ATM.N precipitation in FIG. 3B but is not present in ATM.B immunoprecipitates and was not consistently observed in subsequent experiments using ATM.N).

Most importantly, these experiments revealed that p53 kinase activity is immunoprecipitated by the two ATM antisera. Greater ATM associated kinase activity is observed with ATM.N than with ATM.B, despite only slightly higher amounts of ATM being precipitated by ATM.N (FIG. 3C). One possible explanation for this is that ATM.B, which recognises epitopes close to the ATM kinase domain, impairs ATM protein kinase activity. These studies show that the p53 kinase activity present in our ATM preparations follows ATM through a further highly stringent immunoaffinity purification step, and suggest strongly that ATM directly mediates p53 phosphoylation. Although unlikely in our opinion, it remains a possibility that p53 is phosphorylated by a distinct polypeptide that has escaped our detection methods and which remains associated with ATM throughout the stringent purification and immunoprecipitation protocols employed.

ATM Associated Kinase Activity is Stimulated by DNA

Figure 4:
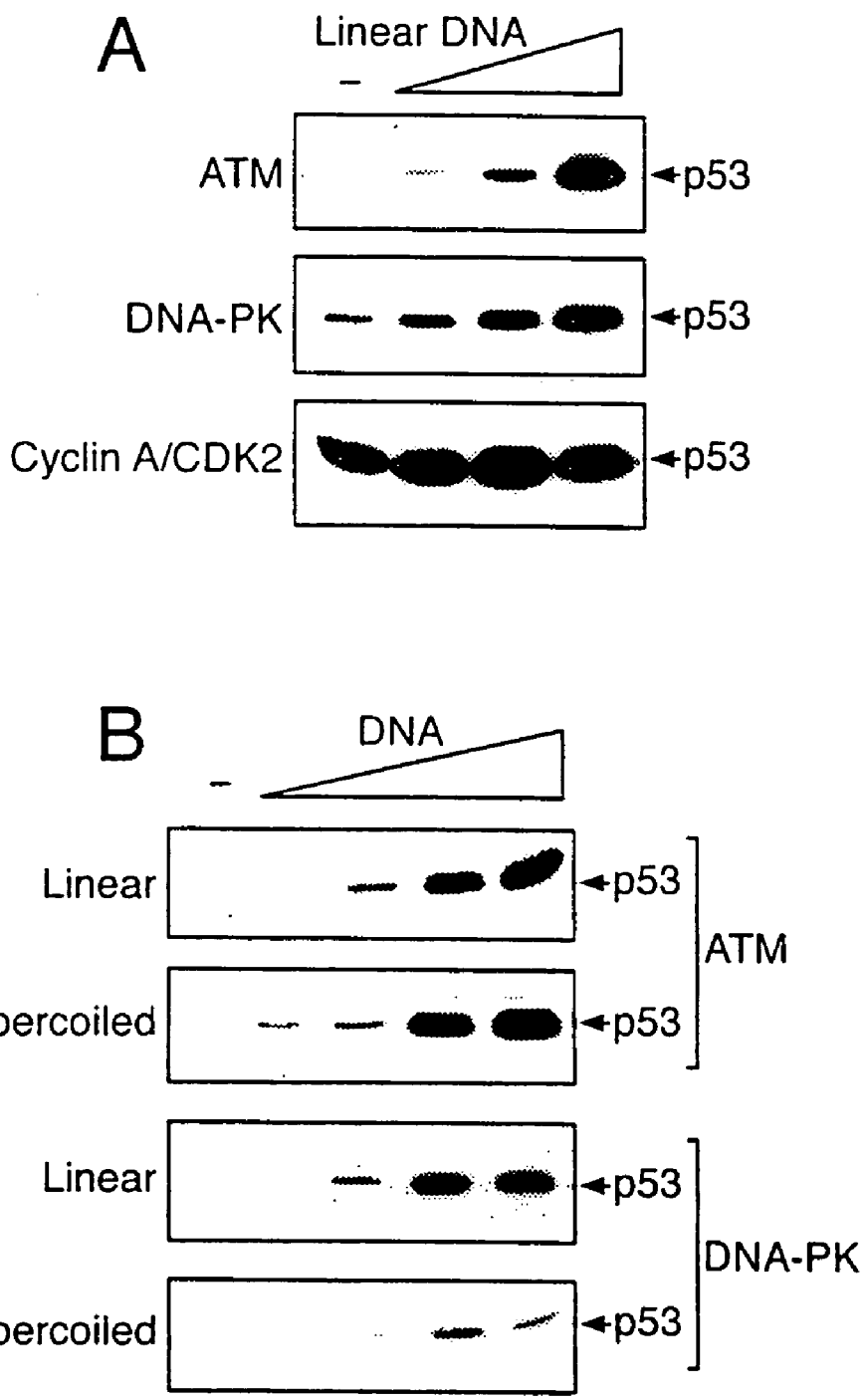
FIG. 4: A DNA-stimulated protein kinase activity co-purifies with ATM. (A) ATM associated kinase activity is stimulated by linear DNA containing multiple p53 binding sites. Purified ATM, DNA-PK or cyclin A/cdk2 (11 fmole), as indicated, were used in kinase reactions containing p53 either in the absence (−) or presence of 0.03, 0.3 or 3 fmole of linear DNA bearing multiple p53 binding sites (pG$_{13}$CAT). Proteins were resolved on 10% polyacrylamide gels and phosphorylated proteins visualised by autoradiography. (B) ATM associated kinase activity does not require DNA ends. In vitro kinase reactions containing 11 fmole of purified ATM in conjunction with p53 were performed in either the absence (−) or presence of 0.03, 0.3 or 30 fmole of linear or supercoiled pG$_{13}$CAT DNA. Proteins were detected as in (A).

Given that ATM can interact with DNA, we investigated whether ATM associated protein kinase activity is stimulated by a nucleic acid cofactor. To achieve this, we performed in vitro kinase assays using purified ATM either in the absence or presence of increasing amounts of DNA. Because previous studies have revealed that co-localisation of DNA-PK and Sp1 to the same DNA molecule increases phosphorylation efficiency (Lees-Miller et al., 1992; Gottlieb and Jackson, 1993), we employed a linear plasmid molecule bearing multiple p53 binding sites. These studies revealed that DNA addition leads to marked stimulation of p53 phosphorylation by DNA-PK (FIG. 4A, middle). Strikingly DNA addition was also found to result in marked stimulation of p53 phosphorylation in reactions containing ATM (FIG. 4A, top). Thus, purified ATM preparations contain a DNA-stimulatable p53 kinase activity. Longer exposures of autoradiograms reveal that the ATM polypeptide is also subject to phosphorylation in such assays and that this phosphorylation is stimulated by DNA (data not shown). Experiments employing equimolar amounts of DNA-PK and ATM revealed that the stimulation of p53 kinase activity by DNA is similar for ATM and DNA-PK, and that the stoichiometry of p53 phosphorylation by ATM is at least as high as that catalysed by DNA-PK (data not shown). Although DNA-dependent kinase activity was consistently observed in ATM preparations, the degree of activation was variable. In this regard, additional polypeptides were apparent in several preparations that displayed high levels of DNA activatability. Thus, it is possible that co-purifying polypeptides may be involved in high level ATM DNA dependent kinase activity. Notably, DNA-PK and ATM preparations both displayed significant but low levels of p53 kinase activity in the absence of DNA. It is not currently known, however, whether this reflects bona fide DNA-independent phosphorylation or results from small amounts of DNA in the protein preparations. Parallel experiments using cyclin A/cdk2 demonstrate no increase of p53 phosphorylation upon DNA addition (FIG. 4A), and a variety of other protein kinases that we have tested are not stimulated by DNA. These results therefore show that increased protein phosphorylation is not a general effect of adding DNA to p53 kinase assays and reveal that ATM is highly unusual in its ability to be stimulated by DNA.

We had established that ATM binds to various types of linear DNA molecule (see FIG. 1). Our binding competition studies indicated that ATM also interacts with supercoiled and nicked DNA (data not shown). We tested whether ATM associated kinase activity is affected differentially by various DNA structures. p53 kinase assays were performed in the absence of DNA or in the presence of increasing amounts of either supercoiled or restriction enzyme-linearised plasmid DNA.

Notably, ATM is activated by supercoiled and linear DNA (FIG. 4B), and additional studies revealed that good activation also occurs with nicked plasmid DNA molecules (data not shown). By contrast, DNA-PK is stimulated strongly by linear but only weakly by supercoiled plasmid DNA (FIG. 4B; based on previous studies, the weak activation by the latter probably reflects small amounts of nicked and/or linear DNA in the supercoiled plasmid preparation). These results are therefore consistent with data showing that ATM is able to interact with many different types of DNA structure. Furthermore, they show that, although ATM is analogous to DNA-PK in that its associated kinase activity is stimulated by DNA, the DNA cofactor requirements of the two enzymes are different.

ATM Associated Kinase Activity Phosphorylates p53 at Two Sites

To determine the site(s) of p53 that are phosphorylated by ATM, bacterially expressed p53 was radioactively phosphorylated by ATM in either the presence or absence of DNA. Labelled p53 was purified by electrophoresis, digested by trypsin, and the resulting products separated by reverse-phase HPLC. Analysis of the resulting radioactive profiles showed a major peak eluting at 11–12% acetonitrile. A novel set of radioactive p53 derived HPLC polypeptide peaks, which elute at 28–29% acetonitrile were induced substantially in the presence of DNA. Phosphoamino acid analysis revealed that the DNA induced peaks contained peptides labelled at both serine and threonine residues, suggesting either two distinctly labelled co-eluting peptides, or a single peptide containing both phosphoserine and phosphothreonine residues (data not shown). Radioactive peaks with similar elution properties were identified following phosphorylation of p53 by DNA-PK (FIG. 5B) or casein kinase I (data not shown). Previous studies have revealed that both DNA-PK and casein kinase I phosphorylate the N-terminal region of p53 (Lees-Miller et al., 1992; Milne et al., 1992). Initial attempts to sequence p53-derived peaks were unsuccessful, presumably because they possess blocked amino-termini. However, cleavage with endoproteinase Asp-N allowed sequencing of each. Notably, release of counts at cycles 9 and 12 of Edman degradation of peptide 2a reveals that the sites of phosphorylation correspond to p53 residues Ser-15 and Thr-18. Ser-15 has previously been demonstrated to be a phosphorylation site for DNA-PK (Lees-Miller et al., 1992). However, no detectable DNA-PK exists in our ATM preparations (see above).

We therefore conclude that a novel DNA dependent kinase activity is associated with ATM that targets Ser-15 and Thr-18 of p53.

DNA-PK ATR has an Associated Kinase Activity that Phosphorylates p53 at Ser15 and Thr18

Figure 5:
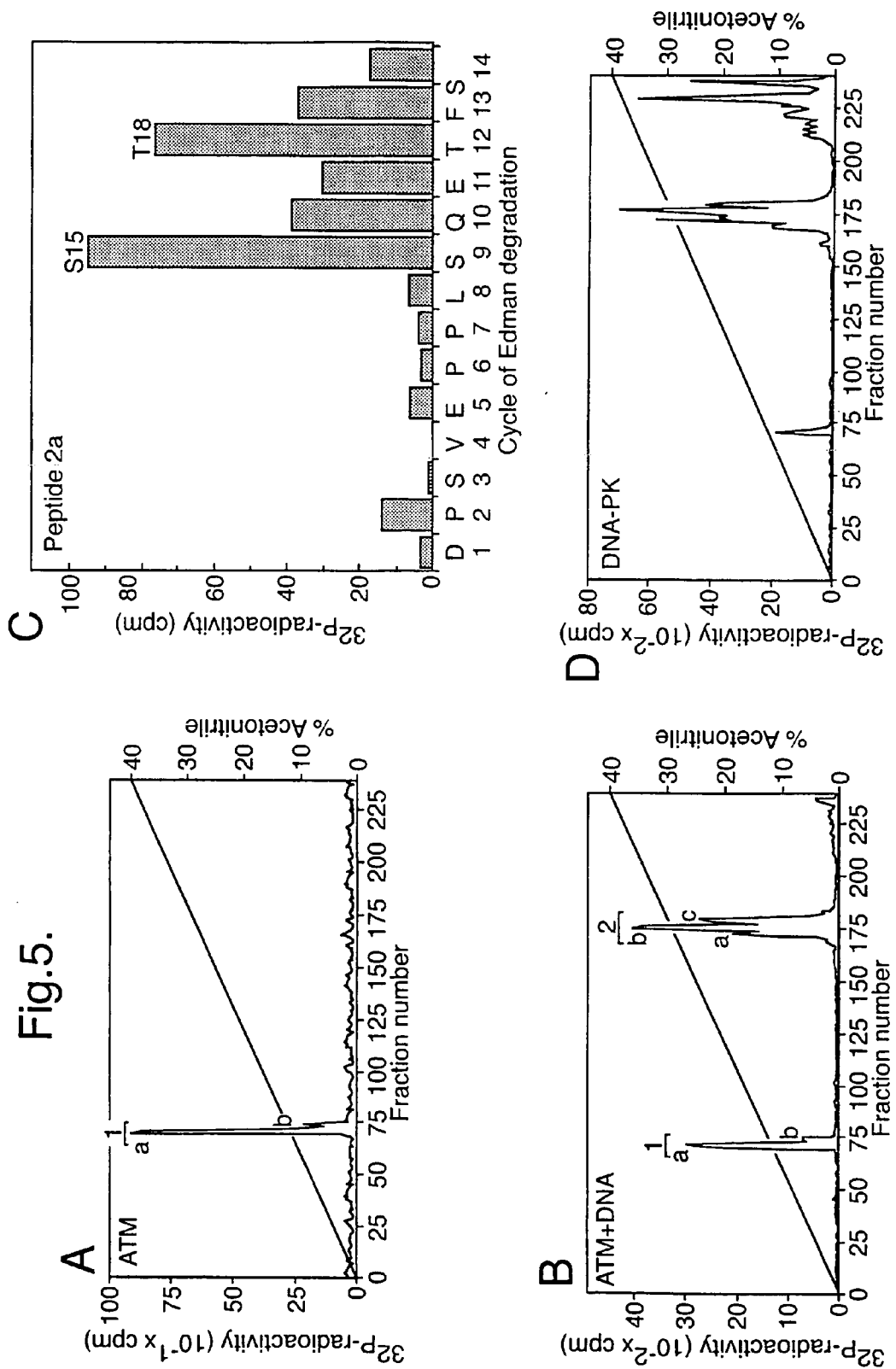
FIG. 5: ATM phosphorylated p53 at Ser15 and Thr18 in the presence of DNA. Kinase reactions employing ATM and p53 were performed in the presence and absence of DNA. These studies revealed phosphorylation of p53 was increased in the presence of DNA. (A/B) Bands corresponding to $^{32}$P-labelled p53 were excised from a gel, digested with trypsin, and chromatographed on a Vydac 218TP54 C18 column (see experimental procedures). Purified p53 fractions phosphorylated by ATM preparations in the presence, but not in the absence, of DNA (peptides 2a, 2b and 2c) were subjected to peptide sequence analysis as described in Experimental Procedures; radioactivity was measured after each cycle of Edman degradation. The putative amino acid sequence of the p53 peptide showing incorporation of $^{32}$P is indicated in panel C (SEQ ID NO:26). (D) Tryptic peptide map of p53 phosphorylated by DNA-PK in the presence of DNA. Kinase reactions containing DNA-PK and p53 were performed in the presence of linear DNA and $^{32}$P-labelled p53 was analysed as in (A,B), again revealing phosphorylation at Ser15 and Thr18.

Given the fact than an activity in our ATM preparations was found to phosphorylate residue Thr18 of p53, we decided to test whether DNA-PK is also able to phosphorylate this site. To this end, p53 was incubated in the presence of radiolabelled [$\beta^{32}$P] ATP with purified human DNA-PK (a preparation consisting of the Ku and DNA-PKcs components of the enzyme; prepared as described in Hartley et al., 1995) in either the absence or presence of a linearised plasmid DNA molecule, then, as described for analysis of ATM-mediated phosphorylation events, the p53 was treated with protease to generate phospho-peptides and these were analysed by reverse-phase HPLC. These studies revealed that, as in the ATM studies, a set of related peptides eluting at around 28–29% acetonitrile (co-fractionating with ATM-derived peptides, 2a, b, and c; compare FIGS. 5B and D) were phosphorylated by a DNA-PK associated kinase activity in a DNA-inducible fashion. Furthermore, analysis of these revealed that they correspond to p53 peptides containing phosphorylation on residues Ser15 and Thr19 (FIG. 5B). Subsequent studies using antibodies that recognise specifically p53 that is phosphorylated on Ser15 or Thr19 (see below for details of antibody preparation) confirmed that the DNA-PK-associated kinase activity phosphorylates both of these residues of p53. Therefore, contrary to expectations, DNA-PK-associated kinase activity phosphorylates p53 on Thr18 as well as Ser15.

ATR has an Associated Kinase Activity that Phosphorylates p53 at Ser15

Given that both DNA-PK-associated and a ATM-associated kinase activities phosphorylate p53 on Ser15 and Thr18, we decided to see whether other kinases exist that can target these residues. To facilitate this approach, we generated rabbit polyclonal antibodies that specifically recognise p53 that is phosphorylated on Thr18 (they do not recognise unphosphorylated p53 nor p53 that is phosphorylated solely on Ser15 nor is phosphorylated elsewhere). Similarly, we generated rabbit polyclonal antibodies that specifically recognised p53 phosphorylated on Ser15. These antibodies were generated by immunising rabbits with specific p53-based phospho-peptides (containing either Thr18 or Ser15 phosphorylated), then preparing the antibodies with the desired recognition characteristics (those that recognised the specific phosphorylated peptides but not unphosphorylated versions of these peptides) by chromatography on columns bearing immobilised unphosphorylated peptide and columns bearing specific phosphorylated peptides.

Figure 10:
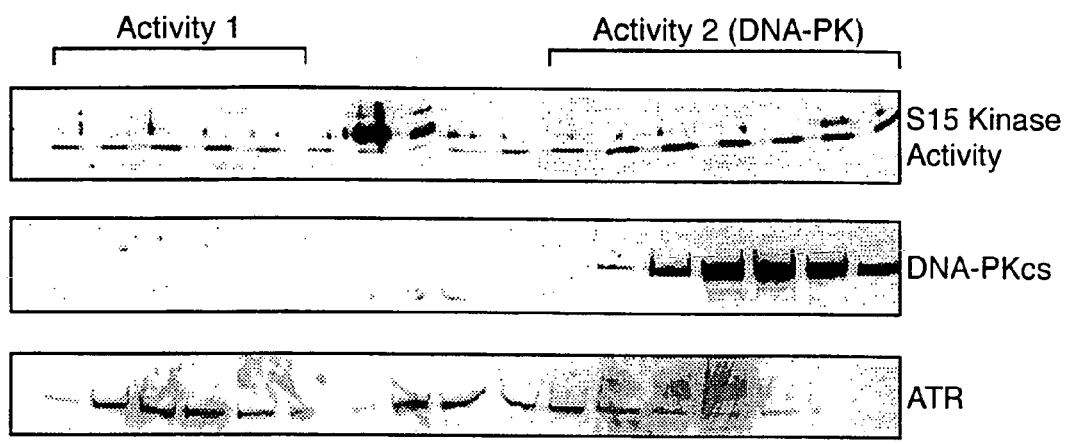
FIG. 10 shows fractionation of two DNA activated kinase activities in HeLa nuclear cell extract capable of phosphorylating Ser15 of p53. Top panel; a Western immuno-blot was performed with antibodies that specifically recognise p53 phosphorylated on Ser15 on reactions in which fractions generated when HeLa cell nuclear extract was fractionated on Q-sepharose were incubated with p53 and ATP in the presence of sonicated calf thymus DNA. Middle panel; the same set of fractions were tested for DNA-PKcs by using an anti-DNA-PKcs antiserum in western immuno-blot analysis. Lower panel: the same set of fractions were tested for the presence of ATR by using an anti-ATR antiserum in western immuno-blot analysis. Additional studies revealed that both activities detected are stimulated by DNA.
Figure 11:
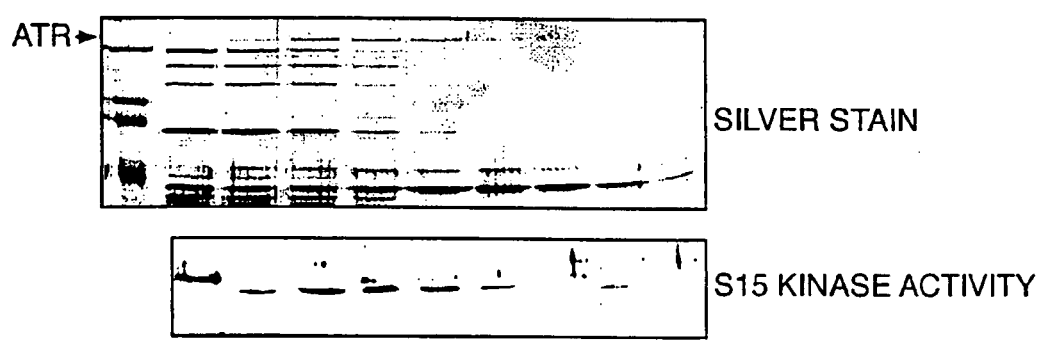
FIG. 11 shows DNA activated kinase activity (activity 1) co-fractionates with ATR. Activity peak 1 was fractionated further on DNA-cellulose followed by chromatography on Heparin-agarose. Bottom panel; the final set of fractions was tested for p53 kinase activity via incubation with p53, ATP and DNA and then analysis by SDS-polyacrylamide gel electrophoresis and Western immuno-blotting using the p53 Ser15-specific antibodies. Top panel; a silver-stain of an SDS-polyacrylamide gel of the same set of fractions tested for p53 kinase activity. ATR is indicated with an arrow.

To assess kinases activated in human cell extracts capable of phosphorylating p53 on Ser15, HeLa nuclear extract was fractionated chromatographically (see below) then the resulting fractions were incubated with full-length p53 protein and non-radioactively labelled ATP, either in the absence or presence of DNA. Phosphorylation of p53 was then assessed by subjecting the samples to SDS-polyacrylamide gel electrophoresis and Western immunoblotting. As shown in FIG. 10, two main peaks of kinase activity (termed "activity 1" and "activity 2") capable to targeting Ser15 (S15) were detected in fractions of HeLa nuclear extract that had been chromatographed on Q-sepharose. Further analysis of these fractions revealed that both activities were stimulated by DNA. Furthermore, Western blotting revealed that fractions comprising "activity 1" contained the ATM-related protein ATR, whereas those comprising "activity 2" contained DNA-PKcs (FIG. 10). In addition, other experiments revealed a third weaker, activity peak in fractions between those comprising activity 1 and activity 2, which corresponded to ATM. Further purification of activity peak 2 revealed that it corresponded to DNA-PK. Further fractionation of activity 1 revealed that, under all chromatographic separation techniques utilised, the DNA-activated p53 Ser15 kinase activity co-eluted with ATR. Indeed, through following this kinase activity, ATR could be purified to near homogeneity (e.g. FIG. 11; ATR was the only polypeptide whose elution was found to consistently parallel that of the kinase activity). Thus, in addition to DNA-PK and ATM targeting p53 Ser15, we have made the surprising discovery that this residue is also phosphorylated by a kinase activity associated with ATR.

Effect of p53 Phosphorylation on Interaction with Mdm2

To test whether phosphorylation on Ser15 or Thr18 of p53 affects its interaction with Mdm-2, phosphorylated and unphosphorylated p53-derived peptides were generated and were assessed for Mdm-2 binding by ELISA analysis. The four peptides used contained p53 residues 11 to 25 (in the sequence (SEQ ID NO:11) NH2-SGSGEPPLSOETFSDL-WKL-COOH; where the underlined sequence is that derived from p53) that were unphosphorylated (1); phosphorylated on residue equivalent to p53 residue Ser15(2); phosphorylated on residue equivalent to p53 residue Thr18(3); or phosphorylated on two residues, equivalent to p53 residue Ser15 and Thr18(4). Binding of Mdm-2 derivatives occurred effectively with unphosphorylated peptide 1 but was found to be inhibited dramatically in the cases of peptides 3 and 4, which contained phosphorylated Thr18. In contrast, binding was only impaired slightly by phosphorylation on Ser15 (peptide 2). We therefore conclude that phosphorylation on Thr18 of p53 has a dramatic effect on its interaction with Mdm-1 and that phosphorylation of this site is likely to play a key role in regulating p53 responses in vivo.

Additional Purification Method for ATM

HeLa nuclear extract was applied to $Ni^{2+}$—NTA agarose (Qiagen). We found that ATM binds very tightly to this matrix, but not very well to $Ni^{2+}$—IDA matrices.

5 ml of nuclear extract was loaded onto a 1×2.5 cm column of $Ni^{2+}$—NTA agarose in the following buffer (Buffer D; 25 mM HEPES-KOH, pH 7.6, 100 mM KCl, 10% Glycerol, 1 mM $MgCl_2$, 20 mM imidazole). The column was washed extensively (10 column volumes) before applying a linear gradient of 20 mM–500 mM imidazole in buffer D. Virtually pure ATM (as judged by silver stain analysis of 8% polyacrylamide gels) eluted near the end of the imidazole gradient. Less pure fractions of ATM eluted at the start of the gradient.

This provides a purification strategy for ATM or ATR that may be used alone, or in combination with various other chromatographic steps, e.g. DNA affinity chromatography as discussed already above.

DISCUSSION

We have demonstrated that ATM is retained on immobilised particles bearing DNA molecules. Notably, ATM binds to both ds and ss DNA in vitro, and studies employing a variety of unrelated oligonucleotides provide indication that this interaction is not sequence dependent. By exploiting these and other biochemical properties of ATM, we have developed a strategy to purify this polypeptide from HeLa nuclear extracts to near homogeneity. The high purity of our final ATM preparations and the fact that ATM in such preparations can re-bind to DNA provides indication that ATM interacts with DNA directly. Although this appears somewhat different from the situation with DNA-PKcs, which requires Ku to associate stably with DNA under our assay conditions, UV protein-DNA cross-linking has revealed that, in the context of the DNA-PKcs/Ku holoenzyme, DNA-PKcs does make close contacts with DNA (Gottlieb and Jackson, 1993). DNA-PKcs and ATM may interact with DNA through similar mechanisms.

Because the C-terminal region of ATM possesses homology to the catalytic domain of mammalian PI 3-kinase, it has been speculated that ATM may phosphorylate inositol phospholipids. However, despite conducting lipid phosphorylation assays under various conditions and with a variety of potential substrates, no ATM-associated lipid kinase activity was detected in our ATM preparations. These data are thus consistent with recent studies demonstrating that ATM-containing immunoprecipitates possess no detectable lipid kinase activity (Jung et al., 1997). Although we cannot discount the possibility that ATM modifies particular PI derivatives under certain conditions or in association with additional cofactors, we tentatively conclude that, as has been proposed for DNA-PKcs (Hartley et al., 1995) and FRAP (Brown et al., 1995), ATM is not a lipid kinase.

In contrast, our purified ATM preparations consistently possess protein serine/threonine kinase activity.

Recently (Keegan et al., 1996) have performed rough experiments which might suggest that ATM-containing immunoprecipitates phosphorylate an ~350 kDa polypeptide, suggesting that ATM can modify itself (though the preparations would have contained all sorts of impurities, including kinases). We observe that purified ATM preparations are capable of some degree of ATM auto-phosphorylation.

In addition, we have tested ATM for its ability to modify a variety of other polypeptides. Notably, despite the fact that IkB has been implicated as an ATM target by in vivo functional studies (Jung et al., 1995) and has recently been reported to be phosphorylated by ATM-containing immunoprecipitates (Jung et al., 1997), under our assay conditions we do not detect significant IkB phosphorylation by ATM. Although alternatives exist, one explanation for this discrepancy is that IkB phosphorylation detected in the studies of (Jung et al., 1997) was mediated by a co-immunoprecipitating factor that is separated from ATM during our purification scheme.

Another protein that has been implicated as a possible ATM target by virtue of defective regulation in A-T cells is RPA (Liu and Weaver, 1993; Cheng et al., 1996). However, we have been unable to detect significant phosphorylation of RPA by ATM, suggesting that ATM regulates RPA indirectly. In contrast to the above, we observe low but detectable phosphorylation of Sp1 and the 70 kDa subunit of Ku by ATM. Although the significance of these phosphorylation events is uncertain, these findings raise the interesting possibilities that ATM plays a role in regulating Sp1-dependent transcription and controlling the activity of the Ku/DNA-PKcs holoenzyme.

By far the most efficient substrate for ATM that we have identified, however, is p53. Importantly, the p53 kinase activity we have detected consistently co-purifies with ATM, elutes from the final DNA affinity purification step with the same profile as the ATM polypeptide itself, and further co-purifies with ATM through an additional stringent immunoprecipitation procedure. These data provide strong indication that p53 kinase activity is an inherent property of the ATM polypeptide.

In a manner strikingly reminiscent of the activation of DNA-PK by DNA strand breaks and ds to ss DNA transitions, we find that ATM and ATR associated p53 kinase activity is stimulated markedly by the addition of a DNA cofactor. There are several reasons why this DNA-stimulated protein kinase activity is unlikely to be mediated by contaminating DNA-PK. First, titration studies reveal that, to provide the observed level of p53 phosphorylation, the DNA-PKcs content of ATM and ATR preparations would have to be essentially as great as that of ATM itself. Clearly, this is not the case—silver staining and Western blotting reveal that, if any residual DNA-PK does exist in our most purified ATM and ATR preparations, it is present at levels undetectable by the methods employed in this study. Second, the substrate specificity observed in ATM and ATR preparations is distinct from that of DNA-PK. Third, whereas ATM and ATR-associated kinase activity is stimulated similarly by supercoiled and linear plasmid molecules, DNA-PK is only activated strongly by the latter.

There are several possible ways in which ATM and ATR might be stimulated by DNA, and each of these may contribute to the effects that we observe. (The mechanism of action provides no limitation to the nature and scope of the present invention.)

One possibility is that DNA binding by ATM and ATR activates the catalytic potential of the proteins directly. Another is that the co-localisation of ATM and ATR and its target DNA binding protein on the same DNA molecule serves to potentiate interactions between the kinase and its target. In line with one or both of the above models, we have observed that ATM auto-phosphorylation is also enhanced by DNA, albeit to a lesser degree than that observed with p53.

Alternatively, at least part of the dramatic stimulation of p53 phosphorylation upon DNA addition could be explained by the binding of p53 to DNA inducing a conformational change in p53 that makes it a more effective ATM or ATR substrate. Thus, Ser-15 and Thr-18 might only become accessible to ATM after p53 is bound to DNA. In accordance with such a model, it is known that the conformation of p53 does change upon binding to DNA (Halazonetis et al., 1993), and it has been observed that several naturally occurring p53 mutants that are defective in sequence-specific DNA binding exhibit reduced phosphorylation at Ser-15 (Ullrich et al., 1993).

Given the DNA-PK paradigm, and because of the previously described role of ATM in DNA damage signalling, it might be tempting to speculate that ATM or ATR protein kinase activity in vivo is triggered by specific types of DNA damage or stalled DNA replication forks that occur in response to IR. However, unlike DNA-PK, which is activated strongly in vitro only by DNA molecules bearing perturbations in the DNA double-helix, we find that ATM interacts with all types of DNA structure that we have tested. It is, therefore, possible that ATM is active constitutively in mammalian cells. An alternative model, which we currently favour, is that ATM and ATR associate with other polypeptides rather like DNA-PKcs interacts with Ku, and it is the function of these additional components to restrict ATM or ATR activity under normal circumstances and only allow their activation after exposure to DNA damaging agents. In this regard, it is interesting to note that yeast genetic data indicate the S. cerevisiae and S. pombe homologues of ATM or ATR function in conjunction with other polypeptides in DNA damage signalling (reviewed in Elledge, 1996; Carr, 1997), and that biochemical studies reveal that ATM exists as a large complex of ~2 MDa in crude cell extracts (GCMS, unpublished data).

Together with genetic data indicating that ATM functions upstream of p53 in a pathway for signalling IR-induced DNA damage, our findings provide indication that, following genomic insult, ATM and ATR phosphorylate p53 directly. Such a model would help to explain the deficient up-regulation of p53 in response to IR in A-T cells and this, in turn, would explain at least some of the cell cycle checkpoint control defects of A-T cells. Interestingly, recent studies indicate that ATM interacts with p53 directly (Watters et al., 1997) providing a possible mechanism for optimising the efficiency of ATM-mediated p53 phosphorylation in the cellular context. Indeed, since p53 itself binds to DNA strand breaks and DNA insertion loops (Balkalkin et al., 1994; Lee et al., 1995; Reed et al., 1995), p53 could actually play a role in targeting ATM or ATR to sites of DNA damage. Such a model is particularly attractive when one considers that Ser-15 and Thr-18 reside in conserved and functionally important regions of the p53 polypeptide. Moreover, Ser-15 of p53 has been shown to be phosphorylated in vivo (reviewed in Anderson and Lees-Miller, 1992; Steegenga et al., 1996). In addition, although Thr-18 has not yet been identified as a physiological site for p53 modification, it is noteworthy that this residue is highly conserved in p53, and that around 8% of p53 phosphorylation in vivo occurs at Thr residues (Samad et al., 1986). In light of these points, it will clearly be of great interest to analyse the phosphorylation status of p53 Ser-15 and Thr-18 in wild-type and A-T cells, and to determine their degree of phosphorylation in response to IR.

Interestingly, phosphorylation of the N-terminal region of p53 has been proposed to effect both the stability and the transcriptional activation potential of p53 (reviewed in Ko and Prives, 1996; Steegenga et al., 1996). Indeed, mutation of Ser-15 impairs the capacity of p53 to prevent S-phase progression and affects p53 stability (Fiscella et al., 1993). Furthermore, p53 mutants unable to activate transcription show reduced phosphorylation at this site (Ullrich et al., 1993). Although no experiments have investigated the role of Thr-18 in p53 function directly, it is noteworthy that this residue forms part of the minimal p53 binding site for Mdm2, which functions as a negative regulator of p53 function (Oliner et al., 1993). Significantly, Mdm-2 binding has been linked both to repressing p53-dependent transcriptional activation and targeting p53 for degradation within the cell (Momand et al., 1992; Oliner et al., 1993; Kubbutat et al., 1997). An attractive scenario, therefore, is that phosphorylation of p53 by ATM or ATR may inhibit Mdm2 interaction, thus both stabilising p53 and de-repressing its transcriptional activity. Consistent with this, we find that the binding of p53-derived peptides to Mdm2 is strongly inhibited by phosphorylation of Thr18.

It is emphasized that suggested mechanisms of action and models for ATM and p53 function discussed above are presented without limitation to the nature and scope of the present invention.

Experimental Procedures

DNA Interaction Studies

Oligonucleotides: one DNA strand containing a 5' biotin group (indicated by a "B" below) was annealed with complementary oligonucleotide(s) and bound to streptavidin-coated iron-oxide particles (Dynabeads; Dynal, Oslo, Norway). HeLa nuclear extract, or ATM enriched extract (Q-Sepharose pool; see below) was incubated on ice for 30 min. with the DNA-iron oxide particles. After washing with 5×0.5 ml of D* Buffer (25 mM HEPES-KOH, pH 7.6, 20% glycerol, 2 mM MgCl2, 0.2 mM EDTA, 1 mM DTT, 0.5 mM PMSF, 1 mM Na Metabisulfite) containing 50 mM KCl, protein was eluted with 500 mM KCl D* buffer or in gradual stepwise manner with KCl concentrations of 100 mM, 250 mM and 500 mM in buffer D*. Fractions were analysed for ATM protein content by Western blotting using a previously described rabbit polyclonal antisera raised against amino acid residues 1980–2337 of ATM (Lakin et al., 1996).

Oligonucleotides:

ds 15-mer (SEQ ID NO:12) 5' B-CCTGCCCTTGCCTGA-3' (SEQ ID NO:13) 5' TCAGGCAAGGGCAGG-3' ds 25-mer (SEQ ID NO:14) 5' B-CCTGCCCTTGCCT-GACGCTATTAGT-3' (SEQ ID NO:15) 5' ACTAAT-AGCGTCAGGCAAGGGCAGG-3' ds 50-mer (SEQ ID NO:16) 5' B-TTGTAAAACGACGGCCAGT-GAATTCATCATCAATAATATACC TTATTTTG-3'

(SEQ ID NO:17) 5' CAAAATAAGGTATATTATTGAT-GATGAATTCACTGGCCGTCGTTTTACAA-3' ds75-mer (SEQ ID NO:18)5' B-GATCGAATCCGATAGAGTATA-GATAGAGTAAAGTTTAAATACTTA TATAGATAGAG-TATAGATAGAGGGTTCAAA-3'

(SEQ ID NO:19) 5' TTTGAACCCTCTATCTATACTC-TATCTATATAAGTATTTAAAC TTTACTCTATC-TATACTCTATCGGATTCGATC-3' ss 50-mer (SEQ ID NO:20) 5' B-TTGTAAAACGACGGCCAGT-GAATTCATCATCAATAATATACCTT ATTTTG 3'

For the following, a biotinylated 100-mer oligonucleotide (DYNO) was used as a "backbone" to which other oligonucleotides were annealed.

(SEQ ID NO:21) DYNO 5' B-CCTGCCCTTGCCT-GACGCTATTAGTTCATCTATTTGTTTTG CTAATTC-GATTGGAATCGAAACGGTCACATAT-TCTTTTTTGACTGATTTCCTCGGCATA-3' nicked oligo, DYNO+DAM2+DAM3:ds/ss transition, DYNO+DAM3; gapped ds oligo, DYNO+DAM3+DAM5; 10 bp insertion, DYNO+DAM6. DAM2:

(SEQ ID NO:22) 5' TATGCCGAGGAAATCAGT-CAAAAAAGAATATGTGACCGTTTCGATTCCAA-3'

DAM3:

(SEQ ID NO:23) 5' TCGAATTAGCAAAACAAATAGAT-GAACTAATAGCGTCAGGCAAGGGCAGG-3'

DAM5: (SEQ ID NO:24) 5' TATGCCGAGGAAATC-3'

DAM6: (SEQ ID NO:25)

5' TATGCCGAGGAAATCAGTCAAAAAA-GAATATGTGACCGTTTCGAATTAG-CAAAACAAATAGATGA ACTAATAGCGTCAG-GCAAGGGCAGG-3'

ATM Purification

All steps were performed at 4° C. HeLa nuclear extract (20 ml) was applied to a Q-Sepharose column (35 ml, 1.5×20 cm) equilibrated in D* buffer (25 mM HEPES-KOH, pH 7.6, 20% glycerol, 2 mM MgCl$_2$, 0.2 mM EDTA, 1 mM DTT, 0.5 mM PMSF, 1 mM Na Metabisulfite) containing 50 mM KCl. After washing with 2 column vol. of 50 mM KCl D*, protein was eluted with a continuous salt gradient of 50 mM–500 mM KCl in D* buffer. ATM eluted between 160 and 200 mM KCl. Fractions containing ATM and devoid of DNA-PK (as judged by Western blot analysis) were pooled and, after diluting to 100 mM KCl in D* buffer, were loaded onto a heparin agarose column (1.5×6 cm) pre-equilibrated in 100 mM KCl D* buffer. The column was washed with 2 column vol. of 100 mM KCl D* buffer before eluting with a continuous gradient of 50 mM–500 mM KCl in buffer D*. ATM was again followed by Western blot analysis and eluted between 200 and 220 mM KCl. Peak fractions were pooled and dialysed against 50 mM buffer D*. Peak ATM fractions were then incubated with gentle mixing for 1 h. with 200 µg biotinylated 50 bp ds DNA conjugated to streptavidin iron-oxide particles. Unbound protein was rebound to fresh DNA-iron oxide particles. Particles were collected via a magnet and were washed 5× with 0.5 ml of 50 mM KCl D* buffer before eluting ATM with 2×75 µl 500 mM KCl buffer D*. Purified ATM was snap-frozen and stored at −70° C.

ATR Purification

ATR purification was carried out as set out in the description.

Immunological Methods

Western immunoblot analysis was performed as previously (Lakin et al., 1996). Sp1 antisera were purchased from Serotec Ltd. (Oxford, UK). RPA-p70 and RNA polymerase II antisera were also utilised. Phospho-specific antisera were generated as described herein.

Immunoprecipitations were performed by incubating biotinylated or untreated purified ATM in parallel with serum for 1 h. on ice in D* buffer containing 50 mM KCl. Protein A Sepharose was added and the reaction incubated with slow rotation for a further h. at 4° C. Beads were washed at high stringency seven times in 500 μl of D* buffer containing 500 mM KCl and 0.1% NP-40. Biotinylated immunoprecipitated proteins were visualised by 7% SDS-PAGE followed by Western blotting and probing with streptavidin-conjugated horse-radish peroxidase. Un-biotinylated immunoprecipitated proteins were washed a further two times in 500 μl 1×Z' buffer prior to addition to kinase reactions (see below).

Phosphorylation Assays

Kinase reactions were performed in 20 μl containing: 10 μl Z' buffer (25 mM HEPES-KOH pH 7.9, 50 mM KCl, 10 mM $MgCl_2$, 20% glycerol, 0.1% NP-40, 1 mM DTT); 11 fmol ATM, DNA-PK or cyclin A/cdk2; 50–100 ng substrate and 0–30 fmol of DNA. Reactions were assembled and incubated for 3 min. on ice prior to addition of 10 μCi [γ-$^{32}$P] ATP and incubation at 30° C. for 15 min. Phosphorylated proteins were subjected to 7% SDS-PAGE and visualised by autoradiography.

Mapping of p53 Phosphorylation Sites

Recombinant p53 (10–20 pmol; purified as previously (Hupp et al., 1992)) was incubated with 12-24 ng of purified ATM or DNA-PK in the presence of 100 μM ATP containing $10^6$–$10^7$ cpm/nmol [$^{32}$P]-γATP under reaction conditions described above. Linearised (pG$_{13}$-CAT) or supercoiled (pBS-SK; Stratagene, USA) DNA were included in DNA-PK and ATM reactions, respectively, where indicated. After 30 min. at 30° C., reactions were terminated by transferring to an ice water bath. Following TCA precipitation, labelled p53 was resolved by 10% SDS-PAGE and visualised by autoradiography. The gel section containing labelled p53 was excised and the protein eluted and TCA precipitated as described (Alessi et al., 1996). The washed TCA pellet was either digested directly with alkylated trypsin (Promega, Southampton, UK) or, for ASP-N digestion, solubilised first in 0.2% v/v Triton X-100 and digested overnight with 1:5 w:w Asp-N (Boehringer Mannheim) and, where indicated, followed by overnight digestion with trypsin. The supernatant containing digested protein was chromatographed on a Vydac 218TP54 C18 column (Separations Group, Hesperia, Calif.) equilibrated with 0.1% v/v triflouroacetic acid (TFA), and eluted with a linear acetronitrile gradient. The flow rate was 0.8 ml/min. and 0.4 ml fractions were collected. Peak fractions were coupled covalently to a Sequelon acrylamide membrane and analysed on an Applied Biosystems 470A sequencer using the modified programme described by (Stokoe et al., 1992) to determine Edman degradation cycle numbers corresponding to radioactivity release.

Additional Purification of ATM

Purification using NTA has been described already above.

REFERENCES

These references and all others mentioned herein are incorporated by reference.

Alessi et al., (1996), *EMBO J.* 15, 6541–6551.
Anderson et al., (1992), *Gene Express*, 2, 283–314.
Artuso et al., (1995), *Oncogene* 11, 1427–1435.
Balkalkin et al., (1994), *Proc. Natl. Acad. Sci. USA* 91, 413–417.
Barlow et al., (1996), *Cell* 86, 159–171.
Beamish et al., (1994), *Radiat. Res.* 138, S130–133.
Beamish, H. and Lavin, M. F. (1994), *Int. J. Radiat. Biol.* 65, 175–184.
Brown et al., (1995), *Nature* 377, 441–446.
Brown, E. J. and Schreiber, S. L. (1996) *Cell* 86, 517–520.
Brown et al., (1997), *Proc. Natl. Acad. Sci. USA* 94, 1840–1845.
Carr, A. M. (1997), *Current Opinion in Genetics & Development* 7, 93–98.
Chen et al., (1993) *Mol. and Cell Biol.* 13(7) 4107–4114.
Chen, G and Lee, E. Y.-H P. (1996), *J. Biol. Chem.* 271, 33693–33697.
Cheng et al., (1996), *Radiother. Oncol.* 39, 43–52.
Cimprich et al, (1996). *Proc. Natl. Acad. Sci. USA.* 93, 2850–2855.
Dutta et al., (1993) *Nature* 79–82
Easton, D. F. (1994), *International Journal of Radiation Biology* 66, S177–S182.
Elledge, S. J. (1996), *Science* 274, 1664–1672.
Fiscella et al., (1993), *Oncogene* 8, 1519–1528.
Fitzgerald et al., (1997), *Nature Genetics* 15, 307–310.
Goffeau et al., (1996) *Science* 274, 546.
Gottlieb, T. M. and Jackson, S. P. (1993), *Cell* 72, 131–142.
Gu et al. (1997) *Nature* 387 819–822.
Hartley et al., (1995), *Cell* 82, 849–856.
Haupt et al., (1997) *Nature* 387 296–299.
Hunter, T. (1995), *Cell* 83, 1–4.
Hupp et al., (1992), *Cell* 71, 875–886.
Jackson, S. P. (1995), *Current Biology* 5, 1210–1212.
Jackson, S. P. (1996), *Cancer Surveys* 28; Genetic Instability in Cancer, 261–279.
Jackson, S. P. (1996), *Current Opinion in Genetics & Development* 6, 19–25.
Jackson, S. P. and Jeggo, P. A. (1995), *Trends Biochem. Sci.* 20, 412–415.
Jung et al., (1997), *Cancer Res.* 57, 24–27.
Jung et al., (1995), *Science* 268, 1619–1621.
Kao et al., (1990), *Virology* 179: 806–814.
Kapeller, R. and Cantley, L. C. (1994), *Bioessays* 16, 565–576.
Kastan et al., (1992), *Cell* 71, 587–597.
Keegan et al., (1996), *Genes & Dev.* 10, 2423–2437.
Keith, C. T. and Schreiber, S. L. (1995), *Science* 270, 50–51.
Khanna, K. and Lavin, M. F. (1993), *Oncogene* 8, 3307–3312.
Khanna et al., (1995), *Oncogene* 11, 609–618.
Ko, L. J. and Prives, C. (1996), *Genes & Dev.* 10, 1054–1072.
Kubbutat et al., (1997), *Nature* 387 299–303.
Kussi et al, (1996), *Science* 274 948–953.
Lakin et al., (1996), *Oncogene* 13, 2707–2716.
Lee et al., (1995), *Cell* 81, 1013–1020.
Lees-Miller et al., (1992), *Mol. Cell. Biol.* 12, 5041–5049.
Li and Botchan, (1993) *Cell* 73 1207–1221.
Lieber et al., (1997), *Current Opinion in Genetics & Development* 7, 99–104.
Lill et al. (1997) *Nature* 387, 823–827.
Lin et al., (1994) *Genes & Development* 8: 1235–1246.
Liu, V. F. and Weaver, D. T. (1993), *Mol. Cell. Biol.* 13, 7222–7231.
Lu, X. and Lane, D. P. (1993), *Cell* 75, 765–778.
Maheswaran et al., (1993) *PNAS USA* 90 5100–5104.
Martin et al., (1992) *J. Biol. Chem.* 268(18) 13062–13067.
Meijer (1996), *Trends Cell Biol.* 6, 393–397.
Meyn, M. S. (1995), *Cancer Res.* 55, 5991–6001.
Milne et al., (1992), *Oncogene* 7, 1361–1369.

Momand et al., (1992), *Cell* 69, 1237–1245.
O'Connor et al., (1995) *The EMBO J.* 14(24) 6184–6192.
Okada et al., (1994), *J. Biol. Chem.* 269, 3563–3567.
Oliner et al., (1993), *Nature* 362, 857–860.
Picksley et al., (1994) *Oncogene* 9 2523–2529.
Poltoratsky et al., (1995), *J. Immunol.* 155, 4529–4533.
Reed et al., (1995), *Proc. Natl. Acad. Sci. USA* 92, 9455–9459.
Samad et al., (1986), *Proc. Natl. Acad. Sci. USA* 83, 897–901.
Savitsky et al., (1995a), *Science* 268, 1749–1753.
Savitsky et al., (1995b), *Hum. Mol. Genet.* 4, 2025–2032.
Seto et al., (1992) *PNAS USA* 89 12028–12032.
Shiloh, Y. (1995), *Eur. J. Hum. Genet.* 3, 116–138.
Soussi et al (1990) *Oncogene* 5 945–952.
Steegenga et al., (1996), *J. Mol. Biol.* 263, 103–113.
Stokoe et al., (1992), *EMBO J.* 11, 3985–3994.
Thut et al., (1995) *Science* 267 (5194) 100–104.
Truant et al., (1993) *J. Biol. Chem.* 268(4) 2284.
Ullrich et al., (1993), *Proc. Natl. Acad. Sci. USA* 90, 5954–5958.
Vlahos et al., (1994), *J. Biol. Chem.* 269, 5241–5248.
Wang et al., (1995) *Nature Genetics* 10, 188–195.
Wang, Y. and Prives, C. (1995), *Nature* 376, 88–91.
Watters et al., (1997), *Oncogene* 14, 1911–1921.
Xiao et al., (1994), *Mol. & Cell. Biol.* 14(10) 7013–7024.
Xu, Y. and Baltimore, D. (1996), *Genes & Dev.* 10, 2401–2410.
Zakian, V. A. (1995), *Cell* 82, 685–687.

---

The invention claimed is:

1. An assay method for identifying a compound able to modulate the interaction between ATR (ATM-Rad3-related) and p53, the method including the steps of:
   (a) bringing into contact (i) ATR or a fragment of ATR which phosphorylates p53, (ii) p53 or a fragment of p53 which includes a site which is phosphorylated by ATR, and (iii) a test compound; and
   (b) determining phosphorylation at said site, wherein an increase or decrease in the phosphorylation at said site in the presence relative to the absence of test compound is indicative that the compound is able to modulate the interaction between ATR and p53.

2. The method according to claim 1, wherein said compound is able to modulate phosphorylation of p53 by ATR.

* * * * *

SEQUENCE LISTING

```
<160> NUMBER OF SEQ ID NOS: 26

<210> SEQ ID NO 1
<211> LENGTH: 3056
<212> TYPE: PRT
<213> ORGANISM: Homo sapiens

<400> SEQUENCE: 1

Met Ser Leu Val Leu Asn Asp Leu Leu Ile Cys Cys Arg Gln Leu Glu
  1               5                  10                  15

His Asp Arg Ala Thr Glu Arg Lys Lys Glu Val Glu Lys Phe Lys Arg
             20                  25                  30

Leu Ile Arg Asp Pro Glu Thr Ile Lys His Leu Asp Arg His Ser Asp
         35                  40                  45

Ser Lys Gln Gly Lys Tyr Leu Asn Trp Asp Ala Val Phe Arg Phe Leu
     50                  55                  60

Gln Lys Tyr Ile Gln Lys Glu Thr Glu Cys Leu Arg Ile Ala Lys Pro
 65                  70                  75                  80

Asn Val Ser Ala Ser Thr Gln Ala Ser Arg Gln Lys Lys Met Gln Glu
                 85                  90                  95

Ile Ser Ser Leu Val Lys Tyr Phe Ile Lys Cys Ala Asn Arg Arg Ala
            100                 105                 110

Pro Arg Leu Lys Cys Gln Glu Leu Leu Asn Tyr Ile Met Asp Thr Val
        115                 120                 125

Lys Asp Ser Ser Asn Gly Ala Ile Tyr Gly Ala Asp Cys Ser Asn Ile
    130                 135                 140

Leu Leu Lys Asp Ile Leu Ser Val Arg Lys Tyr Trp Cys Glu Ile Ser
145                 150                 155                 160

Gln Gln Gln Trp Leu Glu Leu Phe Ser Val Tyr Phe Arg Leu Tyr Leu
                165                 170                 175

Lys Pro Ser Gln Asp Val His Arg Val Leu Val Ala Arg Ile Ile His
            180                 185                 190

Ala Val Thr Lys Gly Cys Cys Ser Gln Thr Asp Gly Leu Asn Ser Lys
        195                 200                 205

Phe Leu Asp Phe Phe Ser Lys Ala Ile Gln Cys Ala Arg Gln Glu Lys
    210                 215                 220

Ser Ser Ser Gly Leu Asn His Ile Leu Ala Ala Leu Thr Ile Phe Leu
225                 230                 235                 240

Lys Thr Leu Ala Val Asn Phe Arg Ile Arg Val Cys Glu Leu Gly Asp
                245                 250                 255
```

```
Glu Ile Leu Pro Thr Leu Leu Tyr Ile Trp Thr Gln His Arg Leu Asn
            260                 265                 270

Asp Ser Leu Lys Glu Val Ile Ile Glu Leu Phe Gln Leu Gln Ile Tyr
        275                 280                 285

Ile His His Pro Lys Gly Ala Lys Thr Gln Glu Lys Gly Ala Tyr Glu
        290                 295                 300

Ser Thr Lys Trp Arg Ser Ile Leu Tyr Asn Leu Tyr Asp Leu Leu Val
305                 310                 315                 320

Asn Glu Ile Ser His Ile Gly Ser Arg Gly Lys Tyr Ser Ser Gly Phe
                325                 330                 335

Arg Asn Ile Ala Val Lys Glu Asn Leu Ile Glu Leu Met Ala Asp Ile
            340                 345                 350

Cys His Gln Val Phe Asn Glu Asp Thr Arg Ser Leu Glu Ile Ser Gln
            355                 360                 365

Ser Tyr Thr Thr Thr Gln Arg Glu Ser Ser Asp Tyr Ser Val Pro Cys
        370                 375                 380

Lys Arg Lys Lys Ile Glu Leu Gly Trp Glu Val Ile Lys Asp His Leu
385                 390                 395                 400

Gln Lys Ser Gln Asn Asp Phe Asp Leu Val Pro Trp Leu Gln Ile Ala
                405                 410                 415

Thr Gln Leu Ile Ser Lys Tyr Pro Ala Ser Leu Pro Asn Cys Glu Leu
            420                 425                 430

Ser Pro Leu Leu Met Ile Leu Ser Gln Leu Leu Pro Gln Gln Arg His
            435                 440                 445

Gly Glu Arg Thr Pro Tyr Val Leu Arg Cys Leu Thr Glu Val Ala Leu
        450                 455                 460

Cys Gln Asp Lys Arg Ser Asn Leu Glu Ser Ser Gln Lys Ser Asp Leu
465                 470                 475                 480

Leu Lys Leu Trp Asn Lys Ile Trp Cys Ile Thr Phe Arg Gly Ile Ser
                485                 490                 495

Ser Glu Gln Ile Gln Ala Glu Asn Phe Gly Leu Leu Gly Ala Ile Ile
            500                 505                 510

Gln Gly Ser Leu Val Glu Val Asp Arg Glu Phe Trp Lys Leu Phe Thr
        515                 520                 525

Gly Ser Ala Cys Arg Pro Ser Cys Pro Ala Val Cys Cys Leu Thr Leu
        530                 535                 540

Ala Leu Thr Thr Ser Ile Val Pro Gly Ala Val Lys Met Gly Ile Glu
545                 550                 555                 560

Gln Asn Met Cys Glu Val Asn Arg Ser Phe Ser Leu Lys Glu Ser Ile
                565                 570                 575

Met Lys Trp Leu Leu Phe Tyr Gln Leu Glu Gly Asp Leu Glu Asn Ser
            580                 585                 590

Thr Glu Val Pro Pro Ile Leu His Ser Asn Phe Pro His Leu Val Leu
            595                 600                 605

Glu Lys Ile Leu Val Ser Leu Thr Met Lys Asn Cys Lys Ala Ala Met
        610                 615                 620

Asn Phe Phe Gln Ser Val Pro Glu Cys Glu His His Gln Lys Asp Lys
625                 630                 635                 640

Glu Glu Leu Ser Phe Ser Glu Val Glu Glu Leu Phe Leu Gln Thr Thr
                645                 650                 655

Phe Asp Lys Met Asp Phe Leu Thr Ile Val Arg Glu Cys Gly Ile Glu
            660                 665                 670
```

-continued

```
Lys His Gln Ser Ser Ile Gly Phe Ser Val His Gln Asn Leu Lys Glu
            675                 680                 685

Ser Leu Asp Arg Cys Leu Leu Gly Leu Ser Glu Gln Leu Leu Asn Asn
        690                 695                 700

Tyr Ser Ser Glu Ile Thr Asn Ser Glu Thr Leu Val Arg Cys Ser Arg
705                 710                 715                 720

Leu Leu Val Gly Val Leu Gly Cys Tyr Cys Tyr Met Gly Val Ile Ala
                725                 730                 735

Glu Glu Glu Ala Tyr Lys Ser Glu Leu Phe Gln Lys Ala Asn Ser Leu
            740                 745                 750

Met Gln Cys Ala Gly Glu Ser Ile Thr Leu Phe Lys Asn Lys Thr Asn
        755                 760                 765

Glu Glu Phe Arg Ile Gly Ser Leu Arg Asn Met Met Gln Leu Cys Thr
    770                 775                 780

Arg Cys Leu Ser Asn Cys Thr Lys Lys Ser Pro Asn Lys Ile Ala Ser
785                 790                 795                 800

Gly Phe Phe Leu Arg Leu Leu Thr Ser Lys Leu Met Asn Asp Ile Ala
                805                 810                 815

Asp Ile Cys Lys Ser Leu Ala Ser Phe Ile Lys Lys Pro Phe Asp Arg
            820                 825                 830

Gly Glu Val Glu Ser Met Glu Asp Asp Thr Asn Gly Asn Leu Met Glu
        835                 840                 845

Val Glu Asp Gln Ser Ser Met Asn Leu Phe Asn Asp Tyr Pro Asp Ser
    850                 855                 860

Ser Val Ser Asp Ala Asn Glu Pro Gly Glu Ser Gln Ser Thr Ile Gly
865                 870                 875                 880

Ala Ile Asn Pro Leu Ala Glu Glu Tyr Leu Ser Lys Gln Asp Leu Leu
                885                 890                 895

Phe Leu Asp Met Leu Lys Phe Leu Cys Leu Cys Val Thr Thr Ala Gln
            900                 905                 910

Thr Asn Thr Val Ser Phe Arg Ala Ala Asp Ile Arg Arg Lys Leu Leu
        915                 920                 925

Met Leu Ile Asp Ser Ser Thr Leu Glu Pro Thr Lys Ser Leu His Leu
    930                 935                 940

His Met Tyr Leu Met Leu Leu Lys Glu Leu Pro Gly Glu Glu Tyr Pro
945                 950                 955                 960

Leu Pro Met Glu Asp Val Leu Glu Leu Leu Lys Pro Leu Ser Asn Val
                965                 970                 975

Cys Ser Leu Tyr Arg Arg Asp Gln Asp Val Cys Lys Thr Ile Leu Asn
            980                 985                 990

His Val Leu His Val Val Lys Asn Leu Gly Gln Ser Asn Met Asp Ser
        995                 1000                1005

Glu Asn Thr Arg Asp Ala Gln Gly Gln Phe Leu Thr Val Ile Gly Ala
    1010                1015                1020

Phe Trp His Leu Thr Lys Glu Arg Lys Tyr Ile Phe Ser Val Arg Met
1025                1030                1035                1040

Ala Leu Val Asn Cys Leu Lys Thr Leu Leu Glu Ala Asp Pro Tyr Ser
                1045                1050                1055

Lys Trp Ala Ile Leu Asn Val Met Gly Lys Asp Phe Pro Val Asn Glu
            1060                1065                1070

Val Phe Thr Gln Phe Leu Ala Asp Asn His His Gln Val Arg Met Leu
        1075                1080                1085

Ala Ala Glu Ser Ile Asn Arg Leu Phe Gln Asp Thr Lys Gly Asp Ser
```

-continued

```
                1090                1095                1100
Ser Arg Leu Leu Lys Ala Leu Pro Leu Lys Leu Gln Gln Thr Ala Phe
1105                1110                1115                1120

Glu Asn Ala Tyr Leu Lys Ala Gln Glu Gly Met Arg Glu Met Ser His
                1125                1130                1135

Ser Ala Glu Asn Pro Glu Thr Leu Asp Glu Ile Tyr Asn Arg Lys Ser
            1140                1145                1150

Val Leu Leu Thr Leu Ile Ala Val Val Leu Ser Cys Ser Pro Ile Cys
        1155                1160                1165

Glu Lys Gln Ala Leu Phe Ala Leu Cys Lys Ser Val Lys Glu Asn Gly
1170                1175                1180

Leu Glu Pro His Leu Val Lys Lys Val Leu Glu Lys Val Ser Glu Thr
1185                1190                1195                1200

Phe Gly Tyr Arg Arg Leu Glu Asp Phe Met Ala Ser His Leu Asp Tyr
                1205                1210                1215

Leu Val Leu Glu Trp Leu Asn Leu Gln Asp Thr Glu Tyr Asn Leu Ser
            1220                1225                1230

Ser Phe Pro Phe Ile Leu Leu Asn Tyr Thr Asn Ile Glu Asp Phe Tyr
        1235                1240                1245

Arg Ser Cys Tyr Lys Val Leu Ile Pro His Leu Val Ile Arg Ser His
        1250                1255                1260

Phe Asp Glu Val Lys Ser Ile Ala Asn Gln Ile Gln Glu Asp Trp Lys
1265                1270                1275                1280

Ser Leu Leu Thr Asp Cys Phe Pro Lys Ile Leu Val Asn Ile Leu Pro
            1285                1290                1295

Tyr Phe Ala Tyr Glu Gly Thr Arg Asp Ser Gly Met Ala Gln Gln Arg
        1300                1305                1310

Glu Thr Ala Thr Lys Val Tyr Asp Met Leu Lys Ser Glu Asn Leu Leu
            1315                1320                1325

Gly Lys Gln Ile Asp His Leu Phe Ile Ser Asn Leu Pro Glu Ile Val
        1330                1335                1340

Val Glu Leu Leu Met Thr Leu His Glu Pro Ala Asn Ser Ser Ala Ser
1345                1350                1355                1360

Gln Ser Thr Asp Leu Cys Asp Phe Ser Gly Asp Leu Asp Pro Ala Pro
            1365                1370                1375

Asn Pro Pro His Phe Pro Ser His Val Ile Lys Ala Thr Phe Ala Tyr
        1380                1385                1390

Ile Ser Asn Cys His Lys Thr Lys Leu Lys Ser Ile Leu Glu Ile Leu
        1395                1400                1405

Ser Lys Ser Pro Asp Ser Tyr Gln Lys Ile Leu Leu Ala Ile Cys Glu
        1410                1415                1420

Gln Ala Ala Glu Thr Asn Asn Val Tyr Lys Lys His Arg Ile Leu Lys
1425                1430                1435                1440

Ile Tyr His Leu Phe Val Ser Leu Leu Leu Lys Asp Ile Lys Ser Gly
                1445                1450                1455

Leu Gly Gly Ala Trp Ala Phe Val Leu Arg Asp Val Ile Tyr Thr Leu
                1460                1465                1470

Ile His Tyr Ile Asn Gln Arg Pro Ser Cys Ile Met Asp Val Ser Leu
            1475                1480                1485

Arg Ser Phe Ser Leu Cys Cys Asp Leu Leu Ser Gln Val Cys Gln Thr
        1490                1495                1500

Ala Val Thr Tyr Cys Lys Asp Ala Leu Glu Asn His Leu His Val Ile
1505                1510                1515                1520
```

```
Val Gly Thr Leu Ile Pro Leu Val Tyr Glu Gln Val Glu Val Gln Lys
        1525                1530                1535

Gln Val Leu Asp Leu Leu Lys Tyr Leu Val Ile Asp Asn Lys Asp Asn
        1540                1545                1550

Glu Asn Leu Tyr Ile Thr Ile Lys Leu Leu Asp Pro Phe Pro Asp His
        1555                1560                1565

Val Val Phe Lys Asp Leu Arg Ile Thr Gln Gln Lys Ile Lys Tyr Ser
    1570                1575                1580

Arg Gly Pro Phe Ser Leu Leu Glu Glu Ile Asn His Phe Leu Ser Val
1585                1590                1595                1600

Ser Val Tyr Asp Ala Leu Pro Leu Thr Arg Leu Glu Gly Leu Lys Asp
        1605                1610                1615

Leu Arg Arg Gln Leu Glu Leu His Lys Asp Gln Met Val Asp Ile Met
        1620                1625                1630

Arg Ala Ser Gln Asp Asn Pro Gln Asp Gly Ile Met Val Lys Leu Val
        1635                1640                1645

Val Asn Leu Leu Gln Leu Ser Lys Met Ala Ile Asn His Thr Gly Glu
        1650                1655                1660

Lys Glu Val Leu Glu Ala Val Gly Ser Cys Leu Gly Glu Val Gly Pro
1665                1670                1675                1680

Ile Asp Phe Ser Thr Ile Ala Ile Gln His Ser Lys Asp Ala Ser Tyr
        1685                1690                1695

Thr Lys Ala Leu Lys Leu Phe Glu Asp Lys Glu Leu Gln Trp Thr Phe
        1700                1705                1710

Ile Met Leu Thr Tyr Leu Asn Asn Thr Leu Val Glu Asp Cys Val Lys
        1715                1720                1725

Val Arg Ser Ala Ala Val Thr Cys Leu Lys Asn Ile Leu Ala Thr Lys
        1730                1735                1740

Thr Gly His Ser Phe Trp Glu Ile Tyr Lys Met Thr Thr Asp Pro Met
1745                1750                1755                1760

Leu Ala Tyr Leu Gln Pro Phe Arg Thr Ser Arg Lys Lys Phe Leu Glu
        1765                1770                1775

Val Pro Arg Phe Asp Lys Glu Asn Pro Phe Glu Gly Leu Asp Asp Ile
        1780                1785                1790

Asn Leu Trp Ile Pro Leu Ser Glu Asn His Asp Ile Trp Ile Lys Thr
        1795                1800                1805

Leu Thr Cys Ala Phe Leu Asp Ser Gly Gly Thr Lys Cys Glu Ile Leu
        1810                1815                1820

Gln Leu Leu Lys Pro Met Cys Glu Val Lys Thr Asp Phe Cys Gln Thr
1825                1830                1835                1840

Val Leu Pro Tyr Leu Ile His Asp Ile Leu Leu Gln Asp Thr Asn Glu
        1845                1850                1855

Ser Trp Arg Asn Leu Leu Ser Thr His Val Gln Gly Phe Phe Thr Ser
        1860                1865                1870

Cys Leu Arg His Phe Ser Gln Thr Ser Arg Ser Thr Thr Pro Ala Asn
        1875                1880                1885

Leu Asp Ser Glu Ser Glu His Phe Phe Arg Cys Cys Leu Asp Lys Lys
        1890                1895                1900

Ser Gln Arg Thr Met Leu Ala Val Val Asp Tyr Met Arg Arg Gln Lys
1905                1910                1915                1920

Arg Pro Ser Ser Gly Thr Ile Phe Asn Asp Ala Phe Trp Leu Asp Leu
        1925                1930                1935
```

-continued

Asn Tyr Leu Glu Val Ala Lys Val Ala Gln Ser Cys Ala Ala His Phe
            1940                1945                1950

Thr Ala Leu Leu Tyr Ala Glu Ile Tyr Ala Asp Lys Lys Ser Met Asp
            1955                1960                1965

Asp Gln Glu Lys Arg Ser Leu Ala Phe Glu Glu Gly Ser Gln Ser Thr
            1970                1975                1980

Thr Ile Ser Ser Leu Ser Glu Lys Ser Lys Glu Glu Thr Gly Ile Ser
1985                1990                1995                2000

Leu Gln Asp Leu Leu Leu Glu Ile Tyr Arg Ser Ile Gly Glu Pro Asp
            2005                2010                2015

Ser Leu Tyr Gly Cys Gly Gly Gly Lys Met Leu Gln Pro Ile Thr Arg
            2020                2025                2030

Leu Arg Thr Tyr Glu His Glu Ala Met Trp Gly Lys Ala Leu Val Thr
            2035                2040                2045

Tyr Asp Leu Glu Thr Ala Ile Pro Ser Ser Thr Arg Gln Ala Gly Ile
            2050                2055                2060

Ile Gln Ala Leu Gln Asn Leu Gly Leu Cys His Ile Leu Ser Val Tyr
2065                2070                2075                2080

Leu Lys Gly Leu Asp Tyr Glu Asn Lys Asp Trp Cys Pro Glu Leu Glu
            2085                2090                2095

Glu Leu His Tyr Gln Ala Ala Trp Arg Asn Met Gln Trp Asp His Cys
            2100                2105                2110

Thr Ser Val Ser Lys Glu Val Glu Gly Thr Ser Tyr His Glu Ser Leu
            2115                2120                2125

Tyr Asn Ala Leu Gln Ser Leu Arg Asp Arg Glu Phe Ser Thr Phe Tyr
            2130                2135                2140

Glu Ser Leu Lys Tyr Ala Arg Val Lys Glu Val Glu Glu Met Cys Lys
2145                2150                2155                2160

Arg Ser Leu Glu Ser Val Tyr Ser Leu Tyr Pro Thr Leu Ser Arg Leu
            2165                2170                2175

Gln Ala Ile Gly Glu Leu Glu Ser Ile Gly Glu Leu Phe Ser Arg Ser
            2180                2185                2190

Val Thr His Arg Gln Leu Ser Glu Val Tyr Ile Lys Trp Gln Lys His
            2195                2200                2205

Ser Gln Leu Leu Lys Asp Ser Asp Phe Ser Phe Gln Glu Pro Ile Met
            2210                2215                2220

Ala Leu Arg Thr Val Ile Leu Glu Ile Leu Met Glu Lys Glu Met Asp
2225                2230                2235                2240

Asn Ser Gln Arg Glu Cys Ile Lys Asp Ile Leu Thr Lys His Leu Val
            2245                2250                2255

Glu Leu Ser Ile Leu Ala Arg Thr Phe Lys Asn Thr Gln Leu Pro Glu
            2260                2265                2270

Arg Ala Ile Phe Gln Ile Lys Gln Tyr Asn Ser Val Ser Cys Gly Val
            2275                2280                2285

Ser Glu Trp Gln Leu Glu Glu Ala Gln Val Phe Trp Ala Lys Lys Glu
            2290                2295                2300

Gln Ser Leu Ala Leu Ser Ile Leu Lys Gln Met Ile Lys Lys Leu Asp
2305                2310                2315                2320

Ala Ser Cys Ala Ala Asn Asn Pro Ser Leu Lys Leu Thr Tyr Thr Glu
            2325                2330                2335

Cys Leu Arg Val Cys Gly Asn Trp Leu Ala Glu Thr Cys Leu Glu Asn
            2340                2345                2350

Pro Ala Val Ile Met Gln Thr Tyr Leu Glu Lys Ala Val Glu Val Ala

-continued

```
            2355                2360                2365

Gly Asn Tyr Asp Gly Glu Ser Ser Asp Glu Leu Arg Asn Gly Lys Met
    2370                2375                2380

Lys Ala Phe Leu Ser Leu Ala Arg Phe Ser Asp Thr Gln Tyr Gln Arg
2385                2390                2395                2400

Ile Glu Asn Tyr Met Lys Ser Ser Glu Phe Glu Asn Lys Gln Ala Leu
            2405                2410                2415

Leu Lys Arg Ala Lys Glu Glu Val Gly Leu Leu Arg Glu His Lys Ile
            2420                2425                2430

Gln Thr Asn Arg Tyr Thr Val Lys Val Gln Arg Glu Leu Glu Leu Asp
            2435                2440                2445

Glu Leu Ala Leu Arg Ala Leu Lys Glu Asp Arg Lys Arg Phe Leu Cys
            2450                2455                2460

Lys Ala Val Glu Asn Tyr Ile Asn Cys Leu Leu Ser Gly Glu Glu His
2465                2470                2475                2480

Asp Met Trp Val Phe Arg Leu Cys Ser Leu Trp Leu Glu Asn Ser Gly
            2485                2490                2495

Val Ser Glu Val Asn Gly Met Met Lys Arg Asp Gly Met Lys Ile Pro
            2500                2505                2510

Thr Tyr Lys Phe Leu Pro Leu Met Tyr Gln Leu Ala Ala Arg Met Gly
            2515                2520                2525

Thr Lys Met Met Gly Gly Leu Gly Phe His Glu Val Leu Asn Asn Leu
            2530                2535                2540

Ile Ser Arg Ile Ser Met Asp His Pro His Thr Leu Phe Ile Ile
2545                2550                2555                2560

Leu Ala Leu Ala Asn Ala Asn Arg Asp Glu Phe Leu Thr Lys Pro Glu
            2565                2570                2575

Val Ala Arg Arg Ser Arg Ile Thr Lys Asn Val Pro Lys Gln Ser Ser
            2580                2585                2590

Gln Leu Asp Glu Asp Arg Thr Glu Ala Ala Asn Arg Ile Ile Cys Thr
            2595                2600                2605

Ile Arg Ser Arg Arg Pro Gln Met Val Arg Ser Val Glu Ala Leu Cys
            2610                2615                2620

Asp Ala Tyr Ile Ile Leu Ala Asn Leu Asp Ala Thr Gln Trp Lys Thr
2625                2630                2635                2640

Gln Arg Lys Gly Ile Asn Ile Pro Ala Asp Gln Pro Ile Thr Lys Leu
            2645                2650                2655

Lys Asn Leu Glu Asp Val Val Val Pro Thr Met Glu Ile Lys Val Asp
            2660                2665                2670

His Thr Gly Glu Tyr Gly Asn Leu Val Thr Ile Gln Ser Phe Lys Ala
            2675                2680                2685

Glu Phe Arg Leu Ala Gly Gly Val Asn Leu Pro Lys Ile Ile Asp Cys
            2690                2695                2700

Val Gly Ser Asp Gly Lys Glu Arg Arg Gln Leu Val Lys Gly Arg Asp
2705                2710                2715                2720

Asp Leu Arg Gln Asp Ala Val Met Gln Gln Val Phe Gln Met Cys Asn
            2725                2730                2735

Thr Leu Leu Gln Arg Asn Thr Glu Thr Arg Lys Arg Lys Leu Thr Ile
            2740                2745                2750

Cys Thr Tyr Lys Val Val Pro Leu Ser Gln Arg Ser Gly Val Leu Glu
            2755                2760                2765

Trp Cys Thr Gly Thr Val Pro Ile Gly Glu Phe Leu Val Asn Asn Glu
    2770                2775                2780
```

```
Asp Gly Ala His Lys Arg Tyr Arg Pro Asn Asp Phe Ser Ala Phe Gln
2785                2790                2795                2800

Cys Gln Lys Lys Met Met Glu Val Gln Lys Lys Ser Phe Glu Glu Lys
                2805                2810                2815

Tyr Glu Val Phe Met Asp Val Cys Gln Asn Phe Gln Pro Val Phe Arg
            2820                2825                2830

Tyr Phe Cys Met Glu Lys Phe Leu Asp Pro Ala Ile Trp Phe Glu Lys
        2835                2840                2845

Arg Leu Ala Tyr Thr Arg Ser Val Ala Thr Ser Ser Ile Val Gly Tyr
    2850                2855                2860

Ile Leu Gly Leu Gly Asp Arg His Val Gln Asn Ile Leu Ile Asn Glu
2865                2870                2875                2880

Gln Ser Ala Glu Leu Val His Ile Asp Leu Gly Val Ala Phe Glu Gln
                2885                2890                2895

Gly Lys Ile Leu Pro Thr Pro Glu Thr Val Pro Phe Arg Leu Thr Arg
            2900                2905                2910

Asp Ile Val Asp Gly Met Gly Ile Thr Gly Val Glu Gly Val Phe Arg
        2915                2920                2925

Arg Cys Cys Glu Lys Thr Met Glu Val Met Arg Asn Ser Gln Glu Thr
    2930                2935                2940

Leu Leu Thr Ile Val Glu Val Leu Leu Tyr Asp Pro Leu Phe Asp Trp
2945                2950                2955                2960

Thr Met Asn Pro Leu Lys Ala Leu Tyr Leu Gln Gln Arg Pro Glu Asp
                2965                2970                2975

Glu Thr Glu Leu His Pro Thr Leu Asn Ala Asp Asp Gln Glu Cys Lys
            2980                2985                2990

Arg Asn Leu Ser Asp Ile Asp Gln Ser Phe Asp Lys Val Ala Glu Arg
        2995                3000                3005

Val Leu Met Arg Leu Gln Glu Lys Leu Lys Gly Val Glu Glu Gly Thr
    3010                3015                3020

Val Leu Ser Val Gly Gly Gln Val Asn Leu Leu Ile Gln Gln Ala Ile
3025                3030                3035                3040

Asp Pro Lys Asn Leu Ser Arg Leu Phe Pro Gly Trp Lys Ala Trp Val
                3045                3050                3055

<210> SEQ ID NO 2
<211> LENGTH: 9385
<212> TYPE: DNA
<213> ORGANISM: Homo sapiens

<400> SEQUENCE: 2
gcgagaggag tcgggatctg cgctgcagcc accgccgcgg ttgatactac tttgaccttc    60
cgagtgcagt gaggcataca tcacaatttg gaattatgca ttggtttatc aatttacttg   120
tttattgtca ccctgctgcc cagatatgac ttcatgagga cagtgatgtg tgttctgaaa   180
ttgtgaacca tgagtctagt acttaatgat ctgcttatct gctgccgtca actagaacat   240
gatagagcta cagaacgaaa gaagaagtt gagaaattta gcgcctgat tcgagatcct    300 gaaacaatta acatctaga tcggcattca gattccaaac aaggaaaata tttgaattgg   360
gatgctgttt ttagattttt acagaaatat attcagaaag aaacagaatg tctgagaata   420
gcaaaaccaa atgtatcagc tcaacacaa gcctccaggc agaaaaagat gcaggaaatc   480
agtagtttgg tcaaatactt catcaaatgt gcaaacagaa gagcacctag ctaaaatgt    540 caagaactct taaattatat catggataca gtgaaagatt catctaatgg tgctatttac   600
```

-continued

```
ggagctgatt gtagcaacat actactcaaa gacattcttt ctgtgagaaa atactggtgt    660
gaaatatctc agcaacagtg gttagaattg ttctctgtgt acttcaggct ctatctgaaa    720
ccttcacaag atgttcatag agttttagtg gctagaataa ttcatgctgt taccaaagga    780
tgctgttctc agactgacgg attaaattcc aaattttttgg acttttttttc caaggctatt    840 cagtgtgcga gacaagaaaa gagctcttca ggtctaaatc atatcttagc agctcttact    900
atcttcctca agactttggc tgtcaacttt cgaattcgag tgtgtgaatt aggagatgaa    960
attcttccca ctttgctttta tatttggact caacataggc ttaatgattc tttaaaagaa   1020
gtcattattg aattatttca actgcaaatt tatatccatc atccgaaagg agccaaaacc   1080
caagaaaaag gtgcttatga atcaacaaaa tggagaagta ttttatacaa cttatatgat   1140
ctgctagtga atgagataag tcatataggga agtagaggaa agtattcttc aggatttcgt   1200
aatattgccg tcaaagaaaa tttgattgaa ttgatggcag atatctgtca ccaggttttt   1260
aatgaagata ccagatcctt ggagatttct caatcttaca ctactacaca aagagaatct   1320
agtgattaca gtgtcccttg caaaaggaag aaaatagaac taggctggga agtaataaaa   1380
gatcaccttc agaagtcaca gaatgatttt gatcttgtgc cttggctaca gattgcaacc   1440
caattaatat caaagtatcc tgcaagttta cctaactgtg agctgtctcc attactgatg   1500
atactatctc agcttctacc ccaacagcga catggggaac gtacaccata tgtgttacga   1560
tgccttacgg aagttgcatt gtgtcaagac aagaggtcaa acctagaaag ctcacaaaag   1620
tcagatttat taaaactctg gaataaaatt tggtgtatta cctttcgtgg tataagttct   1680
gagcaaatac aagctgaaaa ctttggctta cttggagcca taattcaggg tagtttagtt   1740
gaggttgaca gagaattctg gaagttattt actgggtcag cctgcagacc ttcatgtcct   1800
gcagtatgct gtttgacttt ggcactgacc accagtatag ttccaggagc ggtaaaaatg   1860
ggaatagagc aaaatatgtg tgaagtaaat agaagctttt cttttaaagga atcaataatg   1920 aaatggctct tattctatca gttagagggt gacttagaaa atagcacaga agtgcctcca   1980
attcttcaca gtaattttcc tcatcttgta ctggagaaaa ttcttgtgag tctcactatg   2040
aaaaactgta agctgcaat gaattttttc caaagcgtgc cagaatgtga acaccaccaa   2100
aaagataaag aagaacttc attctcagaa gtagaagaac tatttcttca gacaactttt   2160
gacaagatgg acttttttaac cattgtgaga gaatgtggta tagaaaagca ccagtccagt   2220
attggcttct ctgtccacca gaatctcaag gaatcactgg atcgctgtct tctgggatta   2280
tcagaacagc ttctgaataa ttactcatct gagattacaa attcagaaac tcttgtccgg   2340
tgttcacgtc ttttggtggg tgtccttggc tgctactgtt acatgggtgt aatagctgaa   2400
gaggaagcat ataagtcaga attattccag aaagccaact ctctaatgca atgtgcagga   2460
gaaagtatca ctctgtttaa aaataagaca atgaggaat tcagaattgg ttccttgaga   2520
aatatgatgc agctatgtac acgttgcttg agcaactgta ccaagaagag tccaaataag   2580
attgcatctg ctttttttcct gcgattgtta acatcaaagc taatgaatga cattgcagat   2640
atttgtaaaa gtttagcatc cttcatcaaa aagccatttg accgtggaga agtagaatca   2700
atggaagatg atactaatgg aaatctaatg gaggtggagg atcagtcatc catgaatcta   2760
tttaacgatt accctgatag tagtgttagt gatgcaaacg aacctggaga gagccaaagt   2820
accataggtg ccattaatcc tttagctgaa gaatatctgt caaagcaaga tctactttttc   2880 ttagacatgc tcaagttctt gtgtttgtgt gtaactactg ctcagaccaa tactgtgtcc   2940
```

```
tttagggcag ctgatattcg gaggaaattg ttaatgttaa ttgattctag cacgctagaa    3000
cctaccaaat ccctccacct gcatatgtat ctaatgcttt taaaggagct tcctggagaa    3060
gagtacccct tgccaatgga agatgttctt gaacttctga aaccactatc caatgtgtgt    3120
tctttgtatc gtcgtgacca agatgtttgt aaaactattt taaaccatgt ccttcatgta    3180
gtgaaaaacc taggtcaaag caatatggac tctgagaaca caaggatgc tcaaggacag    3240 tttcttacag taattggagc attttggcat ctaacaaagg agaggaaata tatattctct    3300
gtaagaatgg ccctagtaaa ttgccttaaa actttgcttg aggctgatcc ttattcaaaa    3360
tgggccattc ttaatgtaat gggaaaagac tttcctgtaa atgaagtatt tacacaattt    3420
cttgctgaca atcatcacca agttcgcatg ttggctgcag agtcaatcaa tagattgttc    3480
caggacacga agggagattc ttccaggtta ctgaaagcac ttcctttgaa gcttcagcaa    3540
acagcttttg aaaatgcata cttgaaagct caggaaggaa tgagagaaat gtcccatagt    3600
gctgagaacc ctgaaacttt ggatgaaatt tataatagaa aatctgtttt actgacgttg    3660
atagctgtgg ttttatcctg tagccctatc tgcgaaaaac aggctttgtt tgccctgtgt    3720
aaatctgtga agagaatgg attagaacct caccttgtga aaaaggtttt agagaaagtt    3780
tctgaaactt ttggatatag acgtttagaa gactttatgg catctcattt agattatctg    3840
gttttggaat ggctaaatct tcaagatact gaatacaact tatcttcttt tcctttatt     3900 ttattaaact acacaaatat tgaggatttc tatagatctt gttataaggt tttgattcca    3960
catctggtga ttagaagtca ttttgatgag gtgaagtcca ttgctaatca gattcaagag    4020
gactggaaaa gtcttctaac agactgcttt ccaaagattc ttgtaaatat tcttccttat    4080
tttgcctatg agggtaccag agacagtggg atggcacagc aaagagagac tgctaccaag    4140
gtctatgata tgcttaaaag tgaaaactta ttgggaaaac agattgatca cttattcatt    4200
agtaatttac cagagattgt ggtggagtta ttgatgacgt tacatgagcc agcaaattct    4260
agtgccagtc agagcactga cctctgtgac ttttcagggg atttggatcc tgctcctaat    4320
ccacctcatt ttccatcgca tgtgattaaa gcaacatttg cctatatcag caattgtcat    4380
aaaaccaagt taaaaagcat tttagaaatt ctttccaaaa gccctgattc ctatcagaaa    4440
attcttcttg ccatatgtga gcaagcagct gaaacaaata atgtttataa gaagcacaga    4500
attcttaaaa tatatcacct gtttgttagt ttattactga aagatataaa aagtggctta    4560
ggaggagctt gggcctttgt tcttcgagac gttatttata cttttgattca ctatatcaac    4620 caaaggcctt cttgtatcat ggatgtgtca ttacgtagct tctcccttg ttgtgactta    4680 ttaagtcagg tttgccagac agccgtgact tactgtaagg atgctctaga aaaccatctt    4740
catgttattg ttggtacact tataccccctt gtgtatgagc aggtggaggt tcagaaacag    4800
gtattggact tgttgaaata cttagtgata gataacaagg ataatgaaaa cctctatatc    4860
acgattaagc ttttagatcc ttttcctgac catgttgttt ttaaggattt gcgtattact    4920
cagcaaaaaa tcaaatacag tagaggaccc tttttcactct tggaggaaat taaccatttt    4980
ctctcagtaa gtgtttatga tgcacttcca ttgacaagac ttgaaggact aaaggatctt    5040
cgaagacaac tggaactaca taaagatcag atggtggaca ttatgagagc ttctcaggat    5100
aatccgcaag atgggattat ggtgaaacta gttgtcaatt tgttgcagtt atccaagatg    5160
gcaataaacc acactggtga aaaagaagtt ctagaggctg ttggaagctg cttgggagaa    5220
gtgggtccta tagatttctc taccatagct atacaacata gtaaagatgc atcttatacc    5280
aaggccctta agttatttga agataaagaa cttcagtgga ccttcataat gctgacctac    5340
```

```
ctgaataaca cactggtaga agattgtgtc aaagttcgat cagcagctgt tacctgtttg   5400
aaaaacattt tagccacaaa gactggacat agtttctggg agatttataa gatgacaaca   5460
gatccaatgc tggcctatct acagccttt  agaacatcaa gaaaaagtt  tttagaagta   5520
cccagatttg acaaagaaaa cccttttgaa ggcctggatg atataaatct gtggattcct   5580
ctaagtgaaa atcatgacat ttggataaag acactgactt gtgctttttt ggacagtgga   5640
ggcacaaaat gtgaaattct tcaattatta aagccaatgt gtgaagtgaa aactgacttt   5700
tgtcagactg tacttccata cttgattcat gatattttac tccaagatac aaatgaatca   5760
tggagaaatc tgctttctac acatgttcag ggatttttca ccagctgtct tcgacacttc   5820
tcgcaaacga gccgatccac aaccccctgca aacttggatt cagagtcaga gcactttttc   5880
cgatgctgtt tggataaaaa atcacaaaga acaatgcttg ctgttgtgga ctacatgaga   5940
agacaaaaga gaccttcttc aggaacaatt tttaatgatg ctttctggct ggatttaaat   6000
tatctagaag ttgccaaggt agctcagtct tgtgctgctc actttacagc tttactctat   6060
gcagaaatct atgcagataa gaaaagtatg gatgatcaag agaaaagaag tcttgcattt   6120
gaagaaggaa gccagagtac aactatttct agcttgagtg aaaaaagtaa agaagaaact   6180
ggaataagtt tacaggatct tctcttagaa atctacagaa gtataggga gccagatagt    6240
ttgtatggct gtggtggagg gaagatgtta caacccatta ctagactacg aacatatgaa   6300
cacgaagcaa tgtggggcaa agccctagta acatatgacc tcgaaacagc aatcccctca   6360
tcaacacgcc aggcaggaat cattcaggcc ttgcagaatt tgggactctg ccatattctt   6420
tccgtctatt taaaggatt  ggattatgaa aataaagact ggtgtcctga actagaagaa   6480
cttcattacc aagcagcatg gaggaatatg cagtgggacc attgcacttc cgtcagcaaa   6540
gaagtagaag gaaccagtta ccatgaatca ttgtacaatg ctctacaatc tctaagagac   6600
agagaattct ctacatttta tgaaagtctc aaatatgcca gagtaaaaga gtggaagag    6660
atgtgtaagc gcagccttga gtctgtgtat tcgctctatc ccacacttag caggttgcag   6720
gccattggag agctggaaag cattggggag cttttctcaa gatcagtcac acatagacaa   6780
ctctctgaag tatatattaa gtggcagaaa cactcccagc ttctcaagga cagtgatttt   6840
agttttcagg agcctatcat ggctctacgc acagtcattt tggagatcct gatgaaaag    6900
gaaatggaca actcacaaag agaatgtatt aaggacattc tcaccaaaca ccttgtagaa   6960
ctctctatac tggccagaac tttcaagaac actcagctcc ctgaaagggc aatatttcaa   7020
attaaacagt acaattcagt tagctgtgga gtctctgagt ggcagctgga agaagcacaa   7080
gtattctggg caaaaaagga gcagagtctt gccctgagta ttctcaagca aatgatcaag   7140
aagttggatg ccagctgtgc agcgaacaat cccagcctaa aacttacata cacagaatgt   7200
ctgagggttt gtggcaactg gttagcagaa acgtgcttag aaaatcctgc ggtcatcatg   7260
cagacctatc tagaaaaggc agtagaagtt gctggaaatt atgatggaga aagtagtgat   7320
gagctaagaa atgaaaaaat gaaggcattt ctctcattag cccggttttc agatactcaa   7380
taccaaagaa ttgaaaacta catgaaatca tcggaatttg aaaacaagca agctctcctg   7440
aaaagagcca aagaggaagt aggtctcctt agggaacata aaattcagac aaacagatac   7500
acagtaaagg ttcagcgaga gctggagttg gatgaattag ccctgcgtgc actgaaagag   7560
gatcgtaaac gcttcttatg taagcagttg gaaaattata tcaactgctt attaagtgga   7620
gaagaacatg atatgtgggt attccggctt tgttccctct ggcttgaaaa ttctggagtt   7680
```

-continued

```
tctgaagtca atggcatgat gaagagagac ggaatgaaga ttccaacata taaattttg    7740 cctcttatgt accaattggc tgctagaatg gggaccaaga tgatgggagg cctaggattt    7800
catgaagtcc tcaataatct aatctctaga atttcaatgg atcaccccca tcacactttg    7860
tttattatac tggccttagc aaatgcaaac agagatgaat ttctgactaa accagaggta    7920
gccagaagaa gcagaataac taaaaatgtg cctaaacaaa gctctcagct tgatgaggat    7980
cgaacagagg ctgcaaatag aataatatgt actatcagaa gtaggagacc tcagatggtc    8040
agaagtgttg aggcactttg tgatgcttat attatattag caaacttaga tgccactcag    8100
tggaagactc agagaaaagg cataaatatt ccagcagacc agccaattac taaacttaag    8160
aatttagaag atgttgttgt ccctactatg gaaattaagg tggaccacac aggagaatat    8220
ggaaatctgg tgactataca gtcatttaaa gcagaatttc gcttagcagg aggtgtaaat    8280
ttaccaaaaa taatagattg tgtaggttcc gatggcaagg agaggagaca gcttgttaag    8340
ggccgtgatg acctgagaca agatgctgtc atgcaacagg tcttccagat gtgtaataca    8400
ttactgcaga gaaacacgga aactaggaag aggaaattaa ctatctgtac ttataaggtg    8460
gttcccctct ctcagcgaag tggtgttctt gaatggtgca caggaactgt ccccattggt    8520
gaatttcttg ttaacaatga agatggtgct cataaaagat acaggccaaa tgatttcagt    8580
gcctttcagt gccaaaagaa aatgatggag gtgcaaaaaa agtcttttga agagaaatat    8640
gaagtcttca tggatgtttg ccaaaatttt caaccagttt tccgttactt ctgcatggaa    8700
aaattcttgg atccagctat ttggtttgag aagcgattgg cttatacgcg cagtgtagct    8760
acttcttcta ttgttggtta catacttgga cttggtgata gacatgtaca gaatatcttg    8820
ataaatgagc agtcagcaga acttgtacat atagatctag gtgttgcttt tgaacagggc    8880
aaaatccttc ctactcctga gacagttcct tttagactca ccagagatat tgtggatggc    8940
atgggcatta cgggtgttga aggtgtcttc agaagatgct gtgagaaaac catggaagtg    9000
atgagaaact ctcaggaaac tctgttaacc attgtagagg tccttctata tgatccactc    9060
tttgactgga ccatgaatcc tttgaaagct ttgtatttac agcagaggcc ggaagatgaa    9120
actgagcttc accctactct gaatgcagat gaccaagaat gcaaacgaaa tctcagtgat    9180
attgaccaga gtttcgacaa agtagctgaa cgtgtcttaa tgagactaca agagaaactg    9240
aaaggagtgg aagaaggcac tgtgctcagt gttggtggac aggtgaattt gctcatacag    9300
caggccatag accccaaaaa tctcagccga ctttccccag gatggaaagc ttgggtgtga    9360
tcttcagtat atgaattacc ctttc                                         9385
```

<210> SEQ ID NO 3
<211> LENGTH: 393
<212> TYPE: PRT
<213> ORGANISM: Homo sapiens

<400> SEQUENCE: 3

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Thr Pro

```
                65                  70                  75                  80
Thr Pro Ala Ala Pro Ala Pro Ala Pro Ser Trp Pro Leu Ser Ser Ser
                        85                  90                  95
Val Pro Ser Gln Lys Thr Tyr Gln Gly Ser Tyr Gly Phe Arg Leu Gly
                100                 105                 110
Phe Leu His Ser Gly Thr Ala Lys Ser Val Thr Cys Thr Tyr Ser Pro
            115                 120                 125
Ala Leu Asn Lys Met Phe Cys Gln Leu Ala Lys Thr Cys Pro Val Gln
        130                 135                 140
Leu Trp Val Asp Ser Thr Pro Pro Gly Thr Arg Val Arg Ala Met
145                 150                 155                 160
Ala Ile Tyr Lys Gln Ser Gln His Met Thr Glu Val Val Arg Cys
                165                 170                 175
Pro His His Glu Arg Cys Ser Asp Ser Asp Gly Leu Ala Pro Pro Gln
                    180                 185                 190
His Leu Ile Arg Val Glu Gly Asn Leu Arg Val Glu Tyr Leu Asp Asp
                195                 200                 205
Arg Asn Thr Phe Arg His Ser Val Val Val Pro Tyr Glu Pro Pro Glu
    210                 215                 220
Val Gly Ser Asp Cys Thr Thr Ile His Tyr Asn Tyr Met Cys Asn Ser
225                 230                 235                 240
Ser Cys Met Gly Gly Met Asn Arg Arg Pro Ile Leu Thr Ile Ile Thr
                    245                 250                 255
Leu Glu Asp Ser Ser Gly Asn Leu Leu Gly Arg Asn Ser Phe Glu Val
                260                 265                 270
Arg Val Cys Ala Cys Pro Gly Arg Asp Arg Arg Thr Glu Glu Glu Asn
            275                 280                 285
Leu Arg Lys Lys Gly Glu Pro His His Glu Leu Pro Pro Gly Ser Thr
        290                 295                 300
Lys Arg Ala Leu Pro Asn Asn Thr Ser Ser Ser Pro Gln Pro Lys Lys
305                 310                 315                 320
Lys Pro Leu Asp Gly Glu Tyr Phe Thr Leu Gln Ile Arg Gly Arg Glu
                325                 330                 335
Arg Phe Glu Met Phe Arg Glu Leu Asn Glu Ala Leu Glu Leu Lys Asp
                340                 345                 350
Ala Gln Ala Gly Lys Glu Pro Gly Gly Ser Arg Ala His Ser Ser His
            355                 360                 365
Leu Lys Ser Lys Lys Gly Gln Ser Thr Ser Arg His Lys Lys Leu Met
        370                 375                 380
Phe Lys Thr Glu Gly Pro Asp Ser Asp
385                 390

<210> SEQ ID NO 4
<211> LENGTH: 1303
<212> TYPE: DNA
<213> ORGANISM: Homo sapiens

<400> SEQUENCE: 4
gtccaggagc aggtagctgc tgggctccgg ggacactttg cgttcgggct gggagcgtgc        60
tttccacgac ggtgacacgc ttccctggat tggcagccag actgccttcc gggtcactgc       120
catggaggag ccgcagtcag atcctagcgt cgagccccct ctgagtcagg aaacattttc       180
agacctatgg aaactacttc ctgaaaacaa cgttctgtcc cccttgccgt cccaagcaat       240
ggatgatttg atgctgtccc cggacgatat tgaacaatgg ttcactgaag acccaggtcc       300
```

```
agatgaagct cccagaatgc cagaggctgc tcccccgtg gcccctgcac cagcgactcc    360
tacaccggcg gccctgcac cagcccctc ctggcccctg tcatcttctg tcccttccca    420
gaaaacctac cagggcagct acggtttccg tctgggcttc ttgcattctg ggacagccaa    480
gtctgtgact tgcacgtact cccctgccct caacaagatg ttttgccaac tggccaagac    540
ctgccctgtg cagctgtggg ttgattccac accccgccc ggcacccgcg tccgcgccat    600
ggccatctac aagcagtcac agcacatgac ggaggttgtg aggcgctgcc cccaccatga    660
gcgctgctca gatagcgatg gtctggcccc tcctcagcat cttatccgag tggaaggaaa    720
tttgcgtgtg gagtatttgg atgacagaaa acttttcga catagtgtgg tggtgcccta    780
tgagccgcct gaggttggct ctgactgtac caccatccac tacaactaca tgtgtaacag    840
ttcctgcatg ggcggcatga accggaggcc catcctcacc atcatcacac tggaagactc    900
cagtggtaat ctactgggac ggaacagctt tgaggtgcgt gtttgtgcct gtcctgggag    960
agaccggcgc acagaggaag agaatctccg caagaaaggg gagcctcacc acgagctgcc   1020
cccagggagc actaagcgag cactgcccaa caacaccagc tcctctcccc agccaaagaa   1080
gaaaccactg gatggagaat atttcaccct tcagatccgt gggcgtgagc gcttcgagat   1140
gttccgagag ctgaatgagg ccttggaact caaggatgcc caggctggga aggagccagg   1200
ggggagcagg gctcactcca gccacctgaa gtccaaaaag ggtcagtcta cctcccgcca   1260
taaaaaactc atgttcaaga cagaagggcc tgactcagac tga                     1303
```

<210> SEQ ID NO 5
<211> LENGTH: 2644
<212> TYPE: PRT
<213> ORGANISM: Homo sapiens

<400> SEQUENCE: 5

```
Met Gly Glu His Gly Leu Glu Leu Ala Ser Met Ile Pro Ala Leu Arg
 1               5                  10                  15

Glu Leu Gly Ser Ala Thr Pro Glu Glu Tyr Asn Thr Val Val Gln Lys
             20                  25                  30

Pro Arg Gln Ile Leu Cys Gln Phe Ile Asp Arg Ile Leu Thr Asp Val
         35                  40                  45

Asn Val Val Ala Val Glu Leu Val Lys Lys Thr Asp Ser Gln Pro Thr
     50                  55                  60

Ser Val Met Leu Leu Asp Phe Ile Gln His Ile Met Lys Ser Ser Pro
 65                  70                  75                  80

Leu Met Phe Val Asn Val Ser Gly Ser His Glu Ala Lys Gly Ser Cys
                 85                  90                  95

Ile Glu Phe Ser Asn Trp Ile Ile Thr Arg Leu Leu Arg Ile Ala Ala
            100                 105                 110

Thr Pro Ser Cys His Leu Leu His Lys Lys Ile Cys Glu Val Ile Cys
        115                 120                 125

Ser Leu Leu Phe Leu Phe Lys Ser Lys Ser Pro Ala Ile Phe Gly Val
    130                 135                 140

Leu Thr Lys Glu Leu Leu Gln Leu Phe Glu Asp Leu Val Tyr Leu His
145                 150                 155                 160

Arg Arg Asn Val Met Gly His Ala Val Glu Trp Pro Val Val Met Ser
                165                 170                 175

Arg Phe Leu Ser Gln Leu Asp Glu His Met Gly Tyr Leu Gln Ser Ala
            180                 185                 190
```

-continued

```
Pro Leu Gln Leu Met Ser Met Gln Asn Leu Glu Phe Ile Glu Val Thr
        195                 200                 205
Leu Leu Met Val Leu Thr Arg Ile Ile Ala Ile Val Phe Phe Arg Arg
210                 215                 220
Gln Glu Leu Leu Leu Trp Gln Ile Gly Cys Val Leu Leu Glu Tyr Gly
225                 230                 235                 240
Ser Pro Lys Ile Lys Ser Leu Ala Ile Ser Phe Leu Thr Glu Leu Phe
                245                 250                 255
Gln Leu Gly Gly Leu Pro Ala Gln Pro Ala Ser Thr Phe Phe Ser Ser
                260                 265                 270
Phe Leu Glu Leu Leu Lys His Leu Val Glu Met Asp Thr Asp Gln Leu
                275                 280                 285
Lys Leu Tyr Glu Glu Pro Leu Ser Lys Leu Ile Lys Thr Leu Phe Pro
290                 295                 300
Phe Glu Ala Glu Ala Tyr Arg Asn Ile Glu Pro Val Tyr Leu Asn Met
305                 310                 315                 320
Leu Leu Glu Lys Leu Cys Val Met Phe Glu Asp Gly Val Leu Met Arg
                325                 330                 335
Leu Lys Ser Asp Leu Leu Lys Ala Ala Leu Cys His Leu Leu Gln Tyr
                340                 345                 350
Phe Leu Lys Phe Val Pro Ala Gly Tyr Glu Ser Ala Leu Gln Val Arg
                355                 360                 365
Lys Val Tyr Val Arg Asn Ile Cys Lys Ala Leu Leu Asp Val Leu Gly
                370                 375                 380
Ile Glu Val Asp Ala Glu Tyr Leu Leu Gly Pro Leu Tyr Ala Ala Leu
385                 390                 395                 400
Lys Met Glu Ser Met Glu Ile Ile Glu Glu Ile Gln Cys Gln Thr Gln
                405                 410                 415
Gln Glu Asn Leu Ser Ser Asn Ser Asp Gly Ile Ser Pro Lys Arg Arg
                420                 425                 430
Arg Leu Ser Ser Ser Leu Asn Pro Ser Lys Arg Ala Pro Lys Gln Thr
                435                 440                 445
Glu Glu Ile Lys His Val Asp Met Asn Gln Lys Ser Ile Leu Trp Ser
450                 455                 460
Ala Leu Lys Gln Lys Ala Glu Ser Leu Gln Ile Ser Leu Glu Tyr Ser
465                 470                 475                 480
Gly Leu Lys Asn Pro Val Ile Glu Met Leu Glu Gly Ile Ala Val Val
                485                 490                 495
Leu Gln Leu Thr Ala Leu Cys Thr Val His Cys Ser His Gln Asn Met
                500                 505                 510
Asn Cys Arg Thr Phe Lys Asp Cys Gln His Lys Ser Lys Lys Pro
                515                 520                 525
Ser Val Val Ile Thr Trp Met Ser Leu Asp Phe Tyr Thr Lys Val Leu
530                 535                 540
Lys Ser Cys Arg Ser Leu Leu Glu Ser Val Gln Lys Leu Asp Leu Glu
545                 550                 555                 560
Ala Thr Ile Asp Lys Val Val Lys Ile Tyr Asp Ala Leu Ile Tyr Met
                565                 570                 575
Gln Val Asn Ser Ser Phe Glu Asp His Ile Leu Glu Asp Leu Cys Gly
                580                 585                 590
Met Leu Ser Leu Pro Trp Ile Tyr Ser His Ser Asp Asp Gly Cys Leu
                595                 600                 605
Lys Leu Thr Thr Phe Ala Ala Asn Leu Leu Thr Leu Ser Cys Arg Ile
```

-continued

```
            610                 615                 620
Ser Asp Ser Tyr Ser Pro Gln Ala Gln Ser Arg Cys Val Phe Leu Leu
625                 630                 635                 640

Thr Leu Phe Pro Arg Arg Ile Phe Leu Glu Trp Arg Thr Ala Val Tyr
                    645                 650                 655

Asn Trp Ala Leu Gln Ser Ser His Glu Val Ile Arg Ala Ser Cys Val
                660                 665                 670

Ser Gly Phe Phe Ile Leu Leu Gln Gln Gln Asn Ser Cys Asn Arg Val
            675                 680                 685

Pro Lys Ile Leu Ile Asp Lys Val Lys Asp Ser Asp Ile Val Lys
690                 695                 700

Lys Glu Phe Ala Ser Ile Leu Gly Gln Leu Val Cys Thr Leu His Gly
705                 710                 715                 720

Met Phe Tyr Leu Thr Ser Ser Leu Thr Glu Pro Phe Ser Glu His Gly
                    725                 730                 735

His Val Asp Leu Phe Cys Arg Asn Leu Lys Ala Thr Ser Gln His Glu
                740                 745                 750

Cys Ser Ser Ser Gln Leu Lys Ala Ser Val Cys Lys Pro Phe Leu Phe
            755                 760                 765

Leu Leu Lys Lys Lys Ile Pro Ser Pro Val Lys Leu Ala Phe Ile Asp
770                 775                 780

Asn Leu His His Leu Cys Lys His Leu Asp Phe Arg Glu Asp Glu Thr
785                 790                 795                 800

Asp Val Lys Ala Val Leu Gly Thr Leu Leu Asn Leu Met Glu Asp Pro
                    805                 810                 815

Asp Lys Asp Val Arg Val Ala Phe Ser Gly Asn Ile Lys His Ile Leu
                820                 825                 830

Glu Ser Leu Asp Ser Glu Asp Gly Phe Ile Lys Glu Leu Phe Val Leu
            835                 840                 845

Arg Met Lys Glu Ala Tyr Thr His Ala Gln Ile Ser Arg Asn Asn Glu
850                 855                 860

Leu Lys Asp Thr Leu Ile Leu Thr Thr Gly Asp Ile Gly Arg Ala Ala
865                 870                 875                 880

Lys Gly Asp Leu Val Pro Phe Ala Leu Leu His Leu His Cys Leu
                    885                 890                 895

Leu Ser Lys Ser Ala Ser Val Ser Gly Ala Ala Tyr Thr Glu Ile Arg
                900                 905                 910

Ala Leu Val Ala Ala Lys Ser Val Lys Leu Gln Ser Phe Phe Ser Gln
            915                 920                 925

Tyr Lys Lys Pro Ile Cys Gln Phe Leu Val Glu Ser Leu His Ser Ser
930                 935                 940

Gln Met Thr Ala Leu Pro Asn Thr Pro Cys Gln Asn Ala Asp Val Arg
945                 950                 955                 960

Lys Gln Asp Val Ala His Gln Arg Glu Met Ala Leu Asn Thr Leu Ser
                    965                 970                 975

Glu Ile Ala Asn Val Phe Asp Phe Pro Asp Leu Asn Arg Phe Leu Thr
                980                 985                 990

Arg Thr Leu Gln Val Leu Leu Pro Asp Leu Ala Lys Ala Ser Pro
            995                 1000                1005

Ala Ala Ser Ala Leu Ile Arg Thr Leu Gly Lys Gln Leu Asn Val Asn
    1010                1015                1020

Arg Arg Glu Ile Leu Ile Asn Asn Phe Lys Tyr Ile Phe Ser His Leu
1025                1030                1035                1040
```

-continued

```
Val Cys Ser Cys Ser Lys Asp Glu Leu Glu Arg Ala Leu His Tyr Leu
            1045                1050                1055

Lys Asn Glu Thr Glu Ile Glu Leu Gly Ser Leu Leu Arg Gln Asp Phe
        1060                1065                1070

Gln Gly Leu His Asn Glu Leu Leu Leu Arg Ile Gly Glu His Tyr Gln
    1075                1080                1085

Gln Val Phe Asn Gly Leu Ser Ile Leu Ala Ser Phe Ala Ser Ser Asp
1090                1095                1100

Asp Pro Tyr Gln Gly Pro Arg Asp Ile Ile Ser Pro Glu Leu Met Ala
1105                1110                1115                1120

Asp Tyr Leu Gln Pro Lys Leu Leu Gly Ile Leu Ala Phe Phe Asn Met
            1125                1130                1135

Gln Leu Leu Ser Ser Ser Val Gly Ile Glu Asp Lys Lys Met Ala Leu
        1140                1145                1150

Asn Ser Leu Met Ser Leu Met Lys Leu Met Gly Pro Lys His Val Ser
    1155                1160                1165

Ser Val Arg Val Lys Met Met Thr Thr Leu Arg Thr Gly Leu Arg Phe
1170                1175                1180

Lys Asp Asp Phe Pro Glu Leu Cys Cys Arg Ala Trp Asp Cys Phe Val
1185                1190                1195                1200

Arg Cys Leu Asp His Ala Cys Leu Gly Ser Leu Leu Ser His Val Ile
            1205                1210                1215

Val Ala Leu Leu Pro Leu Ile His Ile Gln Pro Lys Glu Thr Ala Ala
        1220                1225                1230

Ile Phe His Tyr Leu Ile Ile Glu Asn Arg Asp Ala Val Gln Asp Phe
    1235                1240                1245

Leu His Glu Ile Tyr Phe Leu Pro Asp His Pro Glu Leu Lys Lys Ile
1250                1255                1260

Lys Ala Val Leu Gln Glu Tyr Arg Lys Glu Thr Ser Glu Ser Thr Asp
1265                1270                1275                1280

Leu Gln Thr Thr Leu Gln Leu Ser Met Lys Ala Ile Gln His Glu Asn
            1285                1290                1295

Val Asp Val Arg Ile His Ala Leu Thr Ser Leu Lys Glu Thr Leu Tyr
        1300                1305                1310

Lys Asn Gln Glu Lys Leu Ile Lys Tyr Ala Thr Asp Ser Glu Thr Val
    1315                1320                1325

Glu Pro Ile Ile Ser Gln Leu Val Thr Val Leu Leu Lys Gly Cys Gln
1330                1335                1340

Asp Ala Asn Ser Gln Ala Arg Leu Leu Cys Gly Glu Cys Leu Gly Glu
1345                1350                1355                1360

Leu Gly Ala Ile Asp Pro Gly Arg Leu Asp Phe Ser Thr Thr Glu Thr
            1365                1370                1375

Gln Gly Lys Asp Phe Thr Phe Val Thr Gly Val Glu Asp Ser Ser Phe
        1380                1385                1390

Ala Tyr Gly Leu Leu Met Glu Leu Thr Arg Ala Tyr Leu Ala Tyr Ala
    1395                1400                1405

Asp Asn Ser Arg Ala Gln Asp Ser Ala Ala Tyr Ala Ile Gln Glu Leu
    1410                1415                1420

Leu Ser Ile Tyr Asp Cys Arg Glu Met Glu Thr Asn Gly Pro Gly His
1425                1430                1435                1440

Gln Leu Trp Arg Arg Phe Pro Glu His Val Arg Glu Ile Leu Glu Pro
            1445                1450                1455
```

-continued

His Leu Asn Thr Arg Tyr Lys Ser Ser Gln Lys Ser Thr Asp Trp Ser
                1460                1465                1470

Gly Val Lys Lys Pro Ile Tyr Leu Ser Lys Leu Gly Ser Asn Phe Ala
            1475                1480                1485

Glu Trp Ser Ala Ser Trp Ala Gly Tyr Leu Ile Thr Lys Val Arg His
        1490                1495                1500

Asp Leu Ala Ser Lys Ile Phe Thr Cys Ser Ile Met Met Lys His
    1505                1510                1515                1520

Asp Phe Lys Val Thr Ile Tyr Leu Leu Pro His Ile Leu Val Tyr Val
                1525                1530                1535

Leu Leu Gly Cys Asn Gln Glu Asp Gln Glu Val Tyr Ala Glu Ile
            1540                1545                1550

Met Ala Val Leu Lys His Asp Asp Gln His Thr Ile Asn Thr Gln Asp
        1555                1560                1565

Ile Ala Ser Asp Leu Cys Gln Leu Ser Thr Gln Thr Val Phe Ser Met
    1570                1575                1580

Leu Asp His Leu Thr Gln Trp Ala Arg His Lys Phe Gln Ala Leu Lys
1585                1590                1595                1600

Ala Glu Lys Cys Pro His Ser Lys Ser Asn Arg Asn Lys Val Asp Ser
            1605                1610                1615

Met Val Ser Thr Val Asp Tyr Glu Asp Tyr Gln Ser Val Thr Arg Phe
        1620                1625                1630

Leu Asp Leu Ile Pro Gln Asp Thr Leu Ala Val Ala Ser Phe Arg Ser
    1635                1640                1645

Lys Ala Tyr Thr Arg Ala Val Met His Phe Glu Ser Phe Ile Thr Glu
    1650                1655                1660

Lys Lys Gln Asn Ile Gln Glu His Leu Gly Phe Leu Gln Lys Leu Tyr
1665                1670                1675                1680

Ala Ala Met His Glu Pro Asp Gly Val Ala Gly Val Ser Ala Ile Arg
            1685                1690                1695

Lys Ala Glu Pro Ser Leu Lys Glu Gln Ile Leu Glu His Glu Ser Leu
        1700                1705                1710

Gly Leu Leu Arg Asp Ala Thr Ala Cys Tyr Asp Arg Ala Ile Gln Leu
    1715                1720                1725

Glu Pro Asp Gln Ile Ile His Tyr His Gly Val Val Lys Ser Met Leu
    1730                1735                1740

Gly Leu Gly Gln Leu Ser Thr Val Ile Thr Gln Val Asn Gly Val His
1745                1750                1755                1760

Ala Asn Arg Ser Glu Trp Thr Asp Glu Leu Asn Thr Tyr Arg Val Glu
            1765                1770                1775

Ala Ala Trp Lys Leu Ser Gln Trp Asp Leu Val Glu Asn Tyr Leu Ala
        1780                1785                1790

Ala Asp Gly Lys Ser Thr Thr Trp Ser Val Arg Leu Gly Gln Leu Leu
    1795                1800                1805

Leu Ser Ala Lys Lys Arg Asp Ile Thr Ala Phe Tyr Asp Ser Leu Lys
1810                1815                1820

Leu Val Arg Ala Glu Gln Ile Val Pro Leu Ser Ala Ala Ser Phe Glu
            1825                1830                1835                1840

Arg Gly Ser Tyr Gln Arg Gly Tyr Glu Tyr Ile Val Arg Leu His Met
        1845                1850                1855

Leu Cys Glu Leu Glu His Ser Ile Lys Pro Leu Phe Gln His Ser Pro
    1860                1865                1870

Gly Asp Ser Ser Gln Glu Asp Ser Leu Asn Trp Val Ala Arg Leu Glu

-continued

```
            1875                1880                1885
Met Thr Gln Asn Ser Tyr Arg Ala Lys Glu Pro Ile Leu Ala Leu Arg
    1890                1895                1900
Arg Ala Leu Leu Ser Leu Asn Lys Arg Pro Asp Tyr Asn Glu Met Val
1905                1910                1915                1920
Gly Glu Cys Trp Leu Gln Ser Ala Arg Val Ala Arg Lys Ala Gly His
            1925                1930                1935
His Gln Thr Ala Tyr Asn Ala Leu Leu Asn Ala Gly Glu Ser Arg Leu
        1940                1945                1950
Ala Glu Leu Tyr Val Glu Arg Ala Lys Trp Leu Trp Ser Lys Gly Asp
    1955                1960                1965
Val His Gln Ala Leu Ile Val Leu Gln Lys Gly Val Glu Leu Cys Phe
1970                1975                1980
Pro Glu Asn Glu Thr Pro Pro Glu Gly Lys Asn Met Leu Ile His Gly
1985                1990                1995                2000
Arg Ala Met Leu Leu Val Gly Arg Phe Met Glu Glu Thr Ala Asn Phe
            2005                2010                2015
Glu Ser Asn Ala Ile Met Lys Lys Tyr Lys Asp Val Thr Ala Cys Leu
        2020                2025                2030
Pro Glu Trp Glu Asp Gly His Phe Tyr Leu Ala Lys Tyr Tyr Asp Lys
    2035                2040                2045
Leu Met Pro Met Val Thr Asp Asn Lys Met Glu Lys Gln Gly Asp Leu
2050                2055                2060
Ile Arg Tyr Ile Val Leu His Phe Gly Arg Ser Leu Gln Tyr Gly Asn
2065                2070                2075                2080
Gln Phe Ile Tyr Gln Ser Met Pro Arg Met Leu Thr Leu Trp Leu Asp
        2085                2090                2095
Tyr Gly Thr Lys Ala Tyr Glu Trp Glu Lys Ala Gly Arg Ser Asp Arg
    2100                2105                2110
Val Gln Met Arg Asn Asp Leu Gly Lys Ile Asn Lys Val Ile Thr Glu
        2115                2120                2125
His Thr Asn Tyr Leu Ala Pro Tyr Gln Phe Leu Thr Ala Phe Ser Gln
    2130                2135                2140
Leu Ile Ser Arg Ile Cys His Ser His Asp Glu Val Phe Val Val Leu
2145                2150                2155                2160
Met Glu Ile Ile Ala Lys Val Phe Leu Ala Tyr Pro Gln Gln Ala Met
            2165                2170                2175
Trp Met Met Thr Ala Val Ser Lys Ser Ser Tyr Pro Met Arg Val Asn
            2180                2185                2190
Arg Cys Lys Glu Ile Leu Asn Lys Ala Ile His Met Lys Lys Ser Leu
        2195                2200                2205
Glu Lys Phe Val Gly Asp Ala Thr Arg Leu Thr Asp Lys Leu Leu Glu
    2210                2215                2220
Leu Cys Asn Lys Pro Val Asp Gly Ser Ser Ser Thr Leu Ser Met Ser
2225                2230                2235                2240
Thr His Phe Lys Met Leu Lys Lys Leu Val Glu Glu Ala Thr Phe Ser
            2245                2250                2255
Glu Ile Leu Ile Pro Leu Gln Ser Val Met Ile Pro Thr Leu Pro Ser
        2260                2265                2270
Ile Leu Gly Thr His Ala Asn His Ala Ser His Glu Pro Phe Pro Gly
    2275                2280                2285
His Trp Ala Tyr Ile Ala Gly Phe Asp Asp Met Val Glu Ile Leu Ala
    2290                2295                2300
```

```
Ser Leu Gln Lys Pro Lys Lys Ile Ser Leu Lys Gly Ser Asp Gly Lys
2305                2310                2315                2320

Phe Tyr Ile Met Met Cys Lys Pro Lys Asp Asp Leu Arg Lys Asp Cys
                2325                2330                2335

Arg Leu Met Glu Phe Asn Ser Leu Ile Asn Lys Cys Leu Arg Lys Asp
            2340                2345                2350

Ala Glu Ser Arg Arg Arg Glu Leu His Ile Arg Thr Tyr Ala Val Ile
        2355                2360                2365

Pro Leu Asn Asp Glu Cys Gly Ile Ile Glu Trp Val Asn Asn Thr Ala
    2370                2375                2380

Gly Leu Arg Pro Ile Leu Thr Lys Leu Tyr Lys Glu Lys Gly Val Tyr
2385                2390                2395                2400

Met Thr Gly Lys Glu Leu Arg Gln Cys Met Leu Pro Lys Ser Ala Ala
                2405                2410                2415

Leu Ser Glu Lys Leu Lys Val Phe Arg Glu Phe Leu Leu Pro Arg His
            2420                2425                2430

Pro Pro Ile Phe His Glu Trp Phe Leu Arg Thr Phe Pro Asp Pro Thr
        2435                2440                2445

Ser Trp Tyr Ser Ser Arg Ser Ala Tyr Cys Arg Ser Thr Ala Val Met
    2450                2455                2460

Ser Met Val Gly Tyr Ile Leu Gly Leu Gly Asp Arg His Gly Glu Asn
2465                2470                2475                2480

Ile Leu Phe Asp Ser Leu Thr Gly Glu Cys Val His Val Asp Phe Asn
                2485                2490                2495

Cys Leu Phe Asn Lys Gly Glu Thr Phe Glu Val Pro Glu Ile Val Pro
            2500                2505                2510

Phe Arg Leu Thr His Asn Met Val Asn Gly Met Gly Pro Met Gly Thr
        2515                2520                2525

Glu Gly Leu Phe Arg Arg Ala Cys Glu Val Thr Met Arg Leu Met Arg
2530                2535                2540

Asp Gln Arg Glu Pro Leu Met Ser Val Leu Lys Thr Phe Leu His Asp
2545                2550                2555                2560

Pro Leu Val Glu Trp Ser Lys Pro Val Lys Gly His Ser Lys Ala Pro
            2565                2570                2575

Leu Asn Glu Thr Gly Glu Val Val Asn Glu Lys Ala Lys Thr His Val
        2580                2585                2590

Leu Asp Ile Glu Gln Arg Leu Gln Gly Val Ile Lys Thr Arg Asn Arg
    2595                2600                2605

Val Thr Gly Leu Pro Leu Ser Ile Glu Gly His Val His Tyr Leu Ile
2610                2615                2620

Gln Glu Ala Thr Asp Glu Asn Leu Leu Cys Gln Met Tyr Leu Gly Trp
2625                2630                2635                2640

Thr Pro Tyr Met

<210> SEQ ID NO 6
<211> LENGTH: 8210
<212> TYPE: DNA
<213> ORGANISM: Homo sapiens

<400> SEQUENCE: 6
gcctccacac ggctccgtcg ggcgccgcgc tcttccggca gcggtagctt tggagacgcc    60
gggaacccgc gttggcgtgg ttgactagtg cctcgcagcc tcagcatggg ggaacatggc   120
ctggagctgg cttccatgat ccccgccctg cgggagctgg gcagtgccac accagaggaa   180
```

```
tataatacag ttgtacagaa gccaagacaa attctgtgtc aattcattga ccggatactt   240
acagatgtaa atgttgttgc tgtagaactt gtaaagaaaa ctgactctca gccaacctcc   300
gtgatgttgc ttgatttcat ccagcatatc atgaaatcct ccccacttat gtttgtaaat   360
gtgagtggaa gccatgaggc caaaggcagt tgtattgaat tcagtaattg gatcataacg   420
agacttctgc ggattgcagc aactccctcc tgtcatttgt tacacaagaa aatctgtgaa   480
gtcatctgtt cattattatt tcttttttaaa agcaagagtc ctgctatttt tggggtactc   540
acaaaagaat tattcaaact ttttgaagac ttggtttacc tccatagaag aaatgtgatg   600
ggtcatgctg tggaatggcc agtggtcatg agccgatttt taagtcaatt agatgaacac   660
atgggatatt tacaatcagc tcctttgcag ttgatgagta tgcaaaattt agaatttatt   720
gaagtcactt tattaatggt tcttactcgt attattgcaa ttgtgttttt tagaaggcaa   780
gaactcttac tttggcagat aggttgtgtt ctgctagagt atggtagtcc aaaaattaaa   840
tccctagcaa ttagcttttt aacagaactt tttcagcttg gaggactacc agcacaacca   900
gctagcactt ttttcagctc attttttggaa ttattaaaac accttgtaga aatggatact   960
gaccaattga aactctatga agagccatta tcaaagctga taaagacact atttcccttt  1020
gaagcagaag cttatagaaa tattgaacct gtctatttaa atatgctgct ggaaaaactc  1080
tgtgtcatgt ttgaagacgg tgtgctcatg cggcttaagt ctgatttgct aaaagcagct  1140
ttgtgccatt tactgcagta tttccttaaa tttgtgccag ctgggtatga atctgcttta  1200
caagtcagga aggtctatgt gagaaatatt tgtaaagctc ttttgatgt gcttggaatt  1260
gaggtagatg cagagtactt gttgggccca ctttatgcag cttgaaaat ggaaagtatg  1320
gaaatcattg aggagattca atgccaaact caacaggaaa acctcagcag taatagtgat  1380
ggaatatcac ccaaaaggcg tcgtctcagc tcgtctctaa acccttctaa aagagcacca  1440
aaacagactg aggaaattaa acatgtggac atgaaccaaa agagcatatt atggagtgca  1500
ctgaaacaga agctgaatc ccttcagatt tcccttgaat acagtggcct aaagaatcct  1560
gttattgaga tgttagaagg aattgctgtt gtcttacaac tgactgctct gtgtactgtt  1620
cattgttctc atcaaaacat gaactgccgt actttcaagg actgtcaaca taaatccaag  1680
aagaaacctt ctgtagtgat aacttggatg tcattggatt tttacacaaa agtgcttaag  1740
agctgtagaa gtttgttaga atctgttcag aaactggacc tggaggcaac cattgataag  1800
gtggtgaaaa tttatgatgc tttgatttat atgcaagtaa acagttcatt tgaagatcat  1860
atcctggaag atttatgtgg tatgctctca cttccatgga tttattccca ttctgatgat  1920
ggctgtttaa agttgaccac atttgccgct aatcttctaa cattaagctg taggatttca  1980
gatagctatt caccacaggc acaatcacga tgtgtgtttc ttctgactct gtttccaaga  2040
agaatattcc ttgagtggag aacagcagtt tacaactggg ccctgcagag ctcccatgaa  2100
gtaatccggg ctagttgtgt tagtggattt tttatcttat tgcagcagca gaattcttgt  2160
aacagagttc ccaagattct tatagataaa gtcaaagatg attctgacat tgtcaagaaa  2220
gaatttgctt ctatacttgg tcaacttgtc tgtactcttc acggcatgtt ttatctgaca  2280
agttctttaa cagaaccttt ctctgaacac ggacatgtgg acctcttctg taggaacttg  2340
aaagccactt ctcaacatga atgttcatct tctcaactaa aagcttctgt ctgcaagcca  2400
ttcctttttcc tactgaaaaa aaaaatacct agtccagtaa aacttgcttt catagataat  2460
ctacatcatc tttgtaagca tcttgatttt agagaagatg aaacagatgt aaaagcagtt  2520
```

```
cttggaactt tattaaattt aatggaagat ccagacaaag atgttagagt ggcttttagt    2580
ggaaatatca agcacatatt ggaatccttg gactctgaag atggatttat aaaggagctt    2640
tttgtcttaa gaatgaagga agcatataca catgcccaaa tatcaagaaa taatgagctg    2700
aaggatacct tgattcttac aacagggdat attggaaggg ccgcaaaagg agatttggta    2760
ccatttgcac tcttacactt attgcattgt ttgttatcca agtcagcatc tgtctctgga    2820
gcagcataca cagaaattag agctctggtt gcagctaaaa gtgttaaact gcaaagtttt    2880
ttcagccagt ataagaaacc catctgtcag ttttttggtag aatcccttca ctctagtcag    2940
atgacagcac ttccgaatac tccatgccag aatgctgacg tgcgaaaaca agatgtggct    3000
caccagagag aaatggcttt aaatacgttg tctgaaattg ccaacgtttt cgactttcct    3060
gatcttaatc gttttcttac taggacatta caagttctac tacctgatct tgctgccaaa    3120
gcaagccctg cagcttctgc tctcattcga actttaggaa acaattaaa tgtcaatcgt    3180 agagagattt aataaaacaa cttcaaatat attttttctc atttggtctg ttcttgttcc    3240
aaagatgaat tagaacgtgc ccttcattat ctgaagaatg aaacagaaat tgaactgggg    3300
agcctgttga gacaagattt ccaaggattg cataatgaat tattgctgcg tattggagaa    3360
cactatcaac aggttttaa tggtttgtca atacttgcct catttgcatc cagtgatgat    3420
ccatatcagg gcccgagaga tatcatatca cctgaactga tggctgatta tttacaaccc    3480
aaattgttgg gcattttggc ttttttttaac atgcagttac tgagctctag tgttggcatt    3540
gaagataaga aaatggcctt gaacagtttg atgtctttga tgaagttaat gggacccaaa    3600
catgtcagtt ctgtgagggt gaagatgatg accacactga gaactggcct tcgattcaag    3660
gatgattttc ctgaattgtg ttgcagagct tgggactgct tgttcgctg cctggatcat    3720 gcttgtctgg gctcccttct cagtcatgta atagtagctt tgttacctct tatacacatc    3780
cagcctaaag aaactgcagc tatcttccac tacctcataa ttgaaaacag ggatgctgtg    3840
caagattttc ttcatgaaat atatttttta cctgatcatc cagaattaaa aaagataaaa    3900
gccgttctcc aggaatacag aaaggagacc tctgagagca ctgatcttca gacaactctt    3960
cagctctcta tgaaggccat tcaacatgaa aatgtcgatg ttcgtattca tgctcttaca    4020
agcttgaagg aaaccttgta taaaaatcag gaaaaactga taaagtatgc aacagacagt    4080
gaaacagtag aacctattat ctcacagttg gtgacagtgc ttttgaaagg ttgccaagat    4140
gcaaactctc aagctcggtt gctctgtggg gaatgtttag gggaattggg ggcgatagat    4200
ccaggtcgat tagatttctc aacaactgaa actcaaggaa aagatttac atttgtgact    4260 ggagtagaag attcaagctt tgcctatgga ttattgatgg agctaacaag agcttacctt    4320
gcgtacgctg ataatagccg agctcaagat tcagctgcct atgccattca ggagttgctt    4380
tctatttatg actgtagaga gatggagacc aacggcccag gtcaccaatt gtggaggaga    4440
tttcctgagc atgttcggga aatactagaa cctcatctaa ataccagata caagagttct    4500
cagaagtcaa ccgattggtc tggagtaaag aagccaattt acttaagtaa attgggtagt    4560
aactttgcag aatggtcagc atcttgggca ggttatctta ttacaaaggt tcgacatgat    4620
cttgccagta aaattttcac ctgctgtagc attatgatga agcatgattt caaagtgacc    4680
atctatcttc ttccacatat tctggtgtat gtcttactgg gttgtaatca agaagatcag    4740
caggaggttt atgcagaaat tatggcagtt ctaaagcatg acgatcagca taccataaat    4800
acccaagaca ttgcatctga tctgtgtcaa ctcagtacac agactgtgtt ctccatgctt    4860
gaccatctca cacagtgggc aaggcacaaa tttcaggcac tgaaagctga gaaatgtcca    4920
```

-continued

```
cacagcaaat caaacagaaa taaggtagac tcaatggtat ctactgtgga ttatgaagac   4980
tatcagagtg taacccgttt tctagacctc ataccccagg atactctggc agtagcttcc   5040
tttcgctcca aagcatacac acgagctgta atgcactttg aatcatttat tacagaaaag   5100
aagcaaaata ttcaggaaca tcttggattt ttacagaaat tgtatgctgc tatgcatgaa   5160
cctgatggag tggccggagt cagtgcaatt agaaaggcag aaccatctct aaaagaacag   5220
atccttgaac atgaaagcct tggcttgctg agggatgcca ctgcttgtta tgacagggct   5280
attcagctag aaccagacca gatcattcat tatcatggtg tagtaaagtc catgttaggt   5340
cttggtcagc tgtctactgt tatcactcag gtgaatggag tgcatgctaa caggtccgag   5400
tggacagatg aattaaacac gtacagagtg aagcagcttg gaaattgtc acagtgggat   5460 ttggtggaaa actatttggc agcagatgga aaatctacaa catggagtgt cagactggga   5520
cagctattat tatcagccaa aaaaagagat atcacagctt tttatgactc actgaaacta   5580
gtgagagcag aacaaattgt acctctttca gctgcaagct ttgaaagagg ctcctaccaa   5640
cgaggatatg aatatattgt gagattgcac atgttatgtg agttggagca tagcatcaaa   5700
ccacttttcc agcattctcc aggtgacagt tctcaagaag attctctaaa ctgggtagct   5760
cgactagaaa tgacccagaa ttcctacaga gccaaggagc ctatcctggc tctccggagg   5820
gctttactaa gcctcaacaa aagaccagat tacaatgaaa tggttggaga atgctggctg   5880
cagagtgcca gggtagctag aaaggctggt caccaccaga cagcctacaa tgctctcctt   5940
aatgcagggg aatcacgact cgctgaactg tacgtgaaaa gggcaaagtg gctctggtcc   6000
aagggtgatg ttcaccaggc actaattgtt cttcaaaaag gtgttgaatt atgttttcct   6060
gaaaatgaaa ccccacctga gggtaagaac atgttaatcc atggtcgagc tatgctacta   6120
gtgggccgat ttatggaaga aacagctaac tttgaaagca atgcaattat gaaaaaatat   6180
aaggatgtga ccgcgtgcct gccagaatgg gaggatgggc attttttacct tgccaagtac   6240 tatgacaaat tgatgcccat ggtcacagac aacaaaatgg aaaagcaagg tgatctcatc   6300
cggtatatag ttcttcattt tggcagatct ctacaatatg gaaatcagtt catatatcag   6360
tcaatgccac gaatgttaac tctatggctt gattatggta caaaggcata tgaatgggaa   6420
aaagctggcc gctccgatcg tgtacaaatg aggaatgatt tgggtaaaat aaacaaggtt   6480
atcacagagc atacaaacta tttagctcca tatcaatttt tgactgcttt ttcacaattg   6540
atctctcgaa tttgtcattc tcacgatgaa gtttttgttg tcttgatgga ataatagcc   6600 aaagtatttc tagcctatcc tcaacaagca atgtggatga tgacagctgt gtcaaagtca   6660
tcttatccca tgcgtgtgaa cagatgcaag gaaatcctca ataaagctat tcatatgaaa   6720
aaatccttag agaagtttgt tggagatgca actcgcctaa cagataagct tctagaattg   6780
tgcaataaac cggttgatgg aagtagttcc acattaagca tgagcactca ttttaaaatg   6840
cttaaaaagc tggtagaaga agcaacattt agtgaaatcc tcattcctct acaatcagtc   6900
atgataccta cacttccatc aattctgggt acccatgcta accatgctag ccatgaacca   6960
tttcctggac attgggccta tattgcaggg tttgatgata tggtggaaat tcttgcttct   7020
cttcagaaac caaagaagat ttcttttaaa ggctcagatg gaaagttcta catcatgatg   7080
tgtaagccaa aagatgacct gagaaaggat tgtagactaa tggaattcaa ttccttgatt   7140
aataagtgct taagaaaaga tgcagagtct cgtagaagag aacttcatat tcgaacatat   7200
gcagttattc cactaaatga tgaatgtggg attattgaat gggtgaacaa cactgctggt   7260
```

-continued

```
ttgagaccta ttctgaccaa actatataaa gaaaagggag tgtatatgac aggaaaagaa    7320
cttcgccagt gtatgctacc aaagtcagca gctttatctg aaaaactcaa agtattccga    7380
gaatttctcc tgcccaggca tcctcctatt tttcatgagt ggtttctgag aacattccct    7440
gatcctacat catggtacag tagtagatca gcttactgcc gttccactgc agtaatgtca    7500
atggttggtt atattctggg gcttggagac cgtcatggtg aaaatattct ctttgattct    7560
ttgactggtg aatgcgtaca tgtagatttc aattgtcttt tcaataaggg agaaaccttt    7620
gaagttccag aaattgtgcc atttcgcctg actcataata tggttaatgg aatgggtcct    7680
atgggaacag agggtctttt tcgaagagca tgtgaagtta caatgaggct gatgcgtgat    7740
cagcgagagc ctttaatgag tgtcttaaag acttttctac atgatcctct tgtggaatgg    7800
agtaaaccag tgaaagggca ttccaaagcg ccactgaatg aaactggaga agttgtcaat    7860
gaaaaggcca agaccatgt tcttgacatt gagcagcgac tacaaggtgt aatcaagact    7920
cgaaatagag tgacaggact gccgttatct attgaaggac atgtgcatta ccttatacag    7980
gaagctactg atgaaaactt actatgccag atgtatcttg gttggactcc atatatgtga    8040
aatgaaatta tgtaaaagaa tatgttaata atctaaaagt aatgcatttg gtatgaatct    8100
gtggttgtat ctgttcaatt ctaaagtaca acataaattt acgttctcag caactgttat    8160
ttctctctga tcattaatta tatgtaaaat aatatacatt cactcgtgcc                8210
```

<210> SEQ ID NO 7
<211> LENGTH: 4096
<212> TYPE: PRT
<213> ORGANISM: Homo sapiens
<220> FEATURE:
<221> NAME/KEY: SITE
<222> LOCATION: (3316)
<223> OTHER INFORMATION: Xaa is uncertain

<400> SEQUENCE: 7

```
Met Ala Gly Ser Gly Ala Gly Val Arg Cys Ser Leu Leu Arg Leu Gln
  1               5                  10                  15

Glu Thr Leu Ser Ala Ala Asp Arg Cys Gly Ala Ala Leu Ala Gly His
             20                  25                  30

Gln Leu Ile Arg Gly Leu Gly Gln Glu Cys Val Leu Ser Ser Ser Pro
         35                  40                  45

Ala Val Leu Ala Leu Gln Thr Ser Leu Val Phe Ser Arg Asp Phe Gly
     50                  55                  60

Leu Leu Val Phe Val Arg Lys Ser Leu Asn Ser Ile Glu Phe Arg Glu
 65                  70                  75                  80

Cys Arg Glu Glu Ile Leu Lys Phe Leu Cys Ile Phe Leu Glu Lys Met
                 85                  90                  95

Gly Gln Lys Ile Ala Pro Tyr Ser Val Glu Ile Lys Asn Thr Cys Thr
            100                 105                 110

Ser Val Tyr Thr Lys Asp Arg Ala Ala Lys Cys Lys Ile Pro Ala Leu
        115                 120                 125

Asp Leu Leu Ile Lys Leu Leu Gln Thr Phe Arg Ser Ser Arg Leu Met
    130                 135                 140

Asp Glu Phe Lys Ile Gly Glu Leu Phe Ser Lys Phe Tyr Gly Glu Leu
145                 150                 155                 160

Ala Leu Lys Lys Lys Ile Pro Asp Thr Val Leu Glu Lys Val Tyr Glu
                165                 170                 175

Leu Leu Gly Leu Leu Gly Glu Val His Pro Ser Glu Met Ile Asn Asn
            180                 185                 190
```

-continued

```
Ala Glu Asn Leu Phe Arg Ala Phe Leu Gly Glu Leu Lys Thr Gln Met
            195                 200                 205
Thr Ser Ala Val Arg Glu Pro Lys Leu Pro Val Leu Ala Gly Cys Leu
            210                 215                 220
Lys Gly Leu Ser Ser Leu Leu Cys Asn Phe Thr Lys Ser Met Glu Glu
225                 230                 235                 240
Asp Pro Gln Thr Ser Arg Glu Ile Phe Asn Phe Val Leu Lys Ala Ile
            245                 250                 255
Arg Pro Gln Ile Asp Leu Lys Arg Tyr Ala Val Pro Ser Ala Gly Leu
            260                 265                 270
Arg Leu Phe Ala Leu His Ala Ser Gln Phe Ser Thr Cys Leu Leu Asp
            275                 280                 285
Asn Tyr Val Ser Leu Phe Glu Val Leu Leu Lys Trp Cys Ala His Thr
            290                 295                 300
Asn Val Glu Leu Lys Lys Ala Ala Leu Ser Ala Leu Glu Ser Phe Leu
305                 310                 315                 320
Lys Gln Val Ser Asn Met Val Ala Lys Asn Ala Glu Met His Lys Asn
            325                 330                 335
Lys Leu Gln Tyr Phe Met Glu Gln Phe Tyr Gly Ile Ile Arg Asn Val
            340                 345                 350
Asp Ser Asn Asn Lys Glu Leu Ser Ile Ala Ile Arg Gly Tyr Gly Leu
            355                 360                 365
Phe Ala Gly Pro Cys Lys Val Ile Asn Ala Lys Asp Val Asp Phe Met
            370                 375                 380
Tyr Val Glu Leu Ile Gln Arg Cys Lys Gln Met Phe Leu Thr Gln Thr
385                 390                 395                 400
Asp Thr Gly Asp Tyr Arg Val Tyr Gln Met Pro Ser Phe Leu Gln Ser
            405                 410                 415
Val Ala Ser Val Leu Leu Tyr Leu Asp Thr Val Pro Glu Val Tyr Thr
            420                 425                 430
Pro Val Leu Glu His Leu Val Val Met Gln Ile Asp Ser Phe Pro Gln
            435                 440                 445
Tyr Ser Pro Lys Met Gln Leu Val Cys Cys Arg Ala Ile Val Lys Val
            450                 455                 460
Phe Leu Ala Leu Ala Ala Lys Gly Pro Val Leu Arg Asn Cys Ile Ser
465                 470                 475                 480
Thr Val Val His Gln Gly Leu Ile Arg Ile Cys Ser Lys Pro Val Val
            485                 490                 495
Leu Pro Lys Gly Pro Glu Ser Glu Ser Glu Asp His Arg Ala Ser Gly
            500                 505                 510
Glu Val Arg Thr Gly Lys Trp Lys Val Pro Thr Tyr Lys Asp Tyr Val
            515                 520                 525
Asp Leu Phe Arg His Leu Leu Ser Ser Asp Gln Met Met Asp Ser Ile
            530                 535                 540
Leu Ala Asp Glu Ala Phe Phe Ser Val Asn Ser Ser Glu Ser Leu
545                 550                 555                 560
Asn His Leu Leu Tyr Asp Glu Phe Val Lys Ser Val Leu Lys Ile Val
            565                 570                 575
Glu Lys Leu Asp Leu Thr Leu Glu Ile Gln Thr Val Gly Glu Gln Glu
            580                 585                 590
Asn Gly Asp Glu Ala Pro Gly Val Trp Met Ile Pro Thr Ser Asp Pro
            595                 600                 605
```

Ala Ala Asn Leu His Pro Ala Lys Pro Lys Asp Phe Ser Ala Phe Ile
610                 615                 620

Asn Leu Val Glu Phe Cys Arg Glu Ile Leu Pro Glu Lys Gln Ala Glu
625                 630                 635                 640

Phe Phe Glu Pro Trp Val Tyr Ser Phe Ser Tyr Glu Leu Ile Leu Gln
            645                 650                 655

Ser Thr Arg Leu Pro Leu Ile Ser Gly Phe Tyr Lys Leu Leu Ser Ile
            660                 665                 670

Thr Val Arg Asn Ala Lys Lys Ile Lys Tyr Phe Glu Gly Val Ser Pro
            675                 680                 685

Lys Ser Leu Lys His Ser Pro Glu Asp Pro Glu Lys Tyr Ser Cys Phe
690                 695                 700

Ala Leu Phe Val Lys Phe Gly Lys Glu Val Ala Val Lys Met Lys Gln
705                 710                 715                 720

Tyr Lys Asp Glu Leu Leu Ala Ser Cys Leu Thr Phe Leu Leu Ser Leu
                725                 730                 735

Pro His Asn Ile Ile Glu Leu Asp Val Arg Ala Tyr Val Pro Ala Leu
            740                 745                 750

Gln Met Ala Phe Lys Leu Gly Leu Ser Tyr Thr Pro Leu Ala Glu Val
            755                 760                 765

Gly Leu Asn Ala Leu Glu Glu Trp Ser Ile Tyr Ile Asp Arg His Val
770                 775                 780

Met Gln Pro Tyr Tyr Lys Asp Ile Leu Pro Cys Leu Asp Gly Tyr Leu
785                 790                 795                 800

Lys Thr Ser Ala Leu Ser Asp Glu Thr Lys Asn Asn Trp Glu Val Ser
                805                 810                 815

Ala Leu Ser Arg Ala Ala Gln Lys Gly Phe Asn Lys Val Val Leu Lys
            820                 825                 830

His Leu Lys Lys Thr Lys Asn Leu Ser Ser Asn Glu Ala Ile Ser Leu
            835                 840                 845

Glu Glu Ile Arg Ile Arg Val Val Gln Met Leu Gly Ser Leu Gly Gly
850                 855                 860

Gln Ile Asn Lys Asn Leu Leu Thr Val Thr Ser Ser Asp Glu Met Met
865                 870                 875                 880

Lys Ser Tyr Val Ala Trp Asp Arg Glu Lys Arg Leu Ser Phe Ala Val
                885                 890                 895

Pro Phe Arg Glu Met Lys Pro Val Ile Phe Leu Asp Val Phe Leu Pro
            900                 905                 910

Arg Val Thr Glu Leu Ala Leu Thr Ala Ser Asp Arg Gln Thr Lys Val
            915                 920                 925

Ala Ala Cys Glu Leu Leu His Ser Met Val Met Phe Met Leu Gly Lys
930                 935                 940

Ala Thr Gln Met Pro Glu Gly Gly Gln Gly Ala Pro Pro Met Tyr Gln
945                 950                 955                 960

Leu Tyr Lys Arg Thr Phe Pro Val Leu Leu Arg Leu Ala Cys Asp Val
                965                 970                 975

Asp Gln Val Thr Arg Gln Leu Tyr Glu Pro Leu Val Met Gln Leu Ile
            980                 985                 990

His Trp Phe Thr Asn Asn Lys Lys Phe Glu Ser Gln Asp Thr Val Ser
            995                 1000                1005

Leu Leu Glu Ala Ile Leu Asp Gly Ile Val Asp Pro Val Asp Ser Thr
    1010                1015                1020

Leu Arg Asp Phe Cys Gly Arg Cys Ile Arg Glu Phe Leu Lys Trp Ser

-continued

```
           1025                1030                1035                1040
Ile Lys Gln Ile Thr Pro Gln Gln Gln Glu Lys Ser Pro Val Asn Thr
                1045                1050                1055
Lys Ser Leu Phe Lys Arg Leu Tyr Ser Leu Ala Leu His Pro Asn Ala
                1060                1065                1070
Phe Lys Arg Leu Gly Ala Ser Leu Ala Phe Asn Asn Ile Tyr Arg Glu
                1075                1080                1085
Phe Arg Glu Glu Glu Ser Leu Val Glu Gln Phe Val Phe Glu Ala Leu
           1090                1095                1100
Val Ile Tyr Met Glu Ser Leu Ala Leu Ala His Ala Asp Glu Lys Ser
1105                1110                1115                1120
Leu Gly Thr Ile Gln Gln Cys Cys Asp Ala Ile Asp His Leu Cys Arg
                1125                1130                1135
Ile Ile Glu Lys Lys His Val Ser Leu Asn Lys Ala Lys Lys Arg Arg
                1140                1145                1150
Leu Pro Arg Gly Phe Pro Pro Ser Ala Ser Leu Cys Leu Leu Asp Leu
                1155                1160                1165
Val Lys Trp Leu Leu Ala His Cys Gly Arg Pro Gln Thr Glu Cys Arg
           1170                1175                1180
His Lys Ser Ile Glu Leu Phe Tyr Lys Phe Val Pro Leu Leu Pro Gly
1185                1190                1195                1200
Asn Arg Ser Pro Asn Leu Trp Leu Lys Asp Val Leu Lys Glu Glu Gly
                1205                1210                1215
Val Ser Phe Leu Ile Asn Thr Phe Glu Gly Gly Gly Cys Gly Gln Pro
                1220                1225                1230
Ser Gly Ile Leu Ala Gln Pro Thr Leu Leu Tyr Leu Arg Gly Pro Phe
           1235                1240                1245
Ser Leu Gln Ala Thr Leu Cys Trp Leu Asp Leu Leu Leu Ala Ala Leu
           1250                1255                1260
Glu Cys Tyr Asn Thr Phe Ile Gly Glu Arg Thr Val Gly Ala Leu Gln
1265                1270                1275                1280
Val Leu Gly Thr Glu Ala Gln Ser Ser Leu Leu Lys Ala Val Ala Phe
                1285                1290                1295
Phe Leu Glu Ser Ile Ala Met His Asp Ile Ile Ala Ala Glu Lys Cys
                1300                1305                1310
Phe Gly Thr Gly Ala Ala Gly Asn Arg Thr Ser Pro Gln Glu Gly Glu
           1315                1320                1325
Arg Tyr Asn Tyr Ser Lys Cys Thr Val Val Arg Ile Met Glu Phe
           1330                1335                1340
Thr Thr Thr Leu Leu Asn Thr Ser Pro Glu Gly Trp Lys Leu Leu Lys
1345                1350                1355                1360
Lys Asp Leu Cys Asn Thr His Leu Met Arg Val Leu Val Gln Thr Leu
                1365                1370                1375
Cys Glu Pro Ala Ser Ile Gly Phe Asn Ile Gly Asp Val Gln Val Met
           1380                1385                1390
Ala His Leu Pro Asp Val Cys Val Asn Leu Met Lys Ala Leu Lys Met
           1395                1400                1405
Ser Pro Tyr Lys Asp Ile Leu Glu Thr His Leu Arg Glu Lys Ile Thr
           1410                1415                1420
Ala Gln Ser Ile Glu Glu Leu Cys Ala Val Asn Leu Tyr Gly Pro Asp
1425                1430                1435                1440
Ala Gln Val Asp Arg Ser Arg Leu Ala Ala Val Val Ser Ala Cys Lys
                1445                1450                1455
```

```
Gln Leu His Arg Ala Gly Leu Leu His Asn Ile Leu Pro Ser Gln Ser
        1460                1465                1470

Thr Asp Leu His His Ser Val Gly Thr Glu Leu Leu Ser Leu Val Tyr
    1475                1480                1485

Lys Gly Ile Ala Pro Gly Asp Glu Arg Gln Cys Leu Pro Ser Leu Asp
        1490                1495                1500

Leu Ser Cys Lys Gln Leu Ala Ser Gly Leu Leu Glu Leu Ala Phe Ala
1505                1510                1515                1520

Phe Gly Gly Leu Cys Glu Arg Leu Val Ser Leu Leu Asn Pro Ala
    1525                1530                1535

Val Leu Ser Thr Ala Ser Leu Gly Ser Ser Gln Gly Ser Val Ile His
        1540                1545                1550

Phe Ser His Gly Glu Tyr Phe Tyr Ser Leu Phe Ser Glu Thr Ile Asn
    1555                1560                1565

Thr Glu Leu Leu Lys Asn Leu Asp Leu Ala Val Leu Glu Leu Met Gln
    1570                1575                1580

Ser Ser Val Asp Asn Thr Lys Met Val Ser Ala Val Leu Asn Gly Met
1585                1590                1595                1600

Leu Asp Gln Ser Phe Arg Glu Arg Ala Asn Gln Lys His Gln Gly Leu
        1605                1610                1615

Lys Leu Ala Thr Thr Ile Leu Gln His Trp Lys Lys Cys Asp Ser Trp
        1620                1625                1630

Trp Ala Lys Asp Ser Pro Leu Glu Thr Lys Met Ala Val Leu Ala Leu
    1635                1640                1645

Leu Ala Lys Ile Leu Gln Ile Asp Ser Ser Val Ser Phe Asn Thr Ser
    1650                1655                1660

His Gly Ser Phe Pro Glu Val Phe Thr Thr Tyr Ile Ser Leu Leu Ala
1665                1670                1675                1680

Asp Thr Lys Leu Asp Leu His Leu Lys Gly Gln Ala Val Thr Leu Leu
        1685                1690                1695

Pro Phe Phe Thr Ser Leu Thr Gly Gly Ser Leu Glu Glu Leu Arg Arg
        1700                1705                1710

Val Leu Glu Gln Leu Ile Val Ala His Phe Pro Met Gln Ser Arg Glu
    1715                1720                1725

Phe Pro Pro Gly Thr Pro Arg Phe Asn Asn Tyr Val Asp Cys Met Lys
1730                1735                1740

Lys Phe Leu Asp Ala Leu Glu Leu Ser Gln Ser Pro Met Leu Leu Glu
1745                1750                1755                1760

Leu Met Thr Glu Val Leu Cys Arg Glu Gln Gln His Val Met Glu Glu
        1765                1770                1775

Leu Phe Gln Ser Ser Phe Arg Arg Ile Ala Arg Arg Gly Ser Cys Val
        1780                1785                1790

Thr Gln Val Gly Leu Leu Glu Ser Val Tyr Glu Met Phe Arg Lys Asp
        1795                1800                1805

Asp Pro Arg Leu Ser Phe Thr Arg Gln Ser Phe Val Asp Arg Ser Leu
    1810                1815                1820

Leu Thr Leu Leu Trp His Cys Ser Leu Asp Ala Leu Arg Glu Phe Phe
1825                1830                1835                1840

Ser Thr Ile Val Val Asp Ala Ile Asp Val Leu Lys Ser Arg Phe Thr
        1845                1850                1855

Lys Leu Asn Glu Ser Thr Phe Asp Thr Gln Ile Thr Lys Lys Met Gly
        1860                1865                1870
```

-continued

Tyr Tyr Lys Ile Leu Asp Val Met Tyr Ser Arg Leu Pro Lys Asp Asp
    1875            1880            1885

Val His Ala Lys Glu Ser Lys Ile Asn Gln Val Phe His Gly Ser Cys
    1890            1895            1900

Ile Thr Glu Gly Asn Glu Leu Thr Lys Thr Leu Ile Lys Leu Cys Tyr
1905            1910            1915            1920

Asp Ala Phe Thr Glu Asn Met Ala Gly Glu Asn Gln Leu Leu Glu Arg
        1925            1930            1935

Arg Arg Leu Tyr His Cys Ala Ala Tyr Asn Cys Ala Ile Ser Val Ile
        1940            1945            1950

Cys Cys Val Phe Asn Glu Leu Lys Phe Tyr Gln Gly Phe Leu Phe Ser
        1955            1960            1965

Glu Lys Pro Glu Lys Asn Leu Leu Ile Phe Glu Asn Leu Ile Asp Leu
    1970            1975            1980

Lys Arg Arg Tyr Asn Phe Pro Val Glu Val Glu Val Pro Met Glu Arg
1985            1990            1995            2000

Lys Lys Lys Tyr Ile Glu Ile Arg Lys Glu Ala Arg Glu Ala Ala Asn
        2005            2010            2015

Gly Asp Ser Asp Gly Pro Ser Tyr Met Ser Ser Leu Ser Tyr Leu Ala
        2020            2025            2030

Asp Ser Thr Leu Ser Glu Glu Met Ser Gln Phe Asp Phe Ser Thr Gly
        2035            2040            2045

Val Gln Ser Tyr Ser Tyr Ser Ser Gln Asp Pro Arg Pro Ala Thr Gly
        2050            2055            2060

Arg Phe Arg Arg Arg Glu Gln Arg Asp Pro Thr Val His Asp Asp Val
2065            2070            2075            2080

Leu Glu Leu Glu Met Asp Glu Leu Asn Arg His Glu Cys Met Ala Pro
        2085            2090            2095

Leu Thr Ala Leu Val Lys His Met His Arg Ser Leu Gly Pro Pro Gln
        2100            2105            2110

Gly Glu Glu Asp Ser Val Pro Arg Asp Leu Pro Ser Trp Met Lys Phe
        2115            2120            2125

Leu His Gly Lys Leu Gly Asn Pro Ile Val Pro Leu Asn Ile Arg Leu
    2130            2135            2140

Phe Leu Ala Lys Leu Val Ile Asn Thr Glu Glu Val Phe Arg Pro Tyr
2145            2150            2155            2160

Ala Lys His Trp Leu Ser Pro Leu Leu Gln Leu Ala Ala Ser Glu Asn
        2165            2170            2175

Asn Gly Gly Glu Gly Ile His Tyr Met Val Val Glu Ile Val Ala Thr
        2180            2185            2190

Ile Leu Ser Trp Thr Gly Leu Ala Thr Pro Thr Gly Val Pro Lys Asp
        2195            2200            2205

Glu Val Leu Ala Asn Arg Leu Leu Asn Phe Leu Met Lys His Val Phe
    2210            2215            2220

His Pro Lys Arg Ala Val Phe Arg His Asn Leu Glu Ile Ile Lys Thr
2225            2230            2235            2240

Leu Val Glu Cys Trp Lys Asp Cys Leu Ser Ile Pro Tyr Arg Leu Ile
            2245            2250            2255

Phe Glu Lys Phe Ser Gly Lys Asp Pro Asn Ser Lys Asp Asn Ser Val
        2260            2265            2270

Gly Ile Gln Leu Leu Gly Ile Val Met Ala Asn Asp Leu Pro Pro Tyr
        2275            2280            2285

Asp Pro Gln Cys Gly Ile Gln Ser Ser Glu Tyr Phe Gln Ala Leu Val 2290                2295                  2300
Asn Asn Met Ser Phe Val Arg Tyr Lys Glu Val Tyr Ala Ala Ala Ala
2305                2310                  2315                 2320

Glu Val Leu Gly Leu Ile Leu Arg Tyr Val Met Glu Arg Lys Asn Ile
           2325                  2330                 2335

Leu Glu Glu Ser Leu Cys Glu Leu Val Ala Lys Gln Leu Lys Gln His
           2340                  2345                 2350

Gln Asn Thr Met Glu Asp Lys Phe Ile Val Cys Leu Asn Lys Val Thr
           2355                  2360                 2365

Lys Ser Phe Pro Pro Leu Ala Asp Arg Phe Met Asn Ala Val Phe Phe
      2370                  2375                 2380

Leu Leu Pro Lys Phe His Gly Val Leu Lys Thr Leu Cys Leu Glu Val
2385                2390                  2395                 2400

Val Leu Cys Arg Val Glu Gly Met Thr Glu Leu Tyr Phe Gln Leu Lys
           2405                  2410                 2415

Ser Lys Asp Phe Val Gln Val Met Arg His Arg Asp Glu Arg Gln Lys
           2420                  2425                 2430

Val Cys Leu Asp Ile Ile Tyr Lys Met Met Pro Lys Leu Lys Pro Val
           2435                  2440                 2445

Glu Leu Arg Glu Leu Leu Asn Pro Val Val Glu Phe Val Ser His Pro
      2450                  2455                 2460

Ser Thr Thr Cys Arg Glu Gln Met Tyr Asn Ile Leu Met Trp Ile His
2465                2470                  2475                 2480

Asp Asn Tyr Arg Asp Pro Glu Ser Glu Thr Asp Asn Asp Ser Gln Glu
           2485                  2490                 2495

Ile Phe Lys Leu Ala Lys Asp Val Leu Ile Gln Gly Leu Ile Asp Glu
           2500                  2505                 2510

Asn Pro Gly Leu Gln Leu Ile Ile Arg Asn Phe Trp Ser His Glu Thr
           2515                  2520                 2525

Arg Leu Pro Ser Asn Thr Leu Asp Arg Leu Leu Ala Leu Asn Ser Leu
      2530                  2535                 2540

Tyr Ser Pro Lys Ile Glu Val His Phe Leu Ser Leu Ala Thr Asn Phe
2545                2550                  2555                 2560

Leu Leu Glu Met Thr Ser Met Ser Pro Asp Tyr Pro Asn Pro Met Phe
           2565                  2570                 2575

Glu His Pro Leu Ser Glu Cys Glu Phe Gln Glu Tyr Thr Ile Asp Ser
              2580                  2585                 2590

Asp Trp Arg Phe Arg Ser Thr Val Leu Thr Pro Met Phe Val Glu Thr
      2595                  2600                 2605

Gln Ala Ser Gln Gly Thr Leu Gln Thr Arg Thr Gln Glu Gly Ser Leu
      2610                  2615                 2620

Ser Ala Arg Trp Pro Val Ala Gly Gln Ile Arg Ala Thr Gln Gln Gln
2625                2630                  2635                 2640

His Asp Phe Thr Leu Thr Gln Thr Ala Asp Gly Arg Ser Ser Phe Asp
           2645                  2650                 2655

Trp Leu Thr Gly Ser Ser Thr Asp Pro Leu Val Asp His Thr Ser Pro
           2660                  2665                 2670

Ser Ser Asp Ser Leu Leu Phe Ala His Lys Arg Ser Glu Arg Leu Gln
           2675                  2680                 2685

Arg Ala Pro Leu Lys Ser Val Gly Pro Asp Phe Gly Lys Lys Arg Leu
      2690                  2695                 2700

Gly Leu Pro Gly Asp Glu Val Asp Asn Lys Val Lys Gly Ala Ala Gly
2705                2710                  2715                 2720

-continued

```
Arg Thr Asp Leu Leu Arg Leu Arg Arg Arg Phe Met Arg Asp Gln Glu
            2725                2730                2735
Lys Leu Ser Leu Met Tyr Ala Arg Lys Gly Val Ala Glu Gln Lys Arg
            2740                2745                2750
Glu Lys Glu Ile Lys Ser Glu Leu Lys Met Lys Gln Asp Ala Gln Val
            2755                2760                2765
Val Leu Tyr Arg Ser Tyr Arg His Gly Asp Leu Pro Asp Ile Gln Ile
            2770                2775                2780
Lys His Ser Ser Leu Ile Thr Pro Leu Gln Ala Val Ala Gln Arg Asp
2785                2790                2795                2800
Pro Ile Ile Ala Lys Gln Leu Phe Ser Ser Leu Phe Ser Gly Ile Leu
            2805                2810                2815
Lys Glu Met Asp Lys Phe Lys Thr Leu Ser Glu Lys Asn Asn Ile Thr
            2820                2825                2830
Gln Lys Leu Leu Gln Asp Phe Asn Arg Phe Leu Asn Thr Thr Phe Ser
            2835                2840                2845
Phe Phe Pro Pro Phe Val Ser Cys Ile Gln Asp Ile Ser Cys Gln His
            2850                2855                2860
Ala Ala Leu Leu Ser Leu Asp Pro Ala Ala Val Ser Ala Gly Cys Leu
2865                2870                2875                2880
Ala Ser Leu Gln Gln Pro Val Gly Ile Arg Leu Leu Glu Glu Ala Leu
            2885                2890                2895
Leu Arg Leu Leu Pro Ala Glu Leu Pro Ala Lys Arg Val Arg Gly Lys
            2900                2905                2910
Ala Arg Leu Pro Pro Asp Val Leu Arg Trp Val Glu Leu Ala Lys Leu
            2915                2920                2925
Tyr Arg Ser Ile Gly Glu Tyr Asp Val Leu Arg Gly Ile Phe Thr Ser
            2930                2935                2940
Glu Ile Gly Thr Lys Gln Ile Thr Gln Ser Ala Leu Leu Ala Glu Ala
2945                2950                2955                2960
Arg Ser Asp Tyr Ser Glu Ala Ala Lys Gln Tyr Asp Glu Ala Leu Asn
            2965                2970                2975
Lys Gln Asp Trp Val Asp Gly Glu Pro Thr Glu Ala Glu Lys Asp Phe
            2980                2985                2990
Trp Glu Leu Ala Ser Leu Asp Cys Tyr Asn His Leu Ala Glu Trp Lys
            2995                3000                3005
Ser Leu Glu Tyr Cys Ser Thr Ala Ser Ile Asp Ser Glu Asn Pro Pro
            3010                3015                3020
Asp Leu Asn Lys Ile Trp Ser Glu Pro Phe Tyr Gln Glu Thr Tyr Leu
3025                3030                3035                3040
Pro Tyr Met Ile Arg Ser Lys Leu Lys Leu Leu Leu Gln Gly Glu Ala
            3045                3050                3055
Asp Gln Ser Leu Leu Thr Phe Ile Asp Lys Ala Met His Gly Glu Leu
            3060                3065                3070
Gln Lys Ala Ile Leu Glu Leu His Tyr Ser Gln Glu Leu Ser Leu Leu
            3075                3080                3085
Tyr Leu Leu Gln Asp Asp Val Asp Arg Ala Lys Tyr Tyr Ile Gln Asn
            3090                3095                3100
Gly Ile Gln Ser Phe Met Gln Asn Tyr Ser Ser Ile Asp Val Leu Leu
3105                3110                3115                3120
His Gln Ser Arg Leu Thr Lys Leu Gln Ser Val Gln Ala Leu Thr Glu
            3125                3130                3135
```

```
Ile Gln Glu Phe Ile Ser Phe Ile Ser Lys Gln Gly Asn Leu Ser Ser
        3140                3145                3150

Gln Val Pro Leu Lys Arg Leu Leu Asn Thr Trp Thr Asn Arg Tyr Pro
        3155                3160                3165

Asp Ala Lys Met Asp Pro Met Asn Ile Trp Asp Ile Ile Thr Asn
    3170                3175                3180

Arg Cys Phe Phe Leu Ser Lys Ile Glu Glu Lys Leu Thr Pro Leu Pro
3185                3190                3195                3200

Glu Asp Asn Ser Met Asn Val Asp Gln Asp Gly Asp Pro Ser Asp Arg
        3205                3210                3215

Met Glu Val Gln Glu Gln Glu Glu Asp Ile Ser Ser Leu Ile Arg Ser
        3220                3225                3230

Cys Lys Phe Ser Met Lys Met Lys Met Ile Asp Ser Ala Arg Lys Gln
        3235                3240                3245

Asn Asn Phe Ser Leu Ala Met Lys Leu Leu Lys Glu Leu His Lys Glu
        3250                3255                3260

Ser Lys Thr Arg Asp Asp Trp Leu Val Ser Trp Val Gln Ser Tyr Cys
3265                3270                3275                3280

Arg Leu Ser His Cys Arg Ser Arg Ser Gln Gly Cys Ser Glu Gln Val
        3285                3290                3295

Leu Thr Val Leu Lys Thr Val Ser Leu Leu Asp Glu Asn Asn Val Ser
        3300                3305                3310

Ser Tyr Leu Xaa Lys Asn Ile Leu Ala Phe Arg Asp Gln Asn Ile Leu
        3315                3320                3325

Leu Gly Thr Thr Tyr Arg Ile Ile Ala Asn Ala Leu Ser Ser Glu Pro
        3330                3335                3340

Ala Cys Leu Ala Glu Ile Glu Glu Asp Lys Ala Arg Arg Ile Leu Glu
3345                3350                3355                3360

Leu Ser Gly Ser Ser Ser Glu Asp Ser Glu Lys Val Ile Ala Gly Leu
        3365                3370                3375

Tyr Gln Arg Ala Phe Gln His Leu Ser Glu Ala Val Gln Ala Ala Glu
        3380                3385                3390

Glu Glu Ala Gln Pro Pro Ser Trp Ser Cys Gly Pro Ala Ala Gly Val
        3395                3400                3405

Ile Asp Ala Tyr Met Thr Leu Ala Asp Phe Cys Asp Gln Gln Leu Arg
        3410                3415                3420

Lys Glu Glu Glu Asn Ala Ser Val Thr Asp Ser Ala Glu Leu Gln Ala
3425                3430                3435                3440

Tyr Pro Ala Leu Val Val Glu Lys Met Leu Lys Ala Leu Lys Leu Asn
        3445                3450                3455

Ser Asn Glu Ala Arg Leu Lys Phe Pro Arg Leu Leu Gln Ile Ile Glu
        3460                3465                3470

Arg Tyr Pro Glu Glu Thr Leu Ser Leu Met Thr Lys Glu Ile Ser Ser
        3475                3480                3485

Val Pro Cys Trp Gln Phe Ile Ser Trp Ile Ser His Met Val Ala Leu
        3490                3495                3500

Leu Asp Lys Asp Gln Ala Val Ala Val Gln His Ser Val Glu Glu Ile
3505                3510                3515                3520

Thr Asp Asn Tyr Pro Gln Ala Ile Val Tyr Pro Phe Ile Ile Ser Ser
        3525                3530                3535

Glu Ser Tyr Ser Phe Lys Asp Thr Ser Thr Gly His Lys Asn Lys Glu
        3540                3545                3550

Phe Val Ala Arg Ile Lys Ser Lys Leu Asp Gln Gly Gly Val Ile Gln
```

|  |  |  |
|---|---|---|
| 3555 | 3560 | 3565 |

Asp Phe Ile Asn Ala Leu Asp Gln Leu Ser Asn Pro Glu Leu Leu Phe
         3570                3575                3580

Lys Asp Trp Ser Asn Asp Val Arg Ala Glu Leu Ala Lys Thr Pro Val
3585                3590                3595                3600

Asn Lys Lys Asn Ile Glu Lys Met Tyr Glu Arg Met Tyr Ala Ala Leu
              3605                3610                3615

Gly Asp Pro Lys Ala Pro Gly Leu Gly Ala Phe Arg Lys Phe Ile
         3620                3625                3630

Gln Thr Phe Gly Lys Glu Phe Asp Lys His Phe Gly Lys Gly Gly Ser
         3635                3640                3645

Lys Leu Leu Arg Met Lys Leu Ser Asp Phe Asn Asp Ile Thr Asn Met
    3650                3655                3660

Leu Leu Leu Lys Met Asn Lys Asp Ser Lys Pro Pro Gly Asn Leu Lys
3665                3670                3675                3680

Glu Cys Ser Pro Trp Met Ser Asp Phe Lys Val Glu Phe Leu Arg Asn
              3685                3690                3695

Glu Leu Glu Ile Pro Gly Gln Tyr Asp Gly Arg Gly Lys Pro Leu Pro
         3700                3705                3710

Glu Tyr His Val Arg Ile Ala Gly Phe Asp Glu Arg Val Thr Val Met
         3715                3720                3725

Ala Ser Leu Arg Arg Pro Lys Arg Ile Ile Ile Arg Gly His Asp Glu
    3730                3735                3740

Arg Glu His Pro Phe Leu Val Lys Gly Gly Glu Asp Leu Arg Gln Asp
3745                3750                3755                3760

Gln Arg Val Glu Gln Leu Phe Gln Val Met Asn Gly Ile Leu Ala Gln
              3765                3770                3775

Asp Ser Ala Cys Ser Gln Arg Ala Leu Gln Leu Arg Thr Tyr Ser Val
         3780                3785                3790

Val Pro Met Thr Ser Ser Asp Pro Arg Ala Pro Pro Cys Glu Tyr Lys
         3795                3800                3805

Asp Trp Leu Thr Lys Met Ser Gly Lys His Asp Val Gly Ala Tyr Met
    3810                3815                3820

Leu Met Tyr Lys Gly Ala Asn Arg Thr Glu Thr Val Thr Ser Phe Arg
3825                3830                3835                3840

Lys Arg Glu Ser Lys Val Pro Ala Asp Leu Leu Lys Arg Ala Phe Val
              3845                3850                3855

Arg Met Ser Thr Ser Pro Glu Ala Phe Leu Ala Leu Arg Ser His Phe
         3860                3865                3870

Ala Ser Ser His Ala Leu Ile Cys Ile Ser His Trp Ile Leu Gly Ile
         3875                3880                3885

Gly Asp Arg His Leu Asn Asn Phe Met Val Ala Met Glu Thr Gly Gly
    3890                3895                3900

Val Ile Gly Ile Asp Phe Gly His Ala Phe Gly Ser Ala Thr Gln Phe
3905                3910                3915                3920

Leu Pro Val Pro Glu Leu Met Pro Phe Arg Leu Thr Arg Gln Phe Ile
              3925                3930                3935

Asn Leu Met Leu Pro Met Lys Glu Thr Gly Leu Met Tyr Ser Ile Met
         3940                3945                3950

Val His Ala Leu Arg Ala Phe Arg Ser Asp Pro Gly Leu Leu Thr Asn
    3955                3960                3965

Thr Met Asp Val Phe Val Lys Glu Pro Ser Phe Asp Trp Lys Asn Phe
    3970                3975                3980

```
Glu Gln Lys Met Leu Lys Lys Gly Gly Ser Trp Ile Gln Glu Ile Asn
3985                3990                3995                4000

Val Ala Glu Lys Asn Trp Tyr Pro Arg Gln Lys Ile Cys Tyr Ala Lys
            4005                4010                4015

Arg Lys Leu Ala Gly Ala Asn Pro Ala Val Ile Thr Cys Asp Glu Leu
        4020                4025                4030

Leu Leu Gly His Glu Lys Ala Pro Ala Phe Arg Asp Tyr Val Ala Val
        4035                4040                4045

Ala Arg Gly Ser Lys Asp His Asn Ile Arg Ala Gln Glu Pro Glu Ser
    4050                4055                4060

Gly Leu Ser Glu Glu Thr Gln Val Lys Cys Leu Met Asp Gln Ala Thr
4065                4070                4075                4080

Asp Pro Asn Ile Leu Gly Arg Thr Trp Glu Gly Trp Glu Pro Trp Met
            4085                4090                4095

<210> SEQ ID NO 8
<211> LENGTH: 12780
<212> TYPE: DNA
<213> ORGANISM: Homo sapiens

<400> SEQUENCE: 8
atttccgggt ccgggccgag cgggcgcacg cgcgggagcg ggactcggcg gcatggcggg      60
ctccggagcc ggtgtgcgtt gctccctgct gcggctgcag gagaccttgt ccgctgcgga     120
ccgctgcggt gctgccctgg ccggtcatca actgatccgc ggcctggggc aggaatgcgt     180
cctgagcagc agccccgcgg tgctggcatt acagacatct ttagtttttt ccagagattt     240
cggtttgctt gtatttgtcc ggaagtcact caacagtatt gaatttcgtg aatgtagaga     300
agaaatccta aagttttat gtattttctt agaaaaaatg ggccagaaga tcgcacctta     360
ctctgttgaa attaagaaca cttgtaccag tgtttataca aaagatagag ctgctaaatg     420
taaaattcca gccctggacc ttcttattaa gttacttcag acttttagaa gttctagact     480
catggatgaa tttaaaattg gagaattatt tagtaaattc tatggagaac ttgcattgaa     540
aaaaaaaata ccagatacag ttttagaaaa agtatatgag ctcctaggat tattgggtga     600
agttcatcct agtgagatga taaataatgc agaaaacctg ttccgcgctt ttctgggtga     660
acttaagacc cagatgacat cagcagtaag agagcccaaa ctacctgttc tggcaggatg     720
tctgaagggg ttgtcctcac ttctgtgcaa cttcactaag tccatggaag aagatcccca     780
gacttcaagg gagattttta attttgtact aaaggcaatt cgtcctcaga ttgatctgaa     840
gagatatgct gtgccctcag ctggcttgcg cctatttgcc ctgcatgcat ctcagtttag     900
cacctgcctt ctggacaact acgtgtctct atttgaagtc ttgttaaagt ggtgtgccca     960
cacaaatgta gaattgaaaa agctgcact ttcagccctg gaatcctttc tgaaacaggt    1020
ttctaatatg gtggcgaaaa atgcagaaat gcataaaaat aaactgcagt actttatgga    1080
gcagttttat ggaatcatca gaaatgtgga ttcgaacaac aaggagttat ctattgctat    1140
ccgtggatat ggactttttg caggaccgtg caaggttata aacgcaaaag atgttgactt    1200
catgtacgtt gagctcattc agcgctgcaa gcagatgttc ctcacccaga cagacactgg    1260
tgactaccgt gtttatcaga tgccaagctt cctccagtct gttgcaagcg tcttgctgta    1320
ccttgacaca gttcctgagg tgtatactcc agttctggag cacctcgtgg tgatgcagat    1380
agacagtttc ccacagtaca gtccaaaaat gcagctggtg tgttcagag ccatagtgaa    1440
ggtgttccta gctttggcag caaaagggcc agttctcagg aattgcatta gtactgtggt    1500
```

```
gcatcagggt ttaatcagaa tatgttctaa accagtggtc cttccaaagg gccctgagtc   1560
tgaatctgaa gaccaccgtg cttcagggga agtcagaact ggcaaatgga aggtgcccac   1620
atacaaagac tacgtggatc tcttcagaca tctcctgagc tctgaccaga tgatggattc   1680
tattttagca gatgaagcat ttttctctgt gaattcctcc agtgaaagtc tgaatcattt   1740
actttatgat gaatttgtaa atccgttttt gaagattgtt gagaaattgg atcttacact   1800
tgaaatacag actgttgggg aacaagagaa tggagatgag gcgcctggtg tttggatgat   1860
cccaacttca gatccagcgg ctaacttgca tccagctaaa cctaaagatt tttcggcttt   1920
cattaacctg gtggaatttt gcagagagat tctccctgag aaacaagcag aatttttttga  1980 accatgggtg tactcatttt catatgaatt aattttgcaa tctacaaggt tgcccctcat   2040
cagtggtttc tacaaattgc tttctattac agtaagaaat gccaagaaaa taaaatattt   2100
cgagggagtt agtccaaaga gtctgaaaca ctctcctgaa gacccagaaa gtattcttg   2160 cttttgcttta tttgtgaaat tggcaaaga ggtggcagtt aaaatgaagc agtacaaaga   2220
tgaacttttg gcctcttgtt tgacctttct tctgtccttg ccacacaaca tcattgaact   2280
cgatgttaga gcctacgttc ctgcactgca gatggctttc aaactgggcc tgagctatac   2340 cccttggca gaagtaggcc tgaatgctct agaagaatgg tcaatttata ttgacagaca   2400
tgtaatgcag ccttattaca aagacattct cccctgcctg gatggatacc tgaagacttc   2460
agccttgtca gatgagacca gaataactg ggaagtgtca gctctttctc gggctgccca   2520
gaaaggattt aataaagtgg tgttaaagca tctgaagaag acaaagaacc tttcatcaaa   2580
cgaagcaata tccttagaag aaataagaat tagagtagta caaatgcttg gatctctagg   2640
aggacaaata aacaaaaatc ttctgacagt cacgtcctca gatgagatga tgaagagcta   2700
tgtggcctgg gacagagaga agcggctgag cttgcagtg ccctttagag agatgaaacc   2760
tgtcattttc ctggatgtgt tcctgcctcg agtcacagaa ttagcgctca cagccagtga   2820
cagacaaact aaagttgcag cctgtgaact tttacatagc atggttatgt ttatgttggg   2880
caaagccacg cagatgccag aagggggaca gggagcccca cccatgtacc agctctataa   2940
gcggacgttt cctgtgctgc ttcgacttgc gtgtgatgtt gatcaggtga caaggcaact   3000
gtatgagcca ctagttatgc agctgattca ctggttcact aacaacaaga atttgaaag   3060 tcaggatact gtttccttac tagaagctat attggatgga attgtggacc ctgttgacag   3120
tactttaaga gattttgtgt gtcggtgtat tcgagaattc cttaaatggt ccattaagca   3180
aataacacca cagcagcagg agaagagtcc agtaaacacc aaatcgcttt tcaagcgact   3240
ttatagcctt gcgcttcacc ccaatgcttt caagaggctg ggagcatcac ttgcctttaa   3300
taatatctac agggaattca gggaagaaga gtctctggtg aacagtttg tgtttgaagc   3360 cttggtgata tacatggaga gtctggcctt agcacatgca gatgagaagt ccttaggtac   3420
aattcaacag tgttgtgatg ccattgatca cctatgccgc atcattgaaa agaagcatgt   3480
ttctttaaat aaagcaaaga aacgacgttt gccgcgagga tttccaccttt ccgcatcatt   3540 gtgtttattg gatctggtca agtggctttt agctcattgt gggaggcccc agacagaatg   3600
tcgacacaaa tccattgaac tctttttataa attcgttcct ttattgccag gcaacagatc   3660
ccctaatttg tggctgaaag atgttctcaa ggaagaaggt gtctctttc tcatcaacac   3720 ctttgagggg ggtggctgtg gccagccctc gggcatcctg gcccagccca ccctcttgta   3780 ccttcgggg ccattcagcc tgcaggccac gctatgctgg ctggacctgc tcctggccgc   3840
```

```
gttggagtgc tacaacacgt tcattggcga gagaactgta ggagcgctcc aggtcctagg    3900
tactgaagcc cagtcttcac tttttgaaagc agtggctttc ttcttagaaa gcattgccat   3960
gcatgacatt atagcagcag aaaagtgctt tggcactggg gcagcaggta acagaacaag    4020
cccacaagag ggagaaaggt acaactacag caaatgcacc gttgtggtcc ggattatgga   4080
gtttaccacg actctgctaa acacctcccc ggaaggatgg aagctcctga agaaggactt    4140
gtgtaataca cacctgatga gagtcctggt gcagacgctg tgtgagcccg caagcatagg    4200
tttcaacatc ggagacgtcc aggttatggc tcatcttcct gatgtttgtg tgaatctgat    4260
gaaagctcta aagatgtccc catacaaaga tatcctagag acccatctga gagagaaaat    4320
aacagcacag agcattgagg agctttgtgc cgtcaacttg tatggccctg acgcgcaagt    4380
ggacaggagc aggctggctg ctgttgtgtc tgcctgtaaa cagcttcaca gagctgggct    4440
tctgcataat atattaccgt ctcagtccac agatttgcat cattctgttg cacagaact    4500 tctttccctg gtttataaag gcattgcccc tggagatgag agacagtgtc tgccttctct    4560
agacctcagt tgtaagcagc tggccagcgg acttctggag ttagcctttg cttttggagg    4620
actgtgtgag cgccttgtga gtcttctcct gaacccagcg gtgctgtcca cggcgtcctt    4680
gggcagctca cagggcagcg tcatccactt ctcccatggg gagtatttct atagcttgtt    4740
ctcagaaacg atcaacacgg aattattgaa aaatctggat cttgctgtat ggagctcat    4800 gcagtcttca gtggataata ccaaaatggt gagtgccgtt ttgaacggca tgttagacca    4860
gagcttcagg gagcgagcaa accagaaaca ccaaggactg aaacttgcga ctacaattct    4920
gcaacactgg aagaagtgtg attcatggtg ggccaaagat tcccctctcg aaactaaaat    4980
ggcagtgctg gccttactgg caaaaatttt acagattgat tcatctgtat cttttaatac    5040
aagtcatggt tcattccctg aagtctttac aacatatatt agtctacttg ctgacacaaa    5100
gctggatcta catttaaagg gccaagctgt cactcttctt ccattcttca ccagcctcac    5160
tggaggcagt ctggaggaac ttagacgtgt tctggagcag ctcatcgttg ctcacttccc    5220
catgcagtcc agggaatttc ctccaggaac tccgcggttc ataattatg tggactgcat    5280 gaaaaagttt ctagatgcat tggaattatc tcaaagccct atgttgttgg aattgatgac    5340
agaagttctt tgtcgggaac agcagcatgt catggaagaa ttatttcaat ccagtttcag    5400
gaggattgcc agaaggggtt catgtgtcac acaagtaggc cttctggaaa gcgtgtatga    5460
aatgttcagg aaggatgacc cccgcctaag tttcacacgc cagtccttttg tggaccgctc    5520 cctcctcact ctgctgtggc actgtagcct ggatgctttg agagaattct tcagcacaat    5580
tgtggtggat gccattgatg tgttgaagtc caggtttaca aagctaaatg aatctacctt    5640
tgatactcaa atcaccaaga agatgggcta ctataagatt ctagacgtga tgtattctcg    5700
ccttcccaaa gatgatgttc atgctaagga atcaaaaatt aatcaagttt tccatggctc    5760
gtgtattaca gaaggaaatg aacttacaaa gacattgatt aaattgtgct acgatgcatt    5820
tacagagaac atggcaggag agaatcagct gctggagagg agaagacttt accattgtgc    5880
agcatacaac tgcgccatat ctgtcatctg ctgtgtcttc aatgagttaa aattttacca    5940
aggttttctg tttagtgaaa aaccagaaaa gaacttgctt attttttgaaa atctgatcga    6000 cctgaagcgc cgctataatt ttcctgtaga agttgaggtt cctatggaaa gaagaaaaa    6060 gtacattgaa attaggaaag aagccagaga agcagcaaat ggggattcag atggtccttc    6120
ctatatgtct tccctgtcat atttggcaga cagtaccctg agtgaggaaa tgagtcaatt    6180
tgatttctca accggagttc agagctattc atacagctcc caagaccctta gacctgccac    6240
```

-continued

```
tggtcgtttt cggagacggg agcagcggga ccccacggtg catgatgatg tgctggagct   6300
ggagatggac gagctcaatc ggcatgagtg catggcgccc ctgacggccc tggtcaagca   6360
catgcacaga agcctgggcc cgcctcaagg agaagaggat tcagtgccaa gagatcttcc   6420
ttcttggatg aaattcctcc atggcaaact gggaaatcca atagtaccat taaatatccg   6480
tctcttctta gccaagcttg ttattaatac agaagaggtc tttcgccctt acgcgaagca   6540
ctggcttagc cccttgctgc agctggctgc ttctgaaaac aatggaggag aaggaattca   6600
ctacatggtg gttgagatag tggccactat tctttcatgg acaggcttgg ccactccaac   6660
aggggtccct aaagatgaag tgttagcaaa tcgattgctt aatttcctaa tgaaacatgt   6720 cttttcatcca aaaagagctg tgtttagaca caaccttgaa attataaaga cccttgtcga   6780
gtgctggaag gattgtttat ccatccctta taggttaata tttgaaaagt tttccggtaa   6840
agatcctaat tctaaagaca actcagtagg gattcaattg ctaggcatcg tgatggccaa   6900
tgacctgcct ccctatgacc cacagtgtgg catccagagt agcgaatact tccaggcttt   6960
ggtgaataat atgtccttttg taagatataa agaagtgtat gccgctgcag cagaagttct   7020
aggacttata cttcgatatg ttatggagag aaaaaacata ctggaggagt ctctgtgtga   7080
actggttgcg aaacaattga agcaacatca gaatactatg gaggacaagt ttattgtgtg   7140
cttgaacaaa gtgaccaaga gcttccctcc tcttgcagac aggttcatga atgctgtgtt   7200 cttctctgctg ccaaaatttc atggagtgtt gaaaacactc tgtctggagg tggtactttg   7260
tcgtgtggag ggaatgacag agctgtactt ccagttaaag agcaaggact tcgttcaagt   7320
catgagacat agagatgaaa gacaaaaagt atgtttggac ataatttata agatgatgcc   7380
aaagttaaaa ccagtagaac tccgagaact tctgaacccc gttgtggaat tcgtttccca   7440
tccttctaca acatgtaggg aacaaatgta taatattctc atgtggattc atgataatta   7500
cagagatcca gaaagtgaga cagataatga ctcccaggaa atatttaagt tggcaaaaga   7560
tgtgctgatt caaggattga tcgatgagaa ccctggactt caattaatta ttcgaaattt   7620
ctggagccat gaaactaggt taccttcaaa taccttggac cggttgctgg cactaaattc   7680
cttatattct cctaagatag aagtgcactt tttaagttta gcaacaaatt ttctgctcga   7740
aatgaccagc atgagcccag attatccaaa ccccatgttc gagcatcctc tgtcagaatg   7800
cgaatttcag gaatatacca ttgattctga ttggcgtttc cgaagtactg ttctcactcc   7860
gatgtttgtg gagacccagg cctcccaggg cactctccag acccgtaccc aggaagggtc   7920
cctctcagct cgctggccag tggcagggca gataagggcc acccagcagc agcatgactt   7980
cacactgaca cagactgcag atggaagaag ctcatttgat tggctgaccg ggagcagcac   8040
tgacccgctg gtcgaccaca ccagtccctc atctgactcc ttgctgtttg cccacaagag   8100
gagtgaaagg ttacagagag cacccttgaa gtcagtgggg cctgattttg ggaaaaaaag   8160
gctgggcctt ccaggggacg aggtggataa caaagtgaaa ggtgcggccg ccggacgga   8220 cctactacga ctgcgcagac ggtttatgag ggaccaggag aagctcagtt tgatgtatgc   8280
cagaaaaggc gttgctgagc aaaaacgaga gaaggaaatc aagagtgagt taaaaatgaa   8340
gcaggatgcc caggtcgttc tgtacagaag ctaccggcac ggagaccttc ctgacattca   8400
gatcaagcac agcagcctca tcaccccgtt acaggccgtg gcccagaggg acccaataat   8460
tgcaaaacag ctcttttagca gcttgttttc tggaattttg aaagagatgg ataaatttaa   8520
gacactgtct gaaaaaaaca acatcactca aaagttgctt caagacttca atcgtttttct   8580
```

-continued

```
taataccacc ttctctttct ttccacccctt tgtctcttgt attcaggaca ttagctgtca    8640
gcacgcagcc ctgctgagcc tcgacccagc ggctgttagc gctggttgcc tggccagcct    8700
acagcagccc gtgggcatcc gcctgctaga ggaggctctg ctccgcctgc tgcctgctga    8760
gctgcctgcc aagcgagtcc gtgggaaggc ccgcctccct cctgatgtcc tcagatgggt    8820
ggagcttgct aagctgtata gatcaattgg agaatacgac gtcctccgtg ggatttttac    8880
cagtgagata ggaacaaagc aaatcactca gagtgcatta ttagcagaag ccagaagtga    8940
ttattctgaa gctgctaagc agtatgatga ggctctcaat aaacaagact gggtagatgg    9000
tgagcccaca gaagccgaga aggattttttg ggaacttgca tcccttgact gttacaacca    9060
ccttgctgag tggaaatcac ttgaatactg ttctacagcc agtatagaca gtgagaaccc    9120
cccagaccta aataaaatct ggagtgaacc attttatcag gaaacatatc taccttacat    9180
gatccgcagc aagctgaagc tgctgctcca gggagaggct gaccagtccc tgctgacatt    9240
tattgacaaa gctatgcacg gggagctcca gaaggcgatt ctagagcttc attacagtca    9300
agagctgagt ctgctttacc tcctgcaaga tgatgttgac agagccaaat attacattca    9360
aaatggcatt cagagttttta tgcagaatta ttctagtatt gatgtcctct acaccaaag    9420 tagactcacc aaattgcagt ctgtacaggc tttaacagaa attcaggagt tcatcagctt    9480
tataagcaaa caaggcaatt tatcatctca agttcccctt aagagacttc tgaacacctg    9540
gacaaacaga tatccagatg ctaaaatgga cccaatgaac atctgggatg acatcatcac    9600
aaatcgatgt ttctttctca gcaaaataga ggagaagctt acccctcttc cagaagataa    9660
tagtatgaat gtggatcaag atggagaccc cagtgacagg atggaagtgc aagagcagga    9720
agaagatatc agctccctga tcaggagttg caagttttcc atgaaaatga agatgataga    9780
cagtgcccgg aagcagaaca atttctcact tgctatgaaa ctactgaagg agctgcataa    9840
agagtcaaaa accagagacg attggctggt gagctgggtg cagagctact gccgcctgag    9900
ccactgccgg agccggtccc agggctgctc tgagcaggtg ctcactgtgc tgaaaacagt    9960
ctctttgttg gatgagaaca acgtgtcaag ctacttaarc aaaaatattc tggctttccg   10020
tgaccagaac attctcttgg gtacaactta caggatcata gcgaatgctc tcagcagtga   10080
gccagcctgc cttgctgaaa tcgaggagga caaggctaga agaatcttag agctttctgg   10140
atccagttca gaggattcag agaaggtgat cgcgggtctg taccagagag cattccagca   10200
cctctctgag gctgtgcagg cggctgagga ggaggcccag cctccctcct ggagctgtgg   10260
gcctgcagct ggggtgattg atgcttacat gacgctggca gatttctgtg accaacagct   10320
gcgcaaggag gaagagaatg catcagttac tgattctgca gaactgcagg cgtatccagc   10380
acttgtggtg gagaaaatgt tgaaagcttt aaaattaaat tccaatgaag ccagattgaa   10440
gtttcctaga ttacttcaga ttatagaacg gtatccagag gagactttga gcctcatgac   10500
aaaagagatc tcttccgttc cctgctggca gttcatcagc tggatcagcc acatggtggc   10560
cttactggac aaagaccaag ccgttgctgt tcagcactct gtggaagaaa tcactgataa   10620
ctacccgcag gctattgttt atcccttcat cataagcagc gaaagctatt ccttcaagga   10680
tacttctact ggtcataaga ataaggagtt tgtggcaagg attaaaagta agttggatca   10740
aggaggagtg attcaagatt ttattaatgc cttagatcag ctctctaatc ctgaactgct   10800
ctttaaggat tggagcaatg atgtaagagc tgaactagca aaacccctg taaataaaaa   10860 aaacattgaa aaaatgtatg aaagaatgta tgcagccttg ggtgacccaa aggctccagg   10920
cctgggggcc tttagaagga agtttattca gactttttgga aaagaatttg ataaacattt   10980
```

```
tgggaaagga ggttctaaac tactgagaat gaagctcagt gacttcaacg acattaccaa   11040
catgctactt ttaaaaatga acaaagactc aaagccccct gggaatctga agaatgttc    11100 accctggatg agcgacttca aagtggagtt cctgagaaat gagctggaga ttcccggtca   11160
gtatgacggt aggggaaagc cattgccaga gtaccacgtg cgaatcgccg ggtttgatga   11220
gcgggtgaca gtcatggcgt ctctgcgaag gcccaagcgc atcatcatcc gtggccatga   11280
cgagagggaa cacctttcc tggtgaaggg tggcgaggac ctgcggcagg accagcgcgt    11340
ggagcagctc ttccaggtca tgaatgggat cctggcccaa gactccgcct gcagccagag   11400
ggccctgcag ctgaggacct atagcgttgt gcccatgacc tccagtgatc ccagggcacc   11460
gccgtgtgaa tataaagatt ggctgacaaa aatgtcagga aaacatgatg ttggagctta   11520
catgctaatg tataagggcg ctaatcgtac tgaaacagtc acgtctttta gaaaacgaga   11580
aagtaaagtg cctgctgatc tcttaaagcg ggccttcgtg aggatgagta caagccctga   11640
ggctttcctg gcgctccgct cccacttcgc cagctctcac gctctgatat gcatcagcca   11700
ctggatcctc gggattggag acagacatct gaacaacttt atggtggcca tggagactgg   11760
cggcgtgatc gggatcgact ttgggcatgc gtttggatcc gctacacagt ttctgccagt   11820
ccctgagttg atgccttttc ggctaactcg ccagtttatc aatctgatgt taccaatgaa   11880
agaaacgggc cttatgtaca gcatcatggt acacgcactc cgggccttcc gctcagaccc   11940
tggcctgctc accaacacca tggatgtgtt tgtcaaggag ccctcctttg attggaaaaa   12000
ttttgaacag aaaatgctga aaaaggagg gtcatggatt caagaaataa atgttgctga   12060
aaaaaattgg taccccgac agaaaatatg ttacgctaag agaaagttag caggtgccaa   12120
tccagcagtc attacttgtg atgagctact cctgggtcat gagaaggccc ctgccttcag   12180
agactatgtg gctgtggcac gaggaagcaa agatcacaac attcgtgccc aagaaccaga   12240
gagtgggctt tcagaagaga ctcaagtgaa gtgcctgatg gaccaggcaa cagacccccaa   12300 catccttggc agaacctggg aaggatggga gccctggatg tgaggtctgt gggagtctgc   12360
agatagaaag cattacattg tttaaagaat ctactatact tggttggcag cattccatga   12420
gctgattttc ctgaaacact aaagagaaat gtcttttgtg ctacagtttc gtagcatgag   12480
tttaaatcaa gattatgatg agtaaatgtg tatgggttaa atcaaagata aggttatagt   12540
aacatcaaag attaggtgag gtttatagaa agatagatat ccaggcttac caaagtatta   12600
agtcaagaat ataatatgtg atcagctttc aaagcattta caagtgctgc aagttagtga   12660
aacagctgtc tccgtaaatg gaggaaatgt ggggaagcct tggaatgccc ttctggttct   12720
ggcacattgg aaagcacact cagaaggctt catcaccaag attttgggag agtaaagcta   12780
```

<210> SEQ ID NO 9
<211> LENGTH: 10
<212> TYPE: PRT
<213> ORGANISM: Homo sapiens

<400> SEQUENCE: 9

Pro Pro Leu Ser Gln Glu Thr Phe Ser Asp
 1               5                  10

<210> SEQ ID NO 10
<211> LENGTH: 4
<212> TYPE: PRT
<213> ORGANISM: Homo sapiens
<220> FEATURE:
<221> NAME/KEY: SITE

```
<222> LOCATION: (2)
<223> OTHER INFORMATION: Xaa is any amino acid
<220> FEATURE:
<221> NAME/KEY: SITE
<222> LOCATION: (3)
<223> OTHER INFORMATION: Xaa is any amino acid

<400> SEQUENCE: 10

Ser Xaa Xaa Thr
 1

<210> SEQ ID NO 11
<211> LENGTH: 19
<212> TYPE: PRT
<213> ORGANISM: Homo sapiens
<220> FEATURE:
<221> NAME/KEY: SITE
<222> LOCATION: (10)
<223> OTHER INFORMATION: Xaa is uncertain

<400> SEQUENCE: 11

Ser Gly Ser Gly Glu Pro Pro Leu Ser Xaa Glu Thr Phe Ser Asp Leu
 1               5                  10                  15

Trp Lys Leu

<210> SEQ ID NO 12
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 12
cctgcccttg cctga                                                          15

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13
tcaggcaagg gcagg                                                          15

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14
cctgcccttg cctgacgcta ttagt                                               25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 15
```
actaatagcg tcaggcaagg gcagg                                            25

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
ttgtaaaacg acggccagtg aattcatcat caataatata ccttattttg                 50

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
caaaataagg tatattattg atgatgaatt cactggccgt cgttttacaa                 50

<210> SEQ ID NO 18
<211> LENGTH: 75
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 18
gatcgaatcc gatagagtat agatagagta aagtttaaat acttatatag atagagtata      60
gatagagggt tcaaa                                                       75

<210> SEQ ID NO 19
<211> LENGTH: 75
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 19
tttgaaccct ctatctatac tctatctata taagtattta aactttactc tatctatact      60
ctatcggatt cgatc                                                       75

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 20
ttgtaaaacg acggccagtg aattcatcat caataatata ccttattttg                 50

<210> SEQ ID NO 21
<211> LENGTH: 100
<212> TYPE: DNA
<213> ORGANISM: Artificial Sequence
<220> FEATURE:
<223> OTHER INFORMATION: Description of Artificial Sequence:
      Oligonucleotide

```
<400> SEQUENCE: 21
cctgcccttg cctgacgcta ttagttcatc tatttgtttt gctaattcga ttggaatcga      60
aacggtcaca tattctttt tgactgattt cctcggcata                            100

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 22
tatgccgagg aaatcagtca aaaagaata tgtgaccgtt tcgattccaa                  50

<210> SEQ ID NO 23
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
tcgaattagc aaaacaaata gatgaactaa tagcgtcagg caagggcagg                 50

<210> SEQ ID NO 24
<211> LENGTH: 15
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
tatgccgagg aaatc                                                      15

<210> SEQ ID NO 25
<211> LENGTH: 90
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
tatgccgagg aaatcagtca aaaagaata tgtgaccgtt tcgaattagc aaaacaaata      60
gatgaactaa tagcgtcagg caagggcagg                                      90

<210> SEQ ID NO 26
<211> LENGTH: 14
<212> TYPE: PRT
<213> ORGANISM: Homo sapiens

<400> SEQUENCE: 26

Asp Pro Ser Val Glu Pro Pro Leu Ser Gln Glu Thr Phe Ser
 1               5                  10
```